(12) United States Patent
Allyn et al.

(10) Patent No.: US 9,433,339 B2
(45) Date of Patent: Sep. 6, 2016

(54) CATHETER WITH IMAGING ASSEMBLY AND CONSOLE WITH REFERENCE LIBRARY AND RELATED METHODS THEREFOR

(71) Applicant: Covidien LP, Mansfield, MA (US)

(72) Inventors: Robert Allyn, Pacific, MO (US); Glen Branconier, North Attleboro, MA (US); Anthony Sacchetti, Mansfield, MA (US)

(73) Assignee: Covidien LP, Mansfield, MA (US)

( * ) Notice: Subject to any disclaimer, the term of this patent is extended or adjusted under 35 U.S.C. 154(b) by 57 days.

(21) Appl. No.: 13/667,304

(22) Filed: Nov. 2, 2012

(65) Prior Publication Data

US 2013/0303849 A1   Nov. 14, 2013

Related U.S. Application Data

(63) Continuation-in-part of application No. 13/228,075, filed on Sep. 8, 2011.

(60) Provisional application No. 61/482,080, filed on May 3, 2011, provisional application No. 61/380,985, filed on Sep. 8, 2010.

(51) Int. Cl.
*A61B 1/04* (2006.01)
*A61B 1/00* (2006.01)
(Continued)

(52) U.S. Cl.
CPC ......... *A61B 1/00045* (2013.01); *A61B 1/0005* (2013.01); *A61B 1/00119* (2013.01);
(Continued)

(58) Field of Classification Search
CPC ...... A61B 1/0005; A61B 5/06; A61B 1/267; A61B 1/273; A61B 2019/50; A61B 1/2676; A61B 5/6852; A61B 5/743
USPC ......................................... 600/114, 117, 118
See application file for complete search history.

(56) References Cited

U.S. PATENT DOCUMENTS

| | | |
|---|---|---|
| 3,633,758 A | 1/1972 | Morse et al. |
| 3,788,304 A | 1/1974 | Takahashi |

(Continued)

FOREIGN PATENT DOCUMENTS

| | | |
|---|---|---|
| EP | 0299240 A2 | 1/1989 |
| EP | 1347638 A1 | 9/2003 |

(Continued)

OTHER PUBLICATIONS

PCT International Search Report and Written Opinion for PCT/US2011/050863 dated Dec. 11, 2012, 21 pages.

(Continued)

*Primary Examiner* — Anhtuan T Nguyen
*Assistant Examiner* — Alexandra Newton

(57) ABSTRACT

An imaging system having an imaging assembly having an imaging device for generating imaging signals corresponding to images of anatomy of a patient disclosed. The imaging assembly, which may be a component of a feeding tube assembly, transmits the imaging signals generated to a console, which presents images generated corresponding to the imaging signals on a display. A reference menu is presented on the display including menu items, which correspond to reference materials including photographs, video recordings, audio recordings, diagrams, animations, and/or text. Each of the materials provides information about anatomy, patient preparation, imaging catheter preparation, imaging catheter placement, imaging catheter operation, imaging catheter features, console preparation, console operation, console features, system operation, system features, and/or contact information.

14 Claims, 47 Drawing Sheets

(51) Int. Cl.
  *A61B 1/06* (2006.01)
  *A61B 5/00* (2006.01)
  *A61B 1/267* (2006.01)
  *A61J 15/00* (2006.01)

(52) U.S. Cl.
  CPC ............ *A61B1/0684* (2013.01); *A61B 1/2676* (2013.01); *A61B 5/0084* (2013.01); *A61J 15/00* (2013.01); *A61J 15/008* (2015.05); *A61J 15/0003* (2013.01); *A61J 15/0069* (2013.01); *A61J 15/0073* (2013.01)

(56) References Cited

U.S. PATENT DOCUMENTS

| | | |
|---|---|---|
| 4,146,019 A | 3/1979 | Bass et al. |
| 4,253,447 A | 3/1981 | Moore et al. |
| 4,301,790 A | 11/1981 | Bol et al. |
| D267,019 S | 11/1982 | Goldsmith |
| 4,392,485 A | 7/1983 | Hiltebrandt |
| 4,491,865 A | 1/1985 | Danna et al. |
| D281,081 S | 10/1985 | Zwissler et al. |
| 4,616,630 A | 10/1986 | Arakawa |
| 4,621,284 A | 11/1986 | Nishioka et al. |
| 4,769,014 A | 9/1988 | Russo |
| 4,782,819 A | 11/1988 | Adair |
| 4,809,680 A | 3/1989 | Yabe |
| 4,846,153 A | 7/1989 | Berci |
| 4,919,651 A | 4/1990 | Doane |
| 4,996,975 A | 3/1991 | Nakamura |
| 5,025,778 A | 6/1991 | Silverstein et al. |
| 5,059,182 A | 10/1991 | Laing |
| 5,131,380 A | 7/1992 | Heller et al. |
| 5,168,863 A | 12/1992 | Kurtzer |
| 5,187,579 A | 2/1993 | Hiyama |
| 5,220,198 A | 6/1993 | Tsuji |
| 5,242,394 A | 9/1993 | Tremulis |
| 5,285,778 A | 2/1994 | Mackin |
| 5,297,477 A | 3/1994 | Phillips |
| 5,329,940 A | 7/1994 | Adair |
| 5,334,150 A | 8/1994 | Kaali |
| 5,353,783 A | 10/1994 | Nakao et al. |
| 5,400,771 A * | 3/1995 | Pirak ............... A61B 1/042 128/200.26 |
| 5,409,480 A | 4/1995 | Uram |
| 5,423,311 A | 6/1995 | Snoke et al. |
| 5,435,339 A | 7/1995 | Hayes |
| 5,469,254 A | 11/1995 | Konomura |
| 5,526,928 A | 6/1996 | Yabe et al. |
| 5,527,261 A | 6/1996 | Monroe et al. |
| 5,604,531 A | 2/1997 | Iddan et al. |
| 5,610,828 A | 3/1997 | Kodosky et al. |
| 5,636,625 A | 6/1997 | Miyagi et al. |
| 5,638,819 A | 6/1997 | Manwaring et al. |
| 5,645,519 A | 7/1997 | Lee et al. |
| 5,665,064 A | 9/1997 | Bodicky et al. |
| 5,676,635 A | 10/1997 | Levin |
| D390,666 S | 2/1998 | Lagerlof |
| D391,247 S | 2/1998 | Wanishi et al. |
| 5,720,293 A | 2/1998 | Quinn et al. |
| D393,850 S | 4/1998 | Norton |
| 5,740,802 A | 4/1998 | Nafis et al. |
| 5,772,693 A | 6/1998 | Brownlee |
| D398,595 S | 9/1998 | Baer et al. |
| 5,817,015 A | 10/1998 | Adair |
| 5,830,121 A | 11/1998 | Enomoto et al. |
| 5,848,691 A | 12/1998 | Morris et al. |
| 5,873,816 A | 2/1999 | Kagawa et al. |
| D406,894 S | 3/1999 | Menhennett et al. |
| 5,896,166 A | 4/1999 | D'Alfonso et al. |
| 5,908,294 A | 6/1999 | Schick et al. |
| 5,913,816 A | 6/1999 | Sanders et al. |
| 5,929,901 A | 7/1999 | Adair et al. |
| D412,748 S | 8/1999 | Nabarro |
| 5,932,035 A | 8/1999 | Koger et al. |
| 5,938,603 A | 8/1999 | Ponzi |
| 5,941,816 A | 8/1999 | Barthel et al. |
| D414,870 S | 10/1999 | Saltzstein et al. |
| 5,967,988 A | 10/1999 | Briscoe et al. |
| 5,986,693 A | 11/1999 | Adair et al. |
| 5,989,230 A | 11/1999 | Frassica |
| 5,989,231 A | 11/1999 | Snow et al. |
| 6,004,263 A | 12/1999 | Nakaichi et al. |
| 6,043,839 A | 3/2000 | Adair et al. |
| 6,053,313 A | 4/2000 | Farrell et al. |
| D426,204 S | 6/2000 | Maio et al. |
| 6,099,354 A | 8/2000 | Troyan |
| 6,115,523 A | 9/2000 | Choi et al. |
| 6,117,071 A | 9/2000 | Ito et al. |
| 6,120,435 A | 9/2000 | Eino |
| 6,198,963 B1 | 3/2001 | Haim et al. |
| 6,237,604 B1 | 5/2001 | Burnside et al. |
| 6,245,029 B1 | 6/2001 | Fujita et al. |
| D447,569 S | 9/2001 | Baily et al. |
| 6,310,642 B1 | 10/2001 | Adair et al. |
| 6,322,498 B1 | 11/2001 | Gravenstein et al. |
| 6,339,446 B1 | 1/2002 | Miyoshi |
| D455,760 S | 4/2002 | Platz |
| D456,027 S | 4/2002 | Boehler et al. |
| 6,364,827 B1 | 4/2002 | Irion et al. |
| D459,477 S | 6/2002 | Stocks et al. |
| 6,447,444 B1 | 9/2002 | Avni et al. |
| 6,458,076 B1 | 10/2002 | Pruitt |
| 6,462,770 B1 | 10/2002 | Cline et al. |
| 6,468,212 B1 | 10/2002 | Scott et al. |
| D465,789 S | 11/2002 | Platz |
| D466,519 S | 12/2002 | Shim et al. |
| D470,505 S | 2/2003 | Platz |
| 6,520,916 B1 | 2/2003 | Brennen |
| D471,226 S | 3/2003 | Gray |
| D471,227 S | 3/2003 | Gray |
| 6,543,447 B2 | 4/2003 | Pacey |
| 6,547,757 B1 | 4/2003 | Kranz et al. |
| 6,550,475 B1 | 4/2003 | Oldfield |
| 6,553,241 B2 | 4/2003 | Mannheimer et al. |
| 6,554,765 B1 | 4/2003 | Yarush et al. |
| 6,565,506 B2 | 5/2003 | Ishizuka |
| 6,585,639 B1 | 7/2003 | Kotmel et al. |
| 6,612,980 B2 | 9/2003 | Chen et al. |
| 6,623,480 B1 | 9/2003 | Kuo et al. |
| 6,626,828 B2 | 9/2003 | Dohi et al. |
| D483,872 S | 12/2003 | Cruz et al. |
| 6,655,377 B2 | 12/2003 | Pacey |
| 6,692,430 B2 | 2/2004 | Adler |
| 6,692,432 B1 | 2/2004 | Yarush et al. |
| 6,712,756 B1 | 3/2004 | Kura et al. |
| 6,712,760 B2 | 3/2004 | Sano et al. |
| D491,954 S | 6/2004 | Platz et al. |
| 6,761,561 B2 | 7/2004 | Mandelkern et al. |
| 6,814,727 B2 | 11/2004 | Mansouri-Ruiz |
| 6,860,611 B2 | 3/2005 | Gentz |
| 6,862,467 B2 | 3/2005 | Moore et al. |
| 6,875,169 B2 | 4/2005 | Berci et al. |
| 6,890,298 B2 | 5/2005 | Berci et al. |
| D506,195 S | 6/2005 | Leveridge et al. |
| 6,902,529 B2 | 6/2005 | Onishi et al. |
| 6,909,795 B2 | 6/2005 | Tecotzky et al. |
| 6,911,027 B1 | 6/2005 | Edwards et al. |
| 6,929,600 B2 | 8/2005 | Hill |
| 6,945,929 B2 | 9/2005 | Ando |
| 6,960,161 B2 | 11/2005 | Amling et al. |
| 6,966,876 B2 | 11/2005 | Irion et al. |
| 6,986,738 B2 | 1/2006 | Glukhovsky et al. |
| D514,558 S | 2/2006 | Nagel et al. |
| 7,011,285 B2 | 3/2006 | Wang et al. |
| 7,022,075 B2 | 4/2006 | Grunwald et al. |
| 7,033,316 B2 | 4/2006 | Takahashi |
| 7,048,687 B1 | 5/2006 | Reuss et al. |
| 7,063,660 B2 | 6/2006 | Chen et al. |
| 7,063,663 B2 | 6/2006 | Kazakevich |
| 7,090,661 B2 | 8/2006 | Morris et al. |
| 7,126,581 B2 | 10/2006 | Burk et al. |
| 7,131,873 B2 | 11/2006 | Miyake et al. |
| 7,151,956 B2 | 12/2006 | Satoh et al. |
| 7,223,232 B2 | 5/2007 | Mizuno |

(56) References Cited

U.S. PATENT DOCUMENTS

| | | |
|---|---|---|
| 7,270,650 B2 | 9/2007 | Morris et al. |
| 7,273,452 B2 | 9/2007 | Barbato et al. |
| 7,288,074 B2 | 10/2007 | Swain et al. |
| 7,297,105 B2 | 11/2007 | Mackin |
| D558,351 S | 12/2007 | Diener et al. |
| 7,303,528 B2 | 12/2007 | Couvillon, Jr. |
| 7,304,277 B2 | 12/2007 | Weber |
| D562,456 S | 2/2008 | Scruggs et al. |
| 7,366,562 B2 | 4/2008 | Dukesherer et al. |
| 7,373,005 B2 | 5/2008 | Venkataraman |
| 7,391,606 B2 | 6/2008 | Chen et al. |
| 7,404,794 B2 | 7/2008 | Scholly |
| 7,413,543 B2 | 8/2008 | Banik et al. |
| 7,423,496 B2 | 9/2008 | Scheuermann |
| D582,916 S | 12/2008 | Wada |
| 7,471,310 B2 | 12/2008 | Amling et al. |
| 7,491,167 B2 | 2/2009 | Ogino et al. |
| 7,497,825 B2 | 3/2009 | Sarwari |
| D591,423 S | 4/2009 | Diener et al. |
| 7,530,946 B2 | 5/2009 | Hartwick |
| 7,547,277 B2 | 6/2009 | Wiklof et al. |
| D598,109 S | 8/2009 | Collins et al. |
| 7,585,273 B2 | 9/2009 | Adler et al. |
| 7,591,780 B2 | 9/2009 | Jacobsen et al. |
| D601,582 S | 10/2009 | Chaudhri et al. |
| 7,604,627 B2 | 10/2009 | Kojouri |
| 7,628,752 B2 | 12/2009 | Yamamoto et al. |
| 7,651,277 B2 | 1/2010 | Gurreri et al. |
| D609,350 S | 2/2010 | Hickey et al. |
| 7,660,453 B2 | 2/2010 | Lang |
| 7,662,151 B2 | 2/2010 | Crompton, Jr. et al. |
| 7,672,491 B2 | 3/2010 | Krishnan et al. |
| D613,411 S | 4/2010 | Collins et al. |
| D614,634 S | 4/2010 | Nilsen |
| D615,199 S | 5/2010 | Zimmerli et al. |
| 7,713,189 B2 | 5/2010 | Hanke |
| 7,740,578 B2 | 6/2010 | Little |
| D621,515 S | 8/2010 | Chua et al. |
| 7,773,122 B2 | 8/2010 | Irion et al. |
| 7,780,650 B2 | 8/2010 | Frassica et al. |
| 7,787,939 B2 | 8/2010 | Jacobsen et al. |
| 7,789,823 B2 | 9/2010 | Kato et al. |
| 7,806,121 B2 | 10/2010 | Bodduluri |
| 7,831,070 B1 | 11/2010 | Cheng et al. |
| 7,846,091 B2 | 12/2010 | Fulghum |
| 7,850,370 B2 | 12/2010 | Murano |
| 7,860,555 B2 | 12/2010 | Saadat |
| 7,860,556 B2 | 12/2010 | Saadat |
| 7,896,802 B2 | 3/2011 | Otawara |
| 7,898,085 B2 | 3/2011 | Fujimori |
| 7,901,348 B2 | 3/2011 | Soper et al. |
| 7,901,353 B2 | 3/2011 | Vayser et al. |
| 7,914,448 B2 | 3/2011 | Bob et al. |
| 7,922,654 B2 | 4/2011 | Boutillette et al. |
| 7,930,016 B1 | 4/2011 | Saadat |
| D638,943 S | 5/2011 | Daniel |
| 7,942,814 B2 | 5/2011 | Remijan et al. |
| 7,976,459 B2 | 7/2011 | Laser |
| 7,978,891 B2 | 7/2011 | Assmann et al. |
| 7,985,213 B2 | 7/2011 | Parker |
| D643,936 S | 8/2011 | Oonuma et al. |
| D644,246 S | 8/2011 | Matas |
| 7,993,264 B2 | 8/2011 | Crank |
| 7,998,062 B2 | 8/2011 | Gilboa |
| 8,016,749 B2 | 9/2011 | Clerc et al. |
| 8,049,061 B2 | 11/2011 | Ehrenreich et al. |
| 8,050,746 B2 | 11/2011 | Saadat et al. |
| 8,052,596 B2 | 11/2011 | Kim |
| 8,069,420 B2 | 11/2011 | Plummer |
| D650,484 S | 12/2011 | Shinohara et al. |
| 8,075,477 B2 | 12/2011 | Nakamura et al. |
| 8,075,583 B2 | 12/2011 | Lee et al. |
| 8,135,195 B2 | 3/2012 | Mahesh et al. |
| 8,139,296 B2 | 3/2012 | Ito |
| D657,059 S | 4/2012 | Geijsen et al. |
| D658,295 S | 4/2012 | Geijsen et al. |
| 8,152,560 B2 | 4/2012 | Malstron et al. |
| 8,152,712 B2 | 4/2012 | Abe |
| 8,160,676 B2 | 4/2012 | Gielen et al. |
| 8,162,820 B2 | 4/2012 | Moore |
| 8,162,824 B2 | 4/2012 | Vayser et al. |
| 8,162,825 B2 | 4/2012 | Matsumoto et al. |
| D659,836 S | 5/2012 | Bensch et al. |
| 8,172,864 B2 | 5/2012 | Wu |
| 8,183,510 B2 | 5/2012 | Venezia et al. |
| 8,194,121 B2 | 6/2012 | Blumzvig et al. |
| 8,194,122 B2 | 6/2012 | Amling et al. |
| 8,199,187 B2 | 6/2012 | Knapp, II et al. |
| 8,206,289 B2 | 6/2012 | Zen |
| 8,206,374 B2 | 6/2012 | Duane et al. |
| 8,211,128 B1 | 7/2012 | Facundus et al. |
| 8,216,185 B2 | 7/2012 | Berger |
| 8,228,369 B2 | 7/2012 | Kojima et al. |
| 8,231,522 B2 | 7/2012 | Endo et al. |
| 8,235,887 B2 | 8/2012 | Bayer et al. |
| 8,241,199 B2 | 8/2012 | Maschke |
| 8,262,559 B2 | 9/2012 | Krattiger |
| 8,262,622 B2 | 9/2012 | Gonzales et al. |
| 8,265,732 B2 | 9/2012 | Besz et al. |
| 8,280,205 B2 | 10/2012 | Erdman et al. |
| 8,285,362 B2 | 10/2012 | Dietz et al. |
| 8,292,874 B2 | 10/2012 | Stivland et al. |
| 8,297,440 B2 | 10/2012 | Schmidt et al. |
| 8,308,637 B2 | 11/2012 | Ishigami et al. |
| 8,314,835 B2 | 11/2012 | Kanzaki et al. |
| 8,317,689 B1 | 11/2012 | Remijan et al. |
| 8,336,541 B2 | 12/2012 | Schwartz et al. |
| 8,360,964 B2 | 1/2013 | Ertas |
| 8,386,023 B2 | 2/2013 | Furnish |
| 8,388,376 B2 | 3/2013 | Yamamoto et al. |
| 8,390,995 B2 | 3/2013 | Wang et al. |
| 8,400,767 B2 | 3/2013 | Yeom et al. |
| 8,403,836 B2 | 3/2013 | Shimotsu |
| 8,408,269 B2 | 4/2013 | Fengler et al. |
| 8,408,815 B2 | 4/2013 | Lin et al. |
| 8,409,081 B2 | 4/2013 | Takahashi |
| 8,421,626 B2 | 4/2013 | Downie et al. |
| 8,425,405 B2 | 4/2013 | Mitani et al. |
| 8,444,802 B2 | 5/2013 | Lee et al. |
| 8,454,578 B2 | 6/2013 | Leeflang et al. |
| 8,471,392 B2 | 6/2013 | Kojima |
| 8,480,404 B2 | 7/2013 | Savitsky |
| 8,485,966 B2 | 7/2013 | Robertson |
| 8,485,967 B2 | 7/2013 | Takahashi et al. |
| 8,486,023 B2 | 7/2013 | Pyles |
| 8,496,001 B2 | 7/2013 | Schermeier et al. |
| 8,496,574 B2 | 7/2013 | Trusty et al. |
| 8,496,580 B2 | 7/2013 | Dotan et al. |
| 8,512,232 B2 | 8/2013 | Rothberg et al. |
| 8,514,556 B2 | 8/2013 | Huang et al. |
| 8,547,689 B2 | 10/2013 | Moser |
| 8,556,806 B2 | 10/2013 | Farr |
| 8,568,159 B2 | 10/2013 | Noda et al. |
| 8,573,824 B2 | 11/2013 | Komukai et al. |
| 8,574,192 B2 | 11/2013 | Haarala et al. |
| 8,585,586 B2 | 11/2013 | Yamaguchi et al. |
| 8,587,710 B2 | 11/2013 | Jeon |
| 8,591,407 B2 | 11/2013 | Wendlandt et al. |
| D695,410 S | 12/2013 | Becker |
| 8,597,179 B2 | 12/2013 | Kokubo |
| 8,599,264 B2 | 12/2013 | Schmidt |
| 8,600,133 B2 | 12/2013 | Buelow et al. |
| 8,602,967 B2 | 12/2013 | Robertson |
| 8,602,979 B2 | 12/2013 | Kitano |
| 8,606,347 B2 | 12/2013 | Besz et al. |
| 2002/0007108 A1 | 1/2002 | Chen et al. |
| 2002/0126960 A1 | 9/2002 | Gurreri |
| 2003/0055314 A1 | 3/2003 | Petitto et al. |
| 2003/0060678 A1 | 3/2003 | Watai et al. |
| 2003/0112921 A1 | 6/2003 | Lang et al. |
| 2004/0097805 A1 | 5/2004 | Verard et al. |
| 2004/0111081 A1 | 6/2004 | Whitman et al. |
| 2004/0133074 A1 | 7/2004 | Chen et al. |
| 2004/0165833 A1 | 8/2004 | Betker et al. |

(56) References Cited

U.S. PATENT DOCUMENTS

| | | |
|---|---|---|
| 2004/0171914 A1 | 9/2004 | Avni |
| 2004/0181431 A1 | 9/2004 | Kuth et al. |
| 2004/0199088 A1 | 10/2004 | Bakos et al. |
| 2004/0210295 A1 | 10/2004 | Brushey |
| 2004/0237048 A1 | 11/2004 | Tojo et al. |
| 2004/0239760 A1 | 12/2004 | Shoji et al. |
| 2004/0252871 A1 | 12/2004 | Tecotzky et al. |
| 2005/0021182 A1 | 1/2005 | Wang et al. |
| 2005/0038318 A1 | 2/2005 | Goldwasser |
| 2005/0054895 A1 | 3/2005 | Hoeg et al. |
| 2005/0054914 A1 | 3/2005 | Duerk et al. |
| 2005/0073017 A1 | 4/2005 | Kim |
| 2005/0154262 A1 | 7/2005 | Banik et al. |
| 2005/0177024 A1 | 8/2005 | Mackin |
| 2005/0192477 A1 | 9/2005 | Forster et al. |
| 2005/0200698 A1 | 9/2005 | Amling et al. |
| 2005/0203338 A1 | 9/2005 | Couvillon, Jr. et al. |
| 2005/0216041 A1 | 9/2005 | Okada et al. |
| 2005/0250983 A1 | 11/2005 | Tremaglio et al. |
| 2005/0251013 A1 | 11/2005 | Krishnan et al. |
| 2005/0277808 A1 | 12/2005 | Sonnenschein et al. |
| 2006/0004286 A1 | 1/2006 | Chang et al. |
| 2006/0020171 A1 | 1/2006 | Gilreath |
| 2006/0025650 A1 | 2/2006 | Gavriely |
| 2006/0117185 A1 | 6/2006 | Oguri et al. |
| 2006/0122460 A1 | 6/2006 | Kamali |
| 2006/0171586 A1 | 8/2006 | Georgescu et al. |
| 2006/0171856 A1 | 8/2006 | Jehle |
| 2006/0224040 A1 | 10/2006 | Khait et al. |
| 2006/0235274 A1 | 10/2006 | Forster et al. |
| 2006/0264918 A1 | 11/2006 | Cook et al. |
| 2006/0287576 A1 | 12/2006 | Tsuji et al. |
| 2007/0049794 A1 | 3/2007 | Glassenberg et al. |
| 2007/0075208 A1 | 4/2007 | Chen |
| 2007/0113204 A1 | 5/2007 | Son et al. |
| 2007/0162095 A1 | 7/2007 | Kimmel et al. |
| 2007/0167682 A1 | 7/2007 | Goldfarb et al. |
| 2007/0225561 A1 | 9/2007 | Watanabe et al. |
| 2007/0232882 A1 | 10/2007 | Glossop et al. |
| 2007/0235626 A1 | 10/2007 | Mamizuka et al. |
| 2008/0021273 A1 | 1/2008 | MacKin |
| 2008/0037850 A1 | 2/2008 | Assmann et al. |
| 2008/0045800 A2 | 2/2008 | Farr |
| 2008/0062624 A1 | 3/2008 | Regen et al. |
| 2008/0074492 A1 | 3/2008 | Iwasaki |
| 2008/0077043 A1 | 3/2008 | Malbrain et al. |
| 2008/0081949 A1 | 4/2008 | Gilad |
| 2008/0091065 A1 | 4/2008 | Oshima et al. |
| 2008/0108869 A1 | 5/2008 | Sanders et al. |
| 2008/0123922 A1 | 5/2008 | Gielen et al. |
| 2008/0139896 A1 | 6/2008 | Baumgart |
| 2008/0140020 A1 | 6/2008 | Shirley |
| 2008/0147000 A1 | 6/2008 | Seibel et al. |
| 2008/0172006 A1 | 7/2008 | Hicks |
| 2008/0236575 A1 | 10/2008 | Chuda |
| 2008/0240527 A1 | 10/2008 | Keller |
| 2008/0255416 A1 | 10/2008 | Gilboa |
| 2008/0275301 A1 | 11/2008 | Lubowski et al. |
| 2008/0281157 A1 | 11/2008 | Miyagi et al. |
| 2008/0281351 A1 | 11/2008 | Croushorn et al. |
| 2008/0294000 A1 | 11/2008 | Iwamoto |
| 2008/0294007 A1 | 11/2008 | Takada |
| 2008/0300456 A1 | 12/2008 | Irion et al. |
| 2008/0319391 A1 | 12/2008 | Jackson |
| 2009/0030276 A1 | 1/2009 | Saadat et al. |
| 2009/0030283 A1 | 1/2009 | Freystein et al. |
| 2009/0043167 A1 | 2/2009 | Leiner |
| 2009/0046906 A1 | 2/2009 | Wohlgemuth et al. |
| 2009/0054803 A1 | 2/2009 | Saadat et al. |
| 2009/0060425 A1 | 3/2009 | Aronson |
| 2009/0062609 A1 | 3/2009 | Suda |
| 2009/0069694 A1 | 3/2009 | Amundson et al. |
| 2009/0082625 A1 | 3/2009 | Gono |
| 2009/0099417 A1 | 4/2009 | Hartwick |
| 2009/0105538 A1 | 4/2009 | Van Dam et al. |
| 2009/0118577 A9 | 5/2009 | Snay et al. |
| 2009/0118580 A1 | 5/2009 | Sun et al. |
| 2009/0137893 A1 | 5/2009 | Seibel et al. |
| 2009/0143648 A1 | 6/2009 | Sutoh et al. |
| 2009/0143651 A1 | 6/2009 | Kallback et al. |
| 2009/0149705 A1 | 6/2009 | Tani et al. |
| 2009/0149706 A1 | 6/2009 | Yamazaki et al. |
| 2009/0155750 A1 | 6/2009 | Abe |
| 2009/0161927 A1 | 6/2009 | Mori et al. |
| 2009/0163769 A1 | 6/2009 | Robertson et al. |
| 2009/0167851 A1 | 7/2009 | Miller et al. |
| 2009/0171148 A1 | 7/2009 | Lu et al. |
| 2009/0177032 A1 | 7/2009 | Garibaldi et al. |
| 2009/0187425 A1 | 7/2009 | Thompson |
| 2009/0198102 A1 | 8/2009 | Chen et al. |
| 2009/0198106 A1 | 8/2009 | Ichihashi |
| 2009/0209826 A1 | 8/2009 | Sanders et al. |
| 2009/0213140 A1 | 8/2009 | Ito et al. |
| 2009/0214089 A1 | 8/2009 | Stookey |
| 2009/0216080 A1 | 8/2009 | Nakamura |
| 2009/0225159 A1 | 9/2009 | Schneider et al. |
| 2009/0234220 A1 | 9/2009 | Maschke |
| 2009/0237497 A1 | 9/2009 | Iinuma et al. |
| 2009/0253955 A1 | 10/2009 | Akiba |
| 2009/0259097 A1 | 10/2009 | Thompson |
| 2009/0268019 A1 | 10/2009 | Ishii et al. |
| 2009/0275799 A1 | 11/2009 | Saadat et al. |
| 2009/0299137 A1 | 12/2009 | Gal et al. |
| 2009/0299363 A1 | 12/2009 | Saadat et al. |
| 2009/0316975 A1 | 12/2009 | Kunz et al. |
| 2009/0318757 A1* | 12/2009 | Singh .................... 600/109 |
| 2009/0318758 A1 | 12/2009 | Farr et al. |
| 2009/0318797 A1 | 12/2009 | Hadani |
| 2009/0318798 A1 | 12/2009 | Singh et al. |
| 2009/0326321 A1 | 12/2009 | Jacobsen et al. |
| 2009/0326481 A1 | 12/2009 | Swisher et al. |
| 2010/0010302 A1 | 1/2010 | Hadani |
| 2010/0010334 A1 | 1/2010 | Bleich et al. |
| 2010/0016757 A1 | 1/2010 | Greenburg et al. |
| 2010/0022824 A1 | 1/2010 | Cybulski et al. |
| 2010/0030020 A1 | 2/2010 | Sanders et al. |
| 2010/0030057 A1 | 2/2010 | Gavriely et al. |
| 2010/0030138 A1 | 2/2010 | Kantsevoy et al. |
| 2010/0047733 A1 | 2/2010 | Nahlieli |
| 2010/0063352 A1 | 3/2010 | Matsuura |
| 2010/0063355 A1 | 3/2010 | Matsuura |
| 2010/0073470 A1 | 3/2010 | Takasaki |
| 2010/0081873 A1 | 4/2010 | Tanimura et al. |
| 2010/0085273 A1 | 4/2010 | Nakayama |
| 2010/0121139 A1 | 5/2010 | OuYang et al. |
| 2010/0121142 A1 | 5/2010 | OuYange et al. |
| 2010/0121155 A1 | 5/2010 | OuYange et al. |
| 2010/0174141 A1 | 7/2010 | Gilad et al. |
| 2010/0179384 A1 | 7/2010 | Hoeg et al. |
| 2010/0191053 A1 | 7/2010 | Garcia et al. |
| 2010/0198009 A1 | 8/2010 | Farr et al. |
| 2010/0204546 A1 | 8/2010 | Hassidov et al. |
| 2010/0204561 A1 | 8/2010 | Saadat et al. |
| 2010/0211005 A1 | 8/2010 | Edwards et al. |
| 2010/0230140 A1 | 9/2010 | Huang et al. |
| 2010/0249507 A1* | 9/2010 | Prisco et al. .................... 600/117 |
| 2010/0249512 A1 | 9/2010 | McKinley et al. |
| 2010/0249639 A1 | 9/2010 | Bhatt |
| 2010/0280316 A1 | 11/2010 | Dietz et al. |
| 2010/0286475 A1 | 11/2010 | Robertson |
| 2010/0286477 A1 | 11/2010 | OuYang et al. |
| 2010/0305503 A1 | 12/2010 | Fang et al. |
| 2011/0004058 A1 | 1/2011 | Oneda et al. |
| 2011/0009694 A1 | 1/2011 | Schultz et al. |
| 2011/0015614 A1 | 1/2011 | Rykhus, Jr. et al. |
| 2011/0034769 A1 | 2/2011 | Adair et al. |
| 2011/0036965 A1 | 2/2011 | Zhang et al. |
| 2011/0037876 A1 | 2/2011 | Talbert et al. |
| 2011/0098530 A1 | 4/2011 | Yamane |
| 2011/0113329 A1 | 5/2011 | Pusateri |
| 2011/0130627 A1 | 6/2011 | McGrail et al. |
| 2011/0130631 A1 | 6/2011 | Geisser et al. |
| 2011/0137117 A1 | 6/2011 | Jacobsen et al. |
| 2011/0137118 A1 | 6/2011 | Huang |

(56) References Cited

U.S. PATENT DOCUMENTS

| | | |
|---|---|---|
| 2011/0137127 A1 | 6/2011 | Schwartz et al. |
| 2011/0144481 A1 | 6/2011 | Feer et al. |
| 2011/0152613 A1 | 6/2011 | Zubiate et al. |
| 2011/0160535 A1 | 6/2011 | Bayer et al. |
| 2011/0160537 A1 | 6/2011 | Chen |
| 2011/0172687 A1 | 7/2011 | Woodruff et al. |
| 2011/0196204 A1 | 8/2011 | Setty et al. |
| 2011/0201882 A1 | 8/2011 | Schwartz et al. |
| 2011/0218400 A1 | 9/2011 | Ma et al. |
| 2011/0245605 A1 | 10/2011 | Jacobsen et al. |
| 2011/0245606 A1 | 10/2011 | Hayashi et al. |
| 2011/0245607 A1 | 10/2011 | Hayashi et al. |
| 2011/0245608 A1 | 10/2011 | Takahashi et al. |
| 2011/0249025 A1 | 10/2011 | Mitani et al. |
| 2011/0249106 A1 | 10/2011 | Makino et al. |
| 2011/0251456 A1 | 10/2011 | Jacobsen et al. |
| 2011/0255760 A1 | 10/2011 | Mahesh et al. |
| 2011/0257478 A1 | 10/2011 | Kleiner et al. |
| 2011/0263938 A1 | 10/2011 | Levy |
| 2011/0270295 A1 | 11/2011 | Litvack et al. |
| 2011/0275894 A1 | 11/2011 | Mackin |
| 2011/0282144 A1 | 11/2011 | Gettman |
| 2011/0288372 A1 | 11/2011 | Petersen |
| 2011/0289441 A1 | 11/2011 | Venon et al. |
| 2011/0294361 A1 | 12/2011 | Schrader |
| 2011/0295061 A1 | 12/2011 | Haramaty et al. |
| 2011/0295072 A1 | 12/2011 | Boulais et al. |
| 2011/0301415 A1 | 12/2011 | Motai et al. |
| 2011/0311116 A1 | 12/2011 | Benn |
| 2012/0006950 A1 | 1/2012 | Vandiver |
| 2012/0010469 A1 | 1/2012 | Boyer |
| 2012/0029279 A1 | 2/2012 | Kucklick |
| 2012/0029290 A1 | 2/2012 | Nishijima |
| 2012/0058457 A1 | 3/2012 | Savitsky |
| 2012/0062714 A1 | 3/2012 | Liu et al. |
| 2012/0065469 A1 | 3/2012 | Allyn et al. |
| 2012/0071723 A1 | 3/2012 | Ishagami et al. |
| 2012/0078174 A1 | 3/2012 | Tai et al. |
| 2012/0084680 A1 | 4/2012 | Gimpl et al. |
| 2012/0086790 A1 | 4/2012 | Takahira et al. |
| 2012/0108960 A1 | 5/2012 | Halmann et al. |
| 2012/0130171 A1 | 5/2012 | Barak et al. |
| 2012/0131488 A1 | 5/2012 | Karlsson et al. |
| 2012/0136212 A1 | 5/2012 | Komukai et al. |
| 2012/0172665 A1 | 7/2012 | Allyn et al. |
| 2012/0190922 A1 | 7/2012 | Kaku |
| 2012/0197078 A1 | 8/2012 | Stanley |
| 2012/0197086 A1 | 8/2012 | Morris et al. |
| 2012/0203065 A1* | 8/2012 | Higgins .............. A61B 1/2676 600/109 |
| 2012/0242814 A1 | 9/2012 | Kubala et al. |
| 2012/0316515 A1 | 12/2012 | Terry |
| 2013/0007668 A1 | 1/2013 | Liu et al. |
| 2013/0027533 A1 | 1/2013 | McDowell |
| 2013/0030249 A1 | 1/2013 | Vazales et al. |
| 2013/0035589 A1 | 2/2013 | Besz et al. |
| 2013/0066150 A1 | 3/2013 | Lee et al. |
| 2013/0067397 A1 | 3/2013 | Kirschner et al. |
| 2013/0103000 A1 | 4/2013 | Vogelbaum et al. |
| 2013/0128020 A1 | 5/2013 | Fujimori |
| 2013/0155591 A1 | 6/2013 | Yamaguchi et al. |
| 2013/0162789 A1 | 6/2013 | Chou et al. |
| 2013/0169777 A1 | 7/2013 | Zen |
| 2013/0172678 A1 | 7/2013 | Kennedy, II et al. |
| 2013/0177222 A1 | 7/2013 | Tridandapani et al. |
| 2013/0184584 A1 | 7/2013 | Berkey |
| 2013/0184683 A1 | 7/2013 | Chow et al. |
| 2013/0188030 A1 | 7/2013 | Igarashi |
| 2013/0197484 A1 | 8/2013 | Seddon et al. |
| 2013/0198687 A1 | 8/2013 | Bird et al. |
| 2013/0216112 A1 | 8/2013 | Graessner |
| 2013/0231533 A1 | 9/2013 | Papademetriou et al. |
| 2013/0237755 A1 | 9/2013 | Singh |
| 2013/0245568 A1 | 9/2013 | Kerr |
| 2013/0250061 A1 | 9/2013 | Hofer |
| 2013/0250079 A1 | 9/2013 | Nakamura et al. |
| 2013/0253348 A1 | 9/2013 | Tremper |
| 2013/0265403 A1 | 10/2013 | Okawa et al. |
| 2013/0271588 A1 | 10/2013 | Kirma et al. |
| 2013/0303849 A1 | 11/2013 | Allyn et al. |
| 2013/0317300 A1 | 11/2013 | Berci et al. |
| 2013/0324968 A1 | 12/2013 | Klein |
| 2014/0052475 A1 | 2/2014 | Madan et al. |

FOREIGN PATENT DOCUMENTS

| | | |
|---|---|---|
| EP | 1421913 A1 | 5/2004 |
| EP | 1707102 A1 | 10/2006 |
| EP | 1709899 A1 | 10/2006 |
| EP | 1847214 A2 | 10/2007 |
| EP | 1849401 A1 | 10/2007 |
| EP | 1707123 B1 | 6/2008 |
| GB | 2448421 A | 10/2008 |
| JP | 54-049192 U | 4/1979 |
| JP | 08-191440 | 7/1996 |
| JP | 2002-214127 | 7/2002 |
| JP | 2004-181237 | 7/2004 |
| JP | 2008194334 A | 8/2008 |
| JP | 2009056238 A | 3/2009 |
| WO | 0167964 A2 | 9/2001 |
| WO | 02/055126 A2 | 7/2002 |
| WO | 2004030526 A1 | 4/2004 |
| WO | 2004060158 A1 | 7/2004 |
| WO | 2005102175 A2 | 11/2005 |
| WO | 2006018841 A2 | 2/2006 |
| WO | 2006070360 A1 | 7/2006 |
| WO | 2006071948 A2 | 7/2006 |
| WO | 2007121139 A2 | 10/2007 |
| WO | 2009049322 A2 | 4/2009 |
| WO | 2009/108854 A1 | 9/2009 |
| WO | 2010066788 A2 | 6/2010 |
| WO | 2010123858 A2 | 10/2010 |
| WO | 2011018812 A1 | 2/2011 |
| WO | 2011126812 A1 | 10/2011 |
| WO | 2012033936 A2 | 3/2012 |

OTHER PUBLICATIONS

European Office Action issued Feb. 18, 2014 from related Patent Application No. 11758634.7, 4 pages.
European Search Report for EP 14150398.7 issued Feb. 19, 2014, 6 pages.
European Search Report for EP 14150399.5 issued Feb. 19, 2014, 7 pages.
International Search Report regarding corresponding PCT/US2013/064070, dated Jan. 22, 2014, 5 pages.
Written Opinion of the International Searching Authority, PCT/US2013/064070, dated Jan. 22, 2014, 8 pages.
Office Action dated Feb. 18, 2014 in related Japanese Patent Application Serial No. 2013528290, 2 pages.
Response filed Jan. 7, 2014 to Office Action issued Nov. 7, 2013 from related U.S. Appl. No. 13/228,075, 18 pgs.
Australian Patent Examination Report No. 1, Patent Application No. 2011299149, dated Aug. 15, 2013, 4 pgs.
Office Action issued Jun. 27, 2013 in related U.S. Appl. No. 13/228,075, 12 pages.
1000 Icons, Symbols + Pictograms: Visual Communication for Every Language, Rockport Publishers, Gloucester, MA 2006, p. 89.
Logo Lounge, by Bill Gardner and Catharine Fishel, Rockport Publishers, Goucester, MA 2003, p. 131.
Logo Lounge 2, by Bill Gardner and Catherine Fishel, Rockport Publishers, Gloucester, MA 2005, pp. 92 and 112.
Symbol Sourcebook, by Henry Dreyfuss, Van Nostrand Reinhold Company, New York, NY, 1972, p. 118.
European Search Report in related European Application 14164448.4 dated May 9, 2014, 6 pages.
European Search Report in related European Application 14165017.6 dated May 30, 2014, 6 pages.
U.S. Office Action in related U.S. Appl. No. 13/347,787 dated Jun. 5, 2014, 13 pages.

(56) References Cited

OTHER PUBLICATIONS

Korean Office Action in related Korean Application 10-2013-7008849 dated Jun. 24, 2014, 12 pages.
Office Action issued Nov. 7, 2013 in related U.S. Appl. No. 13/228,075, 21 pages.
Artyomov et al., "Image Sensors in Security and Medical Applications". International Journal "Information Theories & Applications", vol. 14, 2007. pp. 114-127.
Kfouri et al, "Toward a Miniaturized Wireless Fluorescence-Based Diagnostic Imaging System". IEEE Journal of Selected Topics in Quantum Electronics, vol. 14, No. 1, Jan./Feb. 2008, pp. 226-234.
Written Opinion dated Oct. 24, 2014 in related International Application No. PCT/US2013/064070, 7 pages.
Patent Examination Report No. 1 dated Dec. 12, 2014 in related Australian application 2014200507, 5 pages.
Patent Examination Report No. 1 dated Dec. 8, 2014 in related Australian application 2014200513, 3 pages.
Patent Examination Report No. 1 dated Dec. 22, 2014 in related Australian application 2014200506, 3 pages.
Office Action dated Nov. 17, 2014 in related Chinese application 201180043228.3, 29 pages.
Office Action dated Jan. 2, 2015 in related U.S. Appl. No. 13/347,787, 17 pages.
Patent Examination Report No. 1 dated Dec. 18, 2014 in related Australian application 2014200505, 4 pages.
Response filed Sep. 27, 2013 to Office Action dated Jun. 27, 2013 in related U.S. Appl. No. 13/228,075, 17 pages.
Response filed Dec. 11, 2014 to Office Action dated Sep. 11, 2014 in related U.S. Appl. No. 13/228,075, 20 pages.
Response filed Sep. 5, 2014 to Office Action dated Jun. 5, 2014 in related U.S. Appl. No. 13/347,787, 21 pages.
Office Action dated Feb. 26, 2015 in related U.S. Appl. No. 14/036,549, 7 pages.
Office Action dated Feb. 26, 2015 in related U.S. Appl. No. 14/036,579, 9 pages.
International Preliminary Report on Patentability dated Feb. 16, 2015 in related International Application No. PCT/US2013/064070, 13 pages.
European Search Report dated Feb. 26, 2015 in related European Application 14188483.3, 7 pages.
Office Action dated Feb. 26, 2015 in related Korean Application No. 10-2013-7008849, 5 pages.
Office Action dated Mar. 26, 2015 in related U.S. Appl. No. 14/036,613, 9 pages.
Office Action dated Mar. 26, 2015 in related U.S. Appl. No. 13/228,075, 20 pages.
Office Action dated Mar. 5, 2015 in related U.S. Appl. No. 14/036,566, 15 pages.
Office Action dated Apr. 9, 2015 in related U.S. Appl. No. 14/036,592, 12 pages.
Office Action dated Jan. 29, 2015 in related Canadian Application No. 2,810,513, 5 pages.
Office Action dated Sep. 11, 2014 in related U.S. Appl. No. 13/228,075, 17 pages.
Written Opinion dated Oct. 24, 2014 in related International Application No. PCT/US2013/064070, 8 pages.
Patent Examination Report No. 2 dated May 18, 2015 in related Australian Application 2014200506, 4 pages.
Patent Examination Report No. 2 dated Apr. 23, 2015 in related Australian Application 2014200513, 3 pages.
Office Action issued Apr. 23, 2015 in related European Patent Application 11758634.7, 4 pages.
Office Action issued May 7, 2015 in related Japanese Patent Application 2014-102983, 10 pages.
Office Action issued Jul. 1, 2015 in related Chinese Patent Application 201180043228.3, 28 pages.
Office Action issued Jul. 30, 2015 in related U.S. Appl. No. 13/347,787, 14 pages.
Office Action issued May 1, 2015 in related Taiwanese Patent Application 102139872, 14 pages.
Office Action issued Aug. 13, 2015 in related U.S. Appl. No. 14/036,549, 9 pages.
Office Action issued Aug. 14, 2015 in related U.S. Appl. No. 14/036,579, 9 pages.
Office Action issued Aug. 26, 2015 in related U.S. Appl. No. 14/036,566, 14 pages.
Office Action dated Nov. 5, 2015 in related U.S. Appl. No. 13/228,075, 17 pages.
Office Action dated Sep. 11, 2015 in related U.S. Appl. No. 14/036,592, 11 pages.
Office Action dated Sep. 11, 2015 in related U.S. Appl. No. 14/036,613, 10 pages.
Office Action dated Dec. 17, 2015 in related Chinese Patent Application No. 201180043228.3, 12 pages.
Office Action dated Jan. 21, 2016 in related U.S. Appl. No. 13/347,787, 16 pages.
Office Action dated Feb. 24, 2016 in related U.S. Appl. No. 14/036,579, 12 pages.
Office Action dated Mar. 31, 2016 in related U.S. Appl. No. 14/036,566, 15 pages.
Office Action dated Apr. 11, 2016 in related U.S. Appl. No. 14/036,549, 10 pages.
Office Action dated Mar. 31, 2016 in related U.S. Appl. No. 14/036,613, 11 pages.
Office Action dated Apr. 18, 2016 in related U.S. Appl. No. 13/347,787, 7 pages.
Office Action dated Apr. 19, 2016 in related U.S. Appl. No. 14/036,592, 15 pages.
Office Action dated Apr. 22, 2016 in related U.S. Appl. No. 13/228,075, 17 pages.
Office Action dated Mar. 21, 2016 in related U.S. Appl. No. 14/036,566, 15 pages.
Office Action dated Apr. 21, 2016 in related European Application No. 14150398.7, 4 pages.
Office Action dated Apr. 21, 2016 in related European Application No. 14150399.5, 4 pages.
Office Action dated Apr. 21, 2016 in related European Application No. 14164448.4, 4 pages.
Office Action dated Apr. 21, 2016 in related European Application No. 14165017.6, 4 pages.
Office Action dated May 23, 2016 in related Japanese Application No. 2015-156944, 10 pages.
Patent Examination Report No. 1 dated May 25, 2016 in related Australian Application No. 2015252021, 3 pages.
Patent Examination Report No. 1 dated May 26, 2016 in related Australian Application No. 2015252022, 3 pages.
Patent Examination Report No. 1 dated May 3, 2016 in related Australian Application No. 2013338470, 3 pages.
Office Action dated Jun. 2, 2016 in related Japanese Application No. 2015-540682, 15 pages.
Office Action dated Jun. 14, 2016 in related Korean Application No. 10-2015-7014148, 13 pages.

* cited by examiner

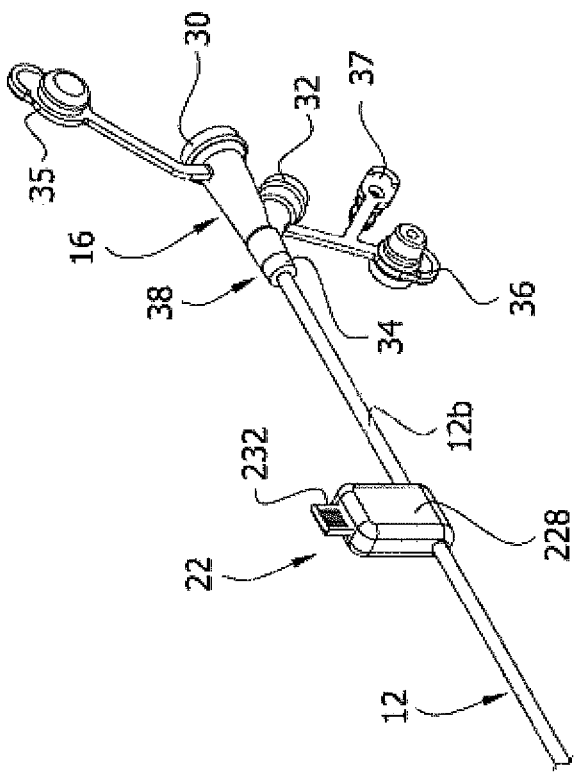
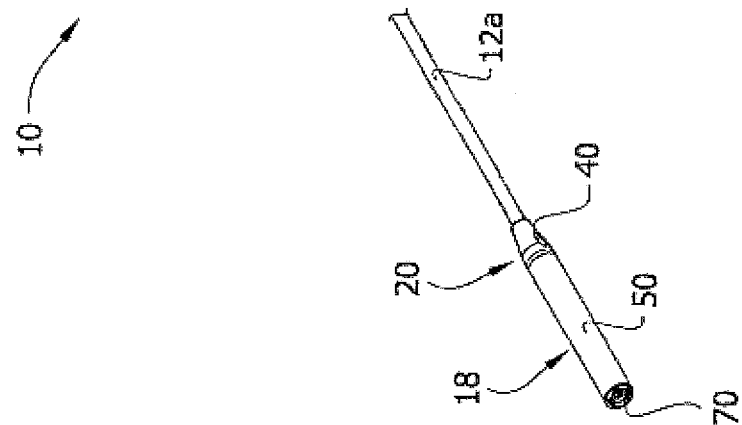
FIG. 1

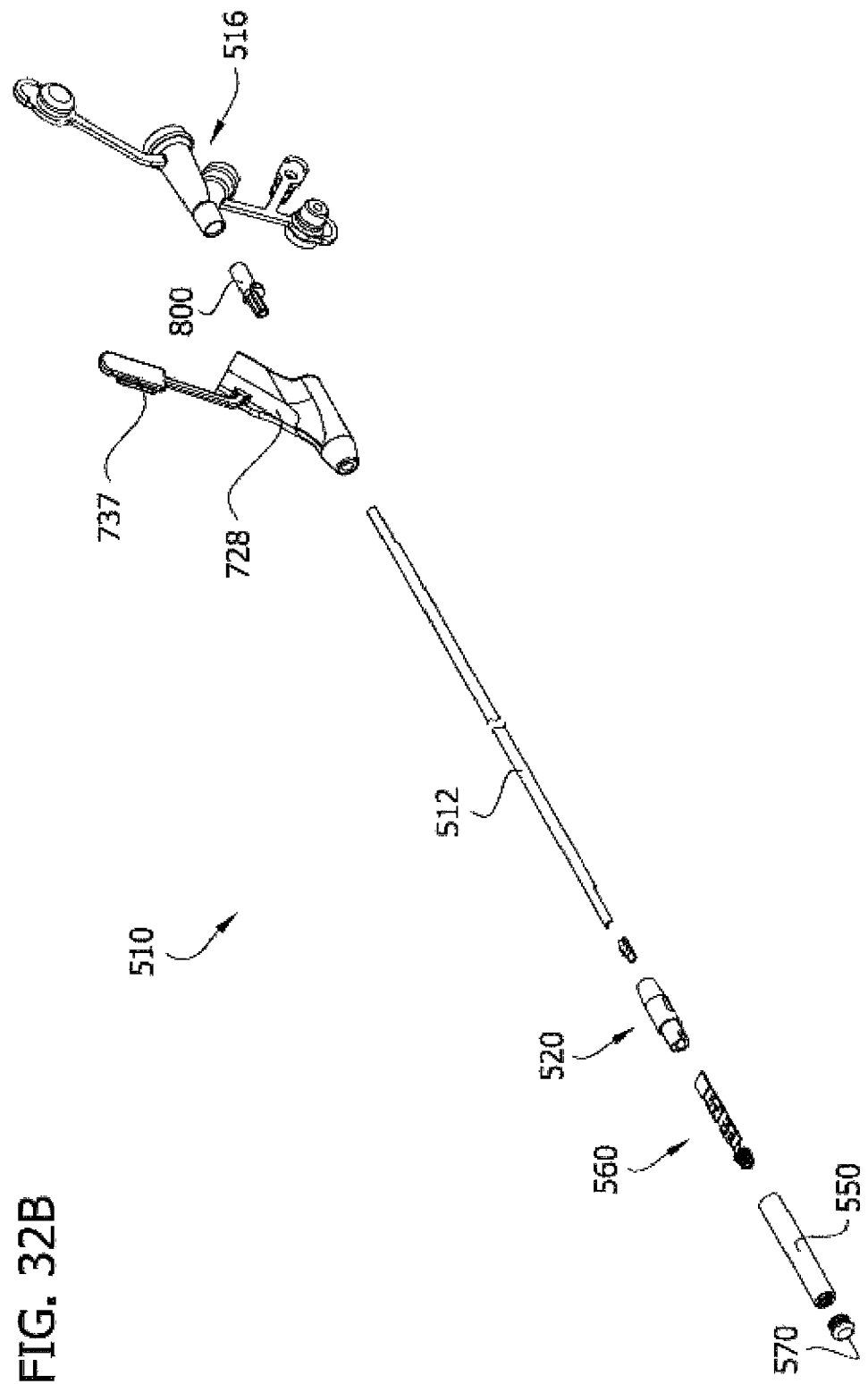

CATHETER WITH IMAGING ASSEMBLY AND CONSOLE WITH REFERENCE LIBRARY AND RELATED METHODS THEREFOR

CROSS-REFERENCE TO RELATED APPLICATIONS

This application is a continuation-in-part application of and claims the benefit under 35 U.S.C. §120 to co-pending U.S. patent application Ser. No. 13/228,075, titled CATHETER WITH IMAGING ASSEMBLY, filed Sep. 8, 2011, which claims the benefit under 35 U.S.C. §119 to U.S. Patent Application Nos. 61/482,080, filed May 3, 2011, and 61/380,985, filed Sep. 8, 2010, each of which is incorporated herein by reference in its entirety for all purposes.

BACKGROUND

The present invention relates to catheters and particularly to imaging catheter systems having displaying console with reference materials.

Several medical procedures involve positioning a catheter, such as a feeding tube or endoscope, within a patient through the patient's nose, mouth, or other opening. In many procedures, accurately positioning the catheter is crucial to the success of the procedure and/or to the safety of the patient. For example, a nasogastric (NG) feeding tube may be inserted through the nose, past the throat, and down into the stomach, or past the stomach into the small bowels of the patient to deliver food to the patient via the tube. If the feeding tube is mistakenly positioned in the patient's lung, the feeding solution would be delivered to the patient's lung causing critical and possibly fatal results.

Accordingly, x-ray imaging devices and procedures have been used to confirm accurate positioning of a feeding tube, or other type of catheter, within a patient. Specifically, x-ray images are taken of the patient after a feeding tube has been initially positioned within the patient. The x-ray images are examined to determine whether the feeding tube was properly positioned or whether re-positioning is necessary. The x-ray imaging procedure is repeated until feeding tube has been properly positioned. X-ray imaging procedures, however, are generally expensive and time consuming. Additionally, because a patient often uses a feeding tube for a substantial length of time, the x-ray imaging procedures must be repeated periodically to ensure that the feeding tube has not moved or migrated.

SUMMARY

One or more aspects of the invention can involve a catheter having an imaging assembly. In particular aspects of the invention, the catheter can be a feeding tube having an imaging assembly. In accordance with an aspect of the invention, an imaging catheter system can comprise an imaging catheter including an imaging assembly having an imaging device for generating imaging signals corresponding to images of anatomy of a patient. The imaging assembly transmits the imaging signals generated by the imaging device. The system also includes a console adapted to receive the imaging signals transmitted by the imaging assembly and present images generated from the imaging signals on a display. The console is adapted to selectively present a reference menu on the display including menu items. The menu items correspond to reference materials comprising any one or more of photographs, video recordings, audio recordings, diagrams, animations, and text. The materials provides information about any one or more of anatomy, patient preparation, imaging catheter preparation, imaging catheter placement, imaging catheter operation, imaging catheter features, console preparation, console operation, console features, system operation, system features, contact information, help information, and support information. The console can be further configured to present the reference menu simultaneously with the images generated from the imaging signals on the display. The console is typically configured to present a graphical user interface on the display. For some cases, the display is a touchscreen display adapted to present icons for control of the system by touching the display. The console, in further configurations, can be configured to present the reference materials simultaneously with the images generated from the imaging signals on the display. In still further cases, each of the reference materials is preferably located in a directory having a name corresponding to the corresponding reference material. The display can be adapted to present the reference menu when a user touches the display twice during a preselected period. The period can be, for example, within about one second. Further, at least a portion of the reference material is read-only and, in some cases, can be modified by updating system software. The imaging catheter system can comprise a feeding tube assembly including a feeding tube for delivering enteral feeding liquid to the patient, the tube having an inlet and an outlet and a feeding passage extending between said inlet and said outlet, the imaging catheter being positioned adjacent the outlet for generating imaging signals corresponding to an alimentary canal of the patient, the imaging assembly being sealed from the feeding passage to inhibit enteral feeding liquid in the feeding passage from entering the imaging assembly. The system typically further comprises an interface cable connecting the imaging catheter to the console for use in transmitting the imaging signals generated by the imaging device to the console.

One or more aspects of the invention can be directed to an imaging catheter system, comprising a feeding tube having an inlet connectable to a source of feeding fluid, an outlet distal from and fluidly connected to the inlet through a feeding passage, and an imaging device disposed proximate the outlet, the imaging device configured to generate and transmit imaging signals corresponding to an image of an anatomy of a patient; and a console comprising a display and memory having stored therein a plurality of reference materials selected from the group consisting of photographs, video recordings, audio recordings, diagrams, animations, text, and combinations thereof. In some cases, each of the plurality of reference materials can provide information about at least one of anatomy, patient preparation, imaging catheter preparation, imaging catheter placement, imaging catheter operation, imaging catheter features, console preparation, console operation, console features, system operation, system features, and contact information. Preferably, the console is configured to receive the imaging signals, present at least a portion of at least one image corresponding to the imaging signals on the display, and present a reference menu on the display including menu items corresponding to at least one of the reference materials. The at least one of the plurality of reference materials can include a photograph showing an anatomical landmark. The anatomical landmark can be one of a bronchus, larynx, a tracheal ring, cardia, pyloric sphincter or pylorus, cricoid cartilage, bronchial split, esophageal junction, stomach folds, duodenal folds, and a pyloric orifice.

In accordance with another aspect of the invention, a method of operating a medical system having a medical instrument including an imaging device for generating imaging signals corresponding to images of anatomy of a patient and a console adapted to present images generated from the imaging signals on a display comprises accessing reference material on the display. The material includes an image of exemplary anatomy indicative of proper placement of the medical instrument in the patient.

One or more aspects of the invention can be directed to a method of facilitating use of a feeding tube assembly. In one or more embodiments in accordance with such aspects of the invention, the method can comprise providing a feeding tube having an inlet connectable to a source of feeding fluid, an outlet distal from and fluidly connected to the inlet through a feeding passage, and an imaging device disposed proximate the outlet, the imaging device configured to generate and transmit imaging signals corresponding to an image of an anatomy of a patient; and providing a console comprising a display and memory having stored therein a plurality of reference materials selected from the group consisting of audiovisual data such as videos, audio, and photographs, textual data such as diagrams, animations, and text, and combinations thereof. In accordance with some particular embodiments, each of said reference material can provide information about at least one of anatomy, patient preparation, imaging catheter preparation, imaging catheter placement, imaging catheter operation, imaging catheter features, console preparation, console operation, console features, system operation, system features, and contact information. In some cases, the console can be configured to receive the imaging signals, present at least a portion of at least one image corresponding to at least a portion of the imaging signals on the display, and present a reference menu on the display including menu items corresponding to at least one of the reference materials. In some cases, the console can be configured to simultaneously present on the display a photograph from the plurality of reference materials and a video image corresponding to the image signals from the imaging assembly, wherein the photograph provides a representative anatomical marker. The method, in accordance with further aspects of the invention, can comprise at least one of storing additional reference materials into the memory, removing at least one of the reference materials from the memory, and replacing the memory with an updated memory, the updated memory having stored therein an updated reference material. The method, in accordance with other further cases, can comprise receiving the console from a user; and after receiving the console, at least one of storing additional reference materials into the memory, removing at least one reference materials from the memory, and replacing the memory with an updated memory, the updated memory having stored therein at least one updated reference material.

In one aspect, an imaging catheter system generally comprises an imaging catheter and a console. The imaging catheter includes an elongate body having opposite first and second ends. An imaging assembly is at the first end of the elongate body and includes an imaging device for generating imaging signals indicative of images of anatomy of a subject. The imaging assembly is adapted to transmit the imaging signals generated by the imaging device. An electronic memory component has a predefined identifier of the imaging catheter written thereon. The console includes a display. The console is configured for receiving the imaging signals from the imaging assembly and displaying images generated from the imaging signals on the display. The console is configured to read the predefined identifier from the electronic memory component.

BRIEF DESCRIPTION OF THE DRAWINGS

FIG. 1 is a schematic illustration showing a perspective view of an imaging feeding tube assembly, in accordance with one or more aspects of the invention;

FIG. 32B is a schematic illustration showing an exploded perspective of the imaging feeding tube assembly in FIG. 32A, in accordance with one or more aspects of the invention;

Corresponding reference characters indicate corresponding parts throughout the drawings.

DETAILED DESCRIPTION

Figure 2:
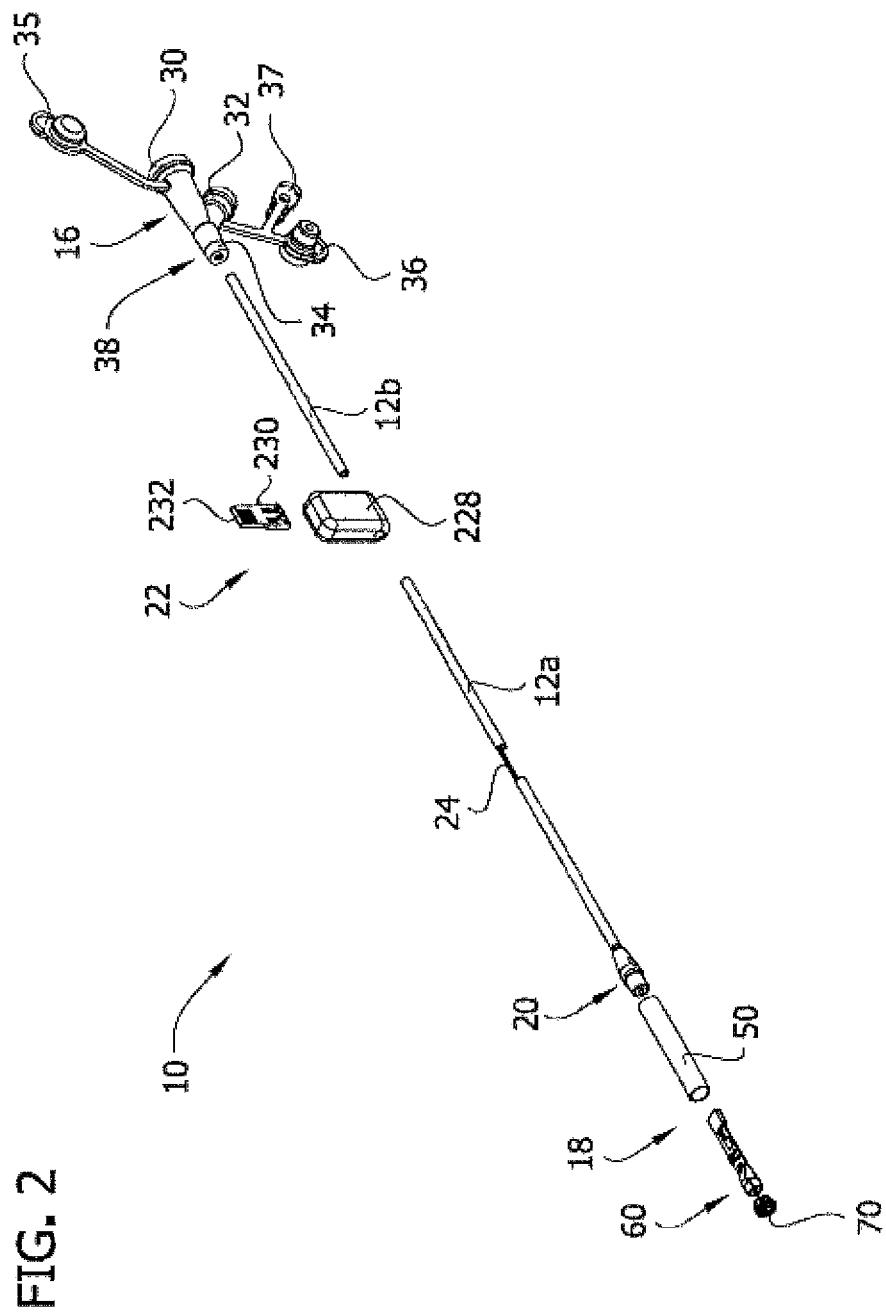
FIG. 2 is schematic illustration showing a perspective view of the feeding tube assembly in FIG. 1, in accordance with one or more aspects of the invention.

In another aspect, a feeding tube assembly generally comprises a flexible feeding tube having opposite first and second longitudinal ends, a longitudinal axis extending between the first and second longitudinal ends, and a feeding passage defined therein extending along the longitudinal axis between the first and second longitudinal ends. An inlet adaptor is adjacent the second longitudinal end of the tube in fluid communication with the feeding passage. The inlet adaptor is configured for fluid connection to a source of enteral feeding liquid to fluidly connect the source of enteral feeding liquid to the feeding passage. An imaging assembly includes an imaging device. The imaging assembly is configured for generating and transmitting imaging signals indicative of images of the alimentary canal of a subject. The imaging assembly is secured to the tube adjacent the first longitudinal end of the tube and is sealed from the feeding passage to inhibit enteral feeding liquid in the feeding passage from entering the imaging assembly. A feeding outlet is proximate the imaging assembly and in fluid communication with the feeding passage for delivering enteral feeding liquid to the subject. A console connector is communicatively connected to the imaging assembly, the console connector configured for use in communicatively connecting the imaging assembly to a console to allow transmission of the imaging signals to the console.

In yet another aspect, a feeding tube system generally comprises a feeding tube assembly and a console. The feeding tube assembly includes a feeding tube having opposite first and second ends and a feeding passage fluidly connecting the first and second ends. An inlet adaptor is adjacent the second end of the tube in fluid communication with the feeding passage. The inlet adaptor is configured for fluid connection to a source of enteral feeding liquid to fluidly connect the source of enteral feeding liquid to the feeding passage. An imaging assembly including an imaging device and configured for generating and transmitting imaging signals indicative of images of the alimentary canal of a subject can be utilized. The imaging assembly is secured to the tube adjacent the first end of the tube and is sealed from the feeding passage to inhibit enteral feeding liquid in the feeding passage from entering the imaging assembly. A feeding outlet is intermediate the inlet adaptor and the imaging assembly and in fluid communication with the feeding passage for delivering enteral feeding liquid to the subject. The console includes a display, and is operatively coupled to the feeding tube assembly and configured for receiving imaging signals transmitted by the imaging assembly and displaying images generated from the imaging signals on the display.

In another embodiment, a feeding tube assembly generally comprises a flexible feeding tube having opposite first and second longitudinal ends, and a feeding passage defined therein extending between the first and second ends. An inlet adaptor is adjacent the second longitudinal end of the tube in fluid communication with the feeding passage. The inlet adaptor is configured for fluid connection to a source of enteral feeding liquid. An imaging assembly includes an imaging device for generating imaging signals indicative of images of the alimentary canal of a subject. The imaging assembly is secured to the feeding tube adjacent the first end of the tube and is fluidly isolated from feeding passage. A console connector is secured to the feeding tube proximate the inlet adaptor. The console connector is communicatively connected to the imaging assembly, and configured for use in connecting to the imaging assembly to a console to allow transmission of the imaging signals to the console.

In yet another embodiment, an imaging catheter assembly generally comprises an elongate body having a first body end, and an opposite a second body end; and an imaging assembly secured to the first body end. The imaging assembly has a first imaging assembly end remote from the first body end, a second imaging assembly end adjacent the first body end, and an imaging assembly longitudinal axis extending between the first and second imaging assembly ends. The imaging assembly includes a rigid-flex circuit having an electronic component-mounting portion extending along the imaging assembly longitudinal axis from adjacent the second imaging assembly end toward the first imaging assembly end, and a camera-mounting portion adjacent the first imaging assembly end and extending generally transverse to the imaging assembly. The electronic component-mounting portion includes longitudinally spaced first and second rigid sections and a first flexible section disposed between the first and second rigid sections. A first electronic component is mounted on the first rigid section of the electronic component-mounting portion. A second electronic component is mounted on the second rigid section of the electronic component-mounting portion. A camera is mounted on the camera-mounting portion, and the camera is communicatively connected to the first and second electronic components. The rigid-flex circuit is disposed in a housing. The housing circumferentially surrounds at least a portion of the rigid-flex circuit. The first flexible section of the electronic component-mounting portion is free from electronic components mounted thereon such that the rigid-flex circuit is capable of bending at the first flexible section.

In another aspect, an imaging catheter system for use in performing a medical procedure generally comprises an imaging catheter and a console. The imaging catheter includes an elongate body having opposite first and second ends. An imaging assembly at the first end of the body is adapted to be inserted into a subject. The imaging assembly includes an imaging device for generating imaging signals representative of images of anatomy of the subject when the imaging assembly is inserted in the subject. The imaging assembly is adapted to transmit the imaging signals generated by the imaging device. The imaging catheter includes an electronic memory component. The console including a display, and is configured for receiving the imaging signals transmitted by the imaging assembly and displaying images generated from the imaging signals on the display. The console is configured to write data to the electronic memory component during use of the imaging catheter.

In another aspect, an imaging catheter system for use in performing a medical procedure generally comprises an imaging catheter and a console. The imaging catheter includes an elongate body having opposite first and second ends. An imaging assembly at the first end of the body is adapted to be inserted into a subject. The imaging assembly includes an imaging device for generating imaging signals representative of images of anatomy of the subject when the imaging assembly is inserted in the subject. The imaging assembly is adapted to transmit the imaging signals generated by the imaging device. The console includes a display. The console is configured for receiving the imaging signals transmitted by the imaging assembly and displaying images generated from the imaging signals on the display. The console is configured to simultaneously present an image previously received by the console from the imaging assembly and a current image from image data currently being received by the console from the imaging assembly.

Figure 3:
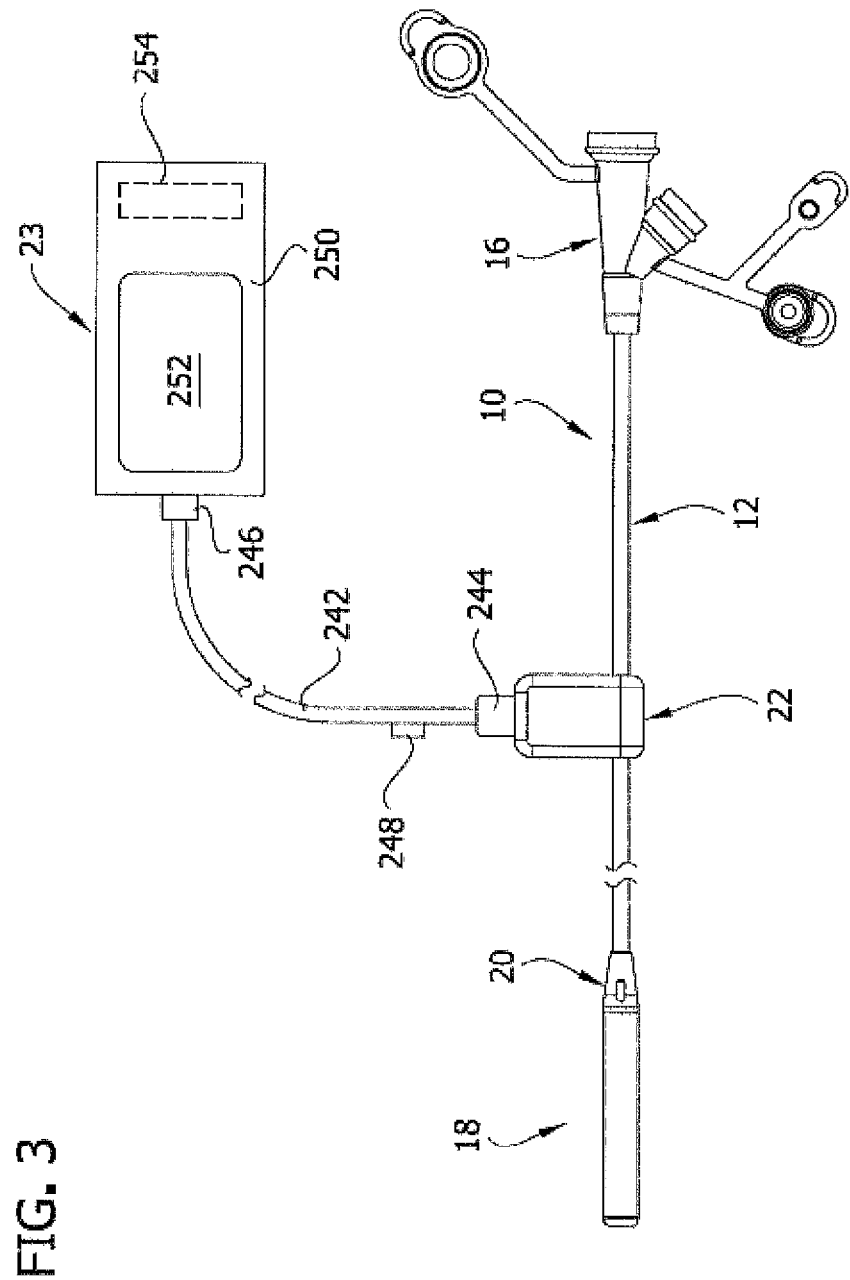
FIG. 3 is a schematic illustration showing a side, elevational view of an imaging feeding tube system, including the imaging feeding tube assembly in FIG. 1, and interface cable, and a console, in accordance with one or more aspects of the invention.

Referring now to the drawings and in particular to FIGS. 1-3, an imaging catheter is generally indicated at 10. As disclosed herein, the imaging catheter can be a medical device that is configured for insertion into a subject, e.g., a human or a non-human subject, and configured to provide images, e.g., digital video, of anatomy of the subject as the medical device is inserted into the subject and/or after the medical device is positioned in the subject. In the illustrated embodiment, the imaging catheter is configured as a feeding tube assembly 10 and exemplarily illustrated as a nasogastric feeding tube assembly. The nasogastric feeding tube assembly 10 can be configured to provide digital images of an alimentary canal, or portions thereof, of the subject as the feeding tube assembly is inserted into the subject and after the feeding tube assembly is positioned in the subject to facilitate confirmation of proper placement of the feeding tube assembly in the subject. The nasogastric feeding tube assembly 10 can be also configured to deliver liquid nutrients into the alimentary canal of the subject by enteral feeding, such as after a user, e.g., a medical practitioner, confirms proper placement of the feeding tube assembly in the subject, by viewing the acquired digital images from the imaging feeding tube assembly. It is understood that the imaging catheter 10 may be configured as a different type of feeding tube, such as a gastric feeding tube, or a jejunostomy feeding tube, or may be configured as a different type of medical device, such as an endoscope, or a heart catheter, e.g., a balloon catheter or a heart catheter.

The illustrated feeding tube assembly 10 generally includes an elongate, generally flexible body in the form of a feeding tube, generally indicated at 12, having a longitudinal axis A (FIG. 6), an open first longitudinal end, or a distal end, and an open second longitudinal end, or a proximal end. A feeding passage 14 (FIGS. 4-6), defined by an interior surface of the feeding tube 12, extends longitudinally between the longitudinal ends of the tube for delivering nutrients, e.g., in the form of an enteral feeding solution to the subject. In other embodiments—such as catheters that are not feeding tubes—the elongate body may have other configurations, and may not have a longitudinal passage for delivering fluids to the patient. An inlet adapter, generally indicated at 16, for delivering liquid nutrients into the feeding passage 14 is attached to the second end of the tube, and an imaging assembly, generally indicated at 18, for generating and transmitting real time images, e.g., live video, of the alimentary canal of the patient during and/or following intubation is attached to the first end of the tube 12 by an imaging assembly connector, generally indicated at 20. As used herein with the point of reference being the feeding source, the inlet adaptor 16 defines the proximal end of the feeding tube assembly 10, and the imaging assembly 18 defines the distal end. The feeding tube assembly 10 also can include a console connector, generally indicated at 22, in communication with the imaging assembly 18, to provide communication between the imaging assembly and a console 23 (FIG. 3), on which the images obtained by the imaging assembly 18 may be displayed, as described in detail herein. In the illustrated embodiment, the feeding tube assembly 10, the console 23, and an interface cable 242, which communicatively connects the feeding tube assembly to the console, together constitutes an imaging catheter system, and more specifically, an imaging feeding tube system.

Referring to FIGS. 1-4, the exemplarily illustrated feeding tube 12 comprises two tube segments: a first tube segment 12a extending between the imaging assembly connector 20 and the console connector 22, and a second tube segment 12b extending between the console connector and the inlet adaptor 16. As disclosed in more detail below, the first and second tube segments 12a, 12b can be secured to the console connector 22 in such a way that the first and second tube segments are in fluid communication with each other to at least partially define the feeding passage 14. In other embodiments of the invention, the tube 12 may be formed as an integral, one-piece component.

The tube 12 may comprise indicia such as graduations (not shown) that show or providing a relative indication of insertion depth to facilitate proper intubation. In one example, the tube 12 may have a length between about 36 inches and about 55 inches, although it may be of other lengths without departing from the scope of the invention.

Figure 6:
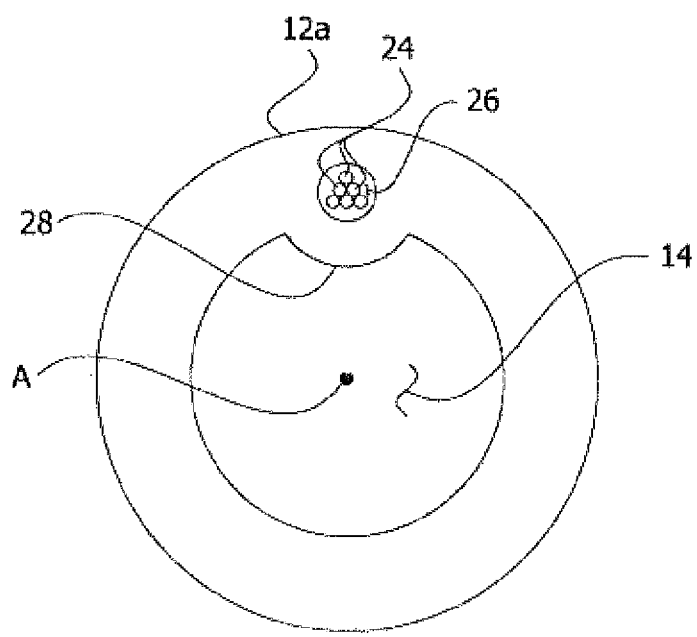
FIG. 6 is a schematic illustration showing an enlarged cross section view of the feeding tube of the feeding tube assembly in FIG. 1, in accordance with one or more aspects of the invention.

As shown in FIG. 6, the first tube segment 12a typically includes one or more electrical conductors 24 (broadly, a signal-transmitting component) typically disposed in the tube wall of the first tube segment. The second tube segment 12b may be free from such electrical conductors. The electrical conductors 24 of the first tube segment 12a run longitudinally along the first tube segment, such as along or parallel a longitudinal axis of the feeding passage 14. At least some of the electrical conductors 24 can be configured to transmit imaging signals between the imaging assembly 18 and the console 23, such as through the console connector 22 and the interface cable 242. Other electrical conductors 24 may be configured to transmit power from the console 23 to the imaging assembly 18, and provide a ground. Still other electrical conductors 24 may be configured to provide other communication including, but not limited to, two-way communication, between the console 23 and the imaging assembly 18. The first tube segment 12a may include a different type of a signal-transmitting component, such as fiber-optic cables or other signal-transmitting components, to effect transmission of signals between the imaging assembly 18 and the console connector 22. In one or more embodiments of the invention, at least one of the electrical conductors 24 is configured to supply power from a power supply, which can be the console 23, to the imaging assembly 18, although other ways of powering the imaging assembly, including the imaging assembly having its own source of power, do not depart from the scope of the present invention.

Figure 5:
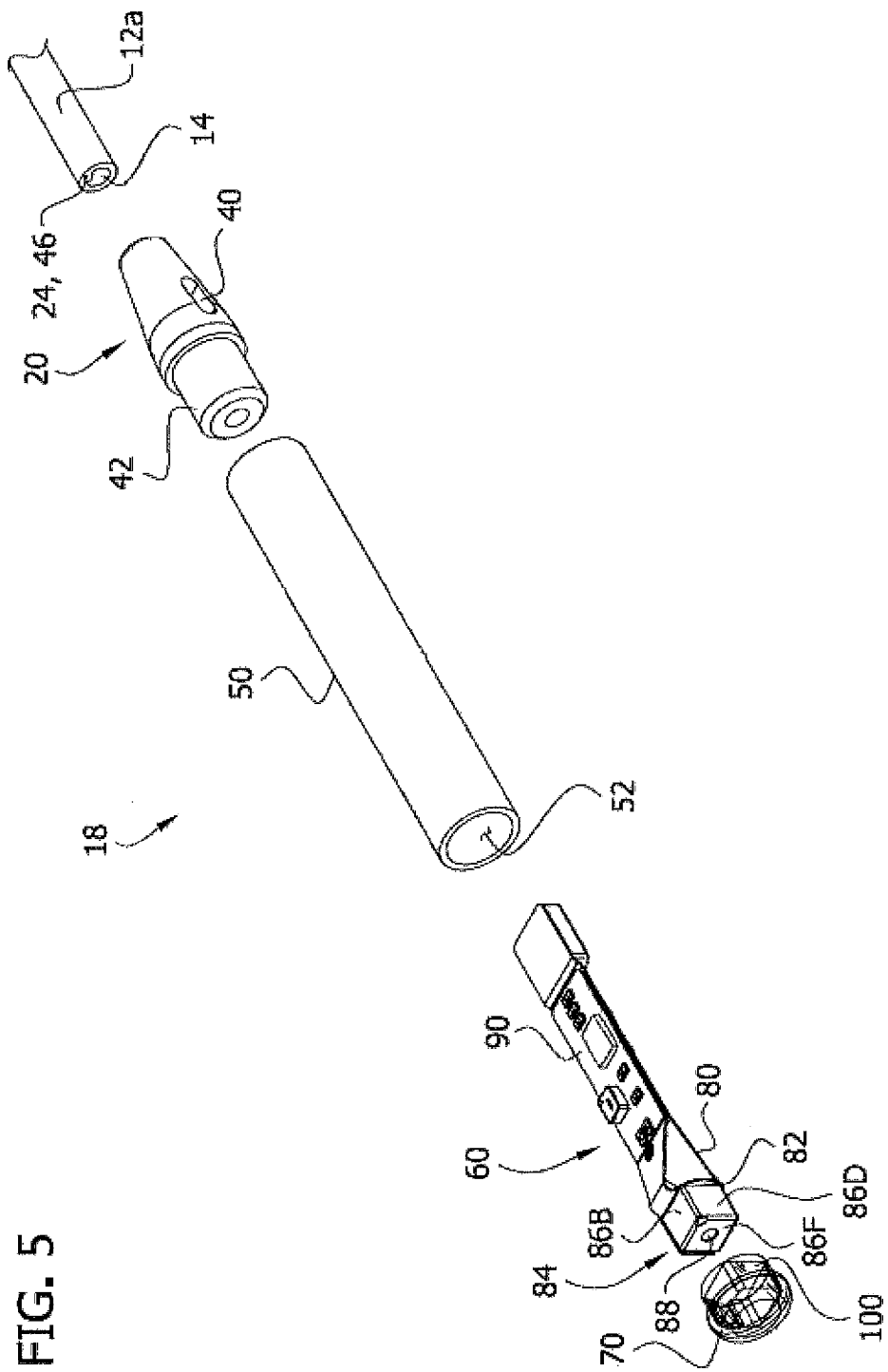
FIG. 5 is a schematic illustration showing an enlarged, fragmentary, perspective view of a distal end portion of the feeding tube assembly in FIG. 1, including an exploded imaging assembly, an imaging assembly connector, and a portion of the feeding tube, in accordance with one or more aspects of the invention.

As exemplarily illustrated, the electrical conductors 24 can be disposed within a conductor passage 26 of the feeding tube 12 so that the conductors are physically separated or at least fluidly isolated from the feeding passage 14 to inhibit or reduce the likelihood of feeding solution in the feeding passage from contacting the conductors. As shown in FIG. 6, the interior surface defining a portion of the feeding passage 14 in the first tube segment 12a has a generally circular cross section having an arcuate portion 28 extending inwardly and running longitudinally along a lengthwise dimension of the feeding tube assembly or segment. The electrical conductors 24 can be disposed within the tube wall of the first tube segment 12a between the arcuate portion 28 of the interior surface and the exterior surface of the tube segment which provides a configuration that allows physical separation between the electrical conductors 24 and the enteral feeding solution in the feeding passage 14, as disclosed above, and can maximize the area or volume of the feeding passage. A longitudinal axis A passes through the feeding passage 14. As such, this configuration promotes the flow of fluid in the feeding passage 14 and reduces the likelihood of occlusions in the feeding passage. A substantially uniform wall thickness around passage 14, as shown in FIG. 5, can decrease the amount of material entrapment that may occur, or at least can reduce the likelihood of formation of occlusions. It is understood that the first tube segment 12a may be of other configurations without departing from the scope of the present invention.

The feeding tube 12, including, for example, the first and second tube segments 12a, 12b, may be formed from a thermoplastic polyurethane polymer, such as but not limited to, an aromatic, polyether-based thermoplastic polyurethane, and a radiopaque substance, such as barium. The first and second tube segments 12a, 12b may be formed by an extrusion process. The tube 12 may be formed from other materials and may be formed in other ways without departing from the scope of the present invention. In one non-limiting example, the electrical conductors 24 or other signal-transmitting components may be co-extruded with the first tube segment 12a to embed the conductors in the first tube segment. In another example, the conductors 24 or other signal-transmitting components may be fed through the conductor passage 26 after forming the first tube segment 12a. Introducing any of the one or more conductors 12 can be facilitated by, for example, internally pressurizing passage 26 with a fluid prior to insertion therein. Other ways of forming the first tube segment 12a and/or the tube 12 do not depart from the scope of the present invention.

Referring back further to FIGS. 1 and 2, the illustrated inlet adaptor 16 typically includes first and second inlet ports 30, 32, respectively, in fluid communication with a single outlet port 34. The exemplarily illustrated inlet adaptor 16 may be referred to as a Y-port. The first inlet port 30 may be used for connection to a source of liquid nutrients, such as an enteral feeding solution. For example, a barbed connector (not shown), in fluid communication with the source of an enteral feeding solution, may be inserted into the first inlet port 30 and secured therein by a friction-fit. Thus, an aspect of the present invention may involve configurations with the feeding fluid in fluid communication with the feeding tube assembly. An optional cap 35 tethered on the inlet adaptor 16 can be removably receivable in the first inlet port 30 to close the inlet port when it is not being used. The second inlet port 32 may be used for connection to a source of medicine. Optional tethered first and second caps 36, 37, respectively, can be used to variably configure the second inlet port 32 as a connection or port to various or different connectors typically used with various sources of medicine. For example, the first cap 36 can be removably receivable in the second inlet port 32, providing a central opening therethrough that is sized and shaped to mate with a catheter syringe. The second cap 37 can be removably receivable in the central opening in the first cap 36, thereby providing a central opening that is sized and shaped to particularly mate with a tip of an oral syringe. The inlet adaptor 16 may have other shapes, sizes and configurations, or may be entirely omitted, without departing from the scope of the invention.

The inlet adaptor 16 can be secured to the second or proximal end of the tube 12 at an adaptor weld, generally indicated at 38, so that the outlet port 34 of the adaptor 16 is in sealed fluid communication with the feeding passage 14 of the feeding tube. The adaptor weld 38 typically tapers distally from the adaptor 16 to the tube 12 so that the weld has a smooth, generally continuously decreasing diameter. It is to be understood that the adaptor 16 may be secured to the tube 12 in other ways without departing from the scope of the invention. For example, the inlet adaptor 16 may be secured to the tube 12 by solvent bonding, or other securement techniques. The adaptor 16 may be composed of the same material as the feeding tube 12, or a blend of materials, or a different but compatible material. In one example, the adaptor 16 is composed of blend of polyvinyl chloride and polyurethane elastomer. In another example, the adaptor 16 is composed of an aromatic, polyether-based thermoplastic polyurethane or DEHP-free PVC. The adaptor 16 may be formed from other types of materials within the scope of the invention.

Referring to FIGS. 1, 2, and 5, the imaging assembly connector 20 can have a first end margin, such as a distal end margin, secured to the imaging assembly 18, and a second end margin, such as a proximal end margin, secured to the first end margin of the first tube segment 12a. The imaging assembly connector 20 typically defines a feeding outlet 40 that is in fluid communication with the feeding passage 14 of the tube 12. The feeding outlet 40 can comprise one or more openings extending laterally through a side of the imaging assembly connector 20 (only one such lateral opening is illustrated). In the illustrated embodiment, the first or distal end of the tube 12 is received and secured within the imaging assembly connector 20 at the second or proximal end of the imaging assembly connector to provide fluid communication between the feeding passage 14 and the feeding outlet 40. The imaging assembly connector 20 can be closed adjacent the first or distal end to prevent the feeding solution in the feeding passage 14 from entering the imaging assembly 18. Thus, the imaging assembly 18 is typically sealed off from and not in fluid communication with the feeding passage 14. Instead, the feeding solution typically flows laterally out from the outlet 40 relative to the feeding tube 12. When the feeding tube assembly 10 is determined to be appropriately positioned in a patient, feeding solution or other desirable liquid fed into the inlet adaptor 16 can be introduced through the feeding passage 14 of the tube 12, and out through the outlet 40 and into the subject's alimentary canal. As illustrated in FIG. 5, the first end margin of the imaging assembly connector 20 can have a connection portion 42 shaped and sized to fit in the imaging assembly 18. The imaging assembly connector 20 may be formed integrally with the imaging assembly 18 or may be omitted, without departing from the scope of the present invention.

The electrical conductors 24 may be embedded or otherwise received in the wall of the imaging assembly connector 20 so that the conductors are sealed from the feeding outlet 40 and the feeding passage 14 to inhibit feeding solution from contacting the conductors. In one embodiment, the imaging assembly connector 20 may include two distinct parts that are assembled together. The first part may define the feeding outlet 40 that receives liquid from the tube 12, as described above, and a conductor passage (not shown) that is separate and apart from the feeding passage outlet. The second part may define the connection portion 42 and a conductor passage extending to a conductor passage in the first part to facilitate connection of or carry the electrical conductors 24 between the imaging assembly 18 and the tube 12. The imaging assembly connector 20 may be omitted or may have other shapes, sizes, and configurations. Moreover, the imaging assembly 18 may be secured to the tube 12 in other ways without departing from the scope of the present invention.

In one example, the imaging assembly connector 20 may be injection molded onto the end of the feeding tube 12. The direct connection of the imaging assembly connector 20 to the feeding tube provides strain relief for the electrical conductors 24 extending out of the end of the feeding tube 12 to the imaging assembly.

Referring to FIG. 5, the imaging assembly 18 can include a tubular housing 50, a flexible circuit ("flex circuit") assembly 60 disposed within the tubular housing, and a transparent or translucent cap 70 secured to the tubular housing 50. A flex circuit typically includes a deformable circuit element and components mounted on the deformable circuit element. The deformable circuit element may be a flat substrate, at least prior to being deformed, that can be bent or otherwise deformed, and which includes electrical conductors for making electrical connection among various components that may be mounted on the substrate. The deformable circuit element may only be partially deformable, e.g., only at discrete bend lines, within the scope of the present invention. Among other functions, the tubular housing 50 can provide protection for the flex circuit assembly 60, and the housing may be waterproof to inhibit the ingress of liquid into the imaging assembly 18. The tubular housing 50 has an interior surface defining an axial passage 52 shaped and sized for housing the flex circuit assembly 60 in a folded configuration. In one embodiment, the tubular housing 50 is formed from a generally flexible material that provides protection for the flex circuit assembly 60 and allows the imaging assembly 18 to bend to facilitate maneuverability of the feeding tube assembly 10. A second end, such as a proximal end, of the tubular housing 50 can be configured to receive the connection portion 42 of the imaging assembly connector 20, and can be adhered thereto to secure the imaging assembly to feeding tube 12. The tubular housing 50 may be generally opaque, by being formed from an opaque white material or having an opaque material applied thereon, to reflect illumination from a light source, such as an internal LED 96, and direct the illumination outward from the distal end of the imaging assembly 18 to, for example, a field of view.

The flex circuit assembly 60 typically includes a flex circuit 80 and electronic components (not labeled), described below, attached thereto. In the partially assembled or folded configuration exemplarily shown in FIGS. 5, 7, and 8, the flex circuit assembly 60 can have a length with a first longitudinal end, e.g., a distal end, and an opposite second longitudinal end, e.g., a proximal end. The electrical conductors 24 can be connected to the second longitudinal end, e.g., the proximal end, of the flex circuit assembly 60. A camera-mounting portion 82 is typically disposed at the first longitudinal end, e.g., the distal end of the flex circuit assembly 60. An imaging device such as a digital camera, generally indicated at 84, can be mounted on the camera-mounting portion 82. The camera 84 can have a cuboidal shaped housing 86 with a base 86A, as shown in FIG. 8, sides 86B, 86C, 86D, 86E, and an upper or first surface 86F. The upper surface 86F of the camera 84 can include a lens 88. The lens 88 defines a field of view that projects generally outward from the distal end of the imaging assembly 18. In accordance with one or more embodiments of the invention, the camera 84 comprises an imaging device, such as a CMOS imaging device. In further embodiments of the invention, the camera 84 may comprise a different type of solid state imaging device, such as a charge-coupled device (CCD), or another type of imaging device. Other ways of configuring the electronics and other components of the imaging assembly 18 do not depart from the scope of the present invention and may be implemented as variant embodiments. For example, in another embodiment, the flex circuit assembly 60 may be replaced with a rigid printed circuit board (PCB).

The flex circuit assembly 60 can include a power-mounting portion 90 (FIGS. 5 and 7) and a control or data-mounting portion 92 (FIG. 8) each typically extending from the camera-mounting portion 82 at a fold line toward the first longitudinal end of the flex circuit assembly 60. As will be described in further detail, power supply components are typically disposed on the power-mounting portion 90, and camera control components are typically disposed on the data-mounting portion 92.

Figure 7:
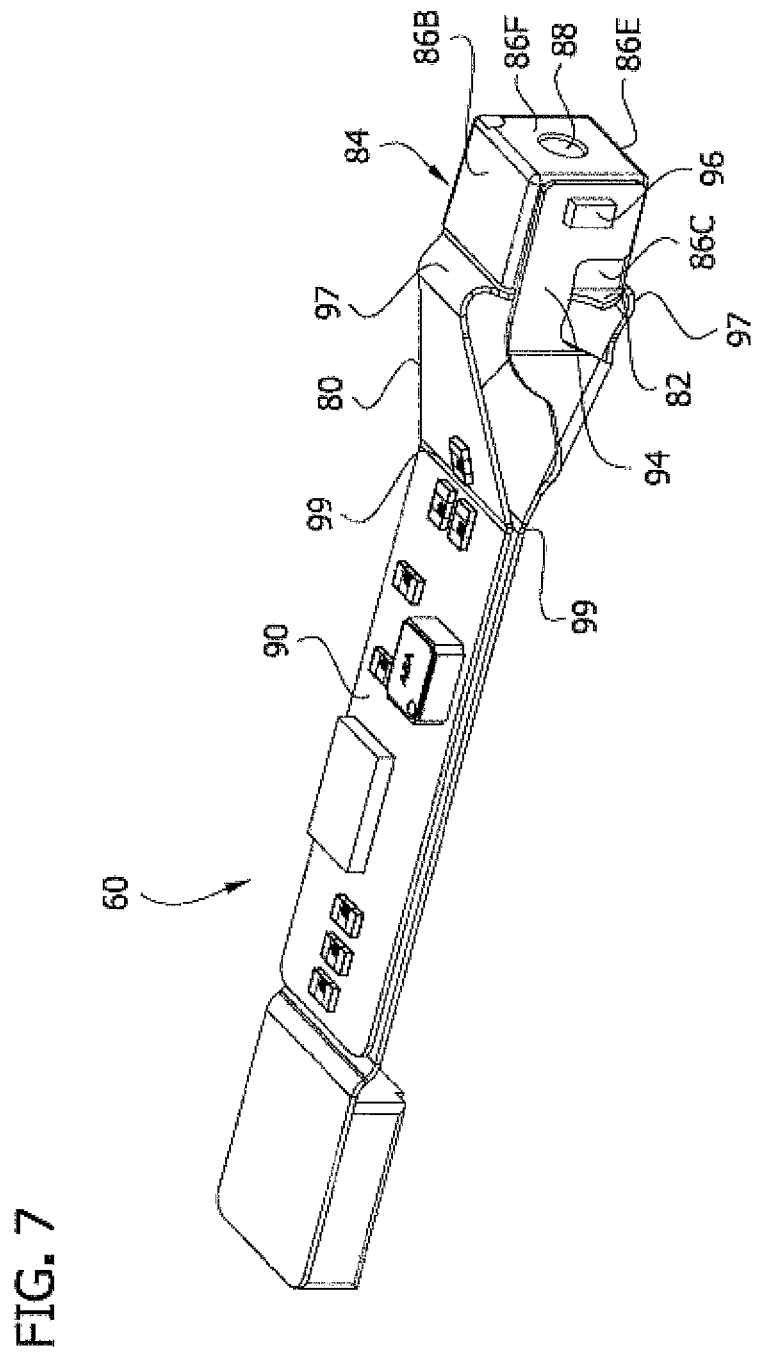
FIG. 7 is a schematic illustration showing atop perspective view of a flex circuit assembly of the imaging assembly in FIG. 5, in a folded configuration, in accordance with one or more aspects of the invention.
Figure 8:
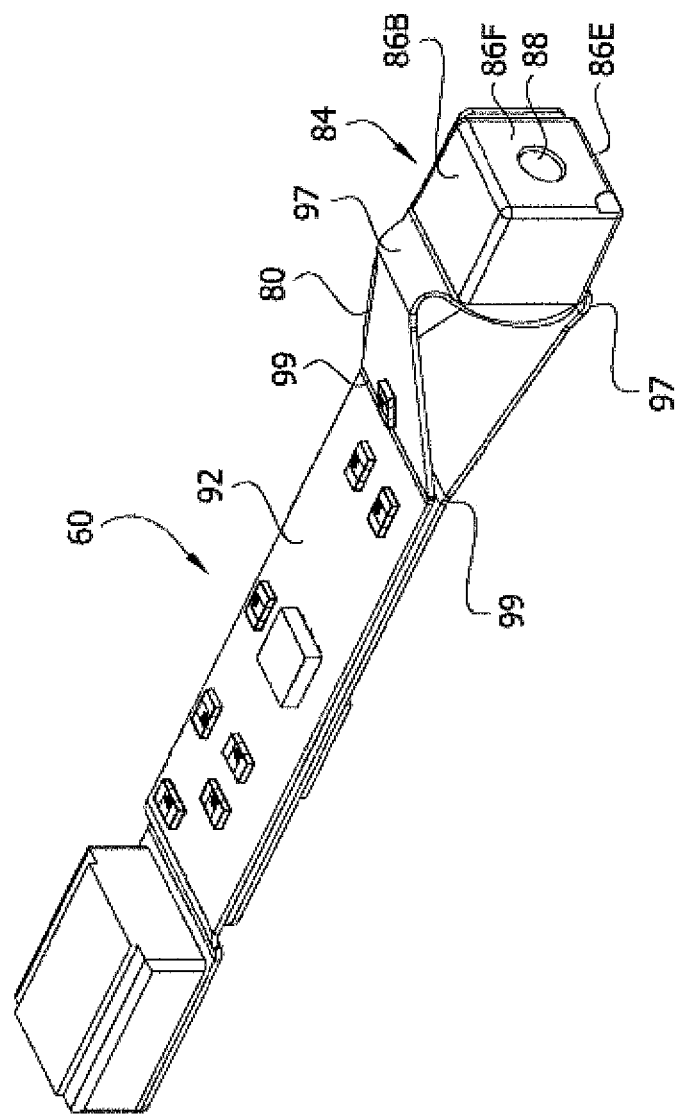
FIG. 8 is a schematic illustration showing a bottom perspective view of the flex circuit assembly of the imaging assembly in FIG. 4, in the folded configuration, in accordance with one or more aspects of the invention.
Figure 9:
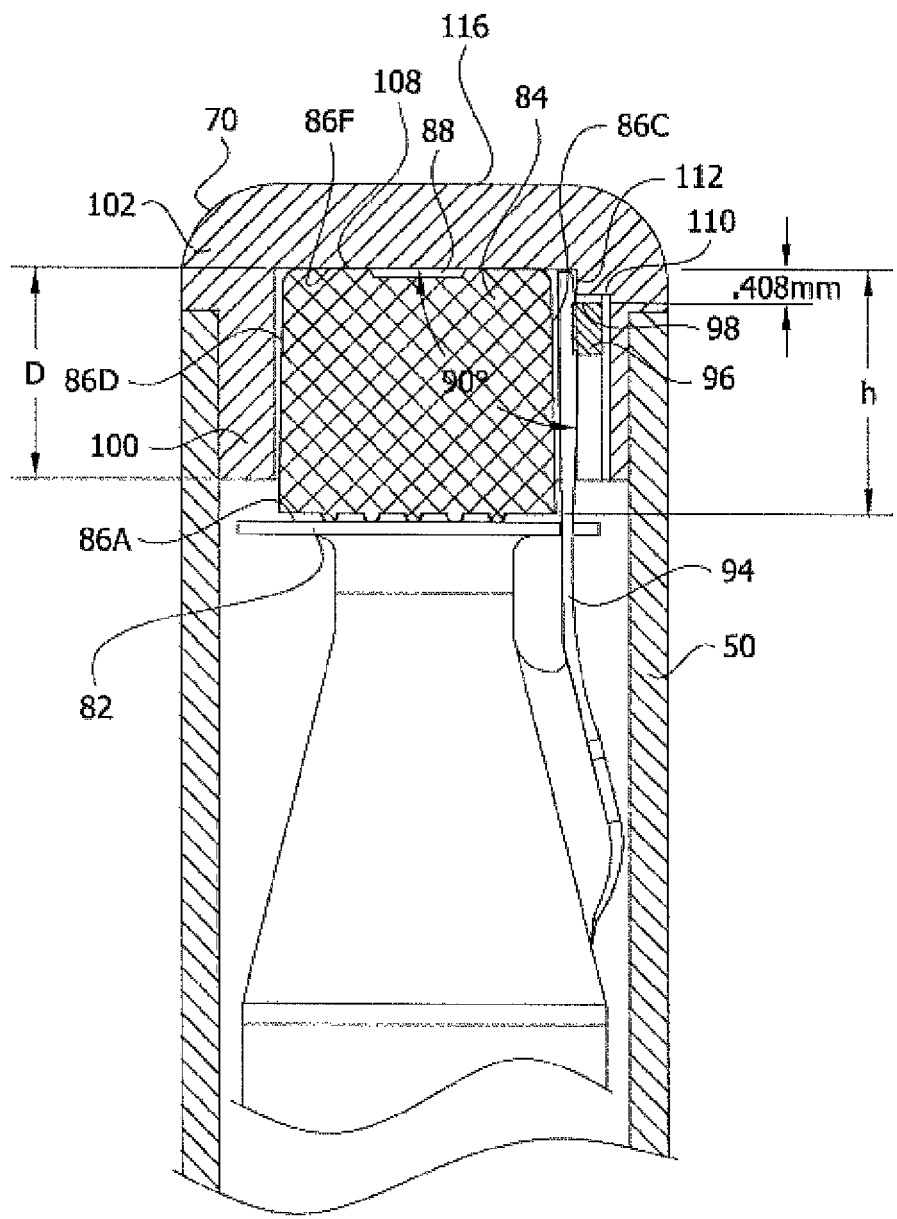
FIG. 9 is a schematic illustration showing a fragmentary view of the imaging assembly in FIG. 5, in accordance with one or more aspects of the invention.

Referring to FIGS. 7 and 9, a light-mounting portion 94 of the flex circuit 60 can be disposed at the side 86C of the camera 84. The light-mounting portion 94 is illustratively depicted as extending longitudinally toward the camera 84 from a lateral side edge of the flex circuit at a fold line of the power-mounting portion 90. One or more light sources 96 can be disposed on, for example, the light-mounting portion 94 for illuminating an area or region adjacent to the upper surface 86F of the camera housing 86. In the illustrated embodiment, the light source is a light emitting diode (LED) 96 disposed on the light-mounting portion 94 so that the LED is disposed on the side 86C of the camera housing and below or proximate the upper surface 86F of the camera housing. In the illustrated embodiment, the LED 96 has a light emitting surface 98 substantially perpendicular to the light-mounting portion 94 for projecting light outward from the distal end of the imaging assembly 18. According to the illustrated embodiment (FIG. 9), the LED 96 and the light-mounting portion 94 are positioned relative to the camera 84 and the camera-mounting portion 82 such that the light emitting surface 98 of the LED 96 is a relatively short distance, e.g., 0.408 millimeters, below the upper surface 86F of the camera housing 86. Typically, LED 96 has an illumination zone that is at least partially coincident over an imaging zone or field of view of camera 84, through optional lens 88.

Figure 44:
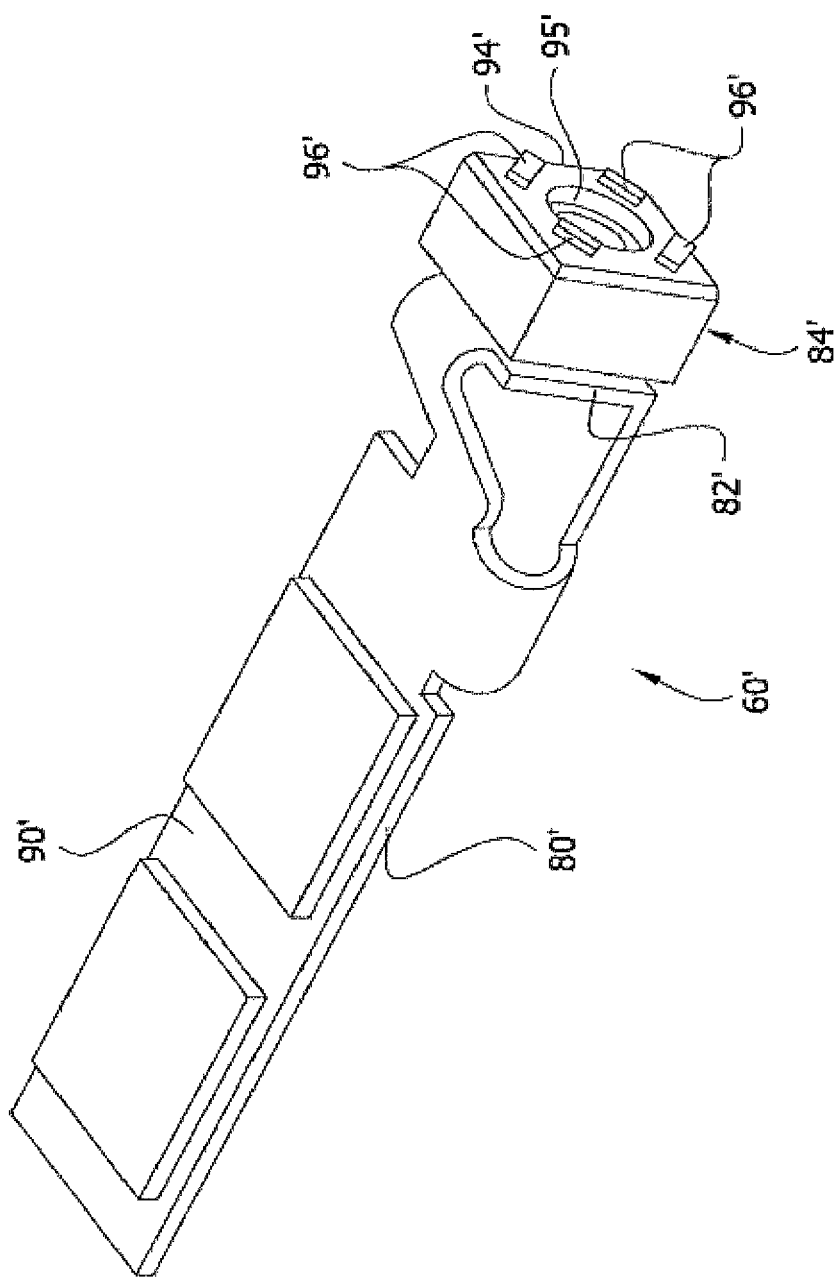
FIG. 44 is a schematic illustration showing a perspective view of a flex circuit assembly, with a flex circuit in a folded configuration, in accordance with one or more aspects of the invention.
Figure 45:
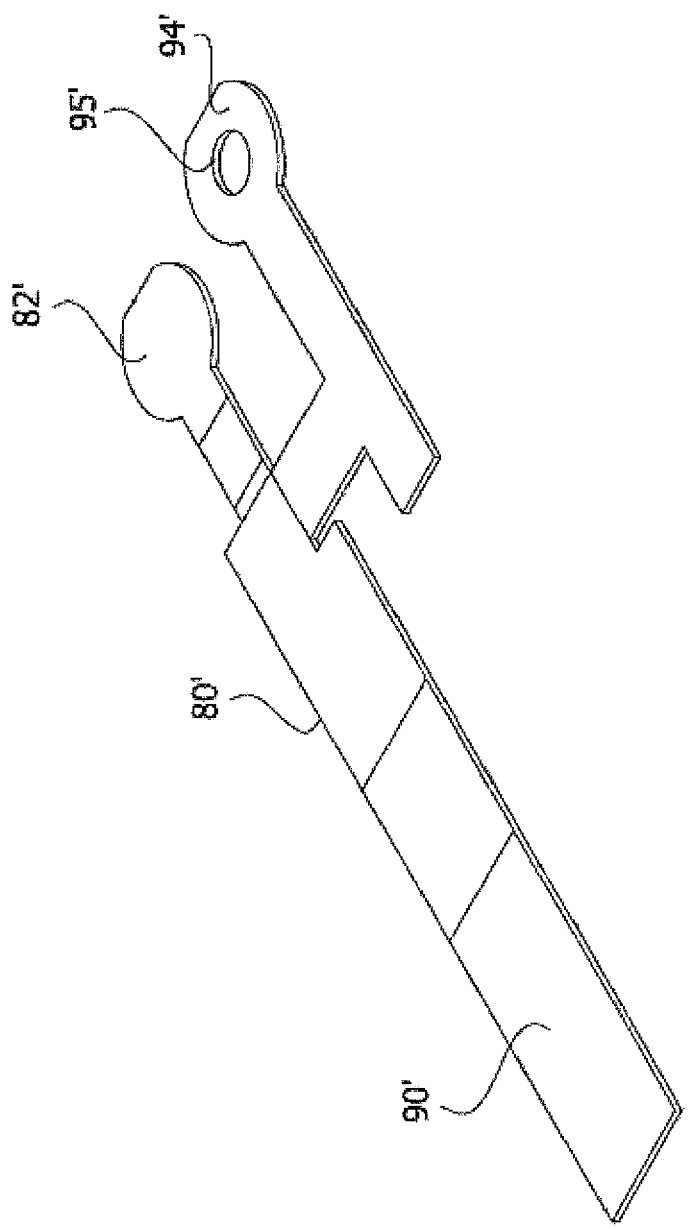
FIG. 45 is a schematic illustration showing a perspective view of the flex circuit in FIG. 44 in an unfolded or flat configuration, in accordance with one or more aspects of the invention.

In another embodiment, one or more LEDs may be located distal of the camera. As shown in FIG. 44, one example of flex circuit assembly is generally indicated at reference numeral 60'. As illustrated in a folded or at least partially assembled configuration, a flex circuit 80' of the flex circuit assembly 60' can include an electrical component-mounting portion 90', a camera-mounting portion 82' on which a camera 84' is mounted, and an LED-mounting portion 94' on which one or more light sources, such as four illustrated LEDs 96', can be mounted. The LED-mounting portion 94' is typically configured to rest on an upper surface of the camera 84' so that the LEDs 96' are distal or offset from the camera. The LED-mounting portion 94' can include an opening 95' aligned with the camera lens (not shown) so that the LED-mounting portion 94' does not obstruct the field of view of the camera 84'. FIG. 45 shows the flex circuit 80' in the unfolded or flat configuration. The flex circuit may have other configurations and provide alternative locations for mounting of the camera and the light source.

Figure 10:
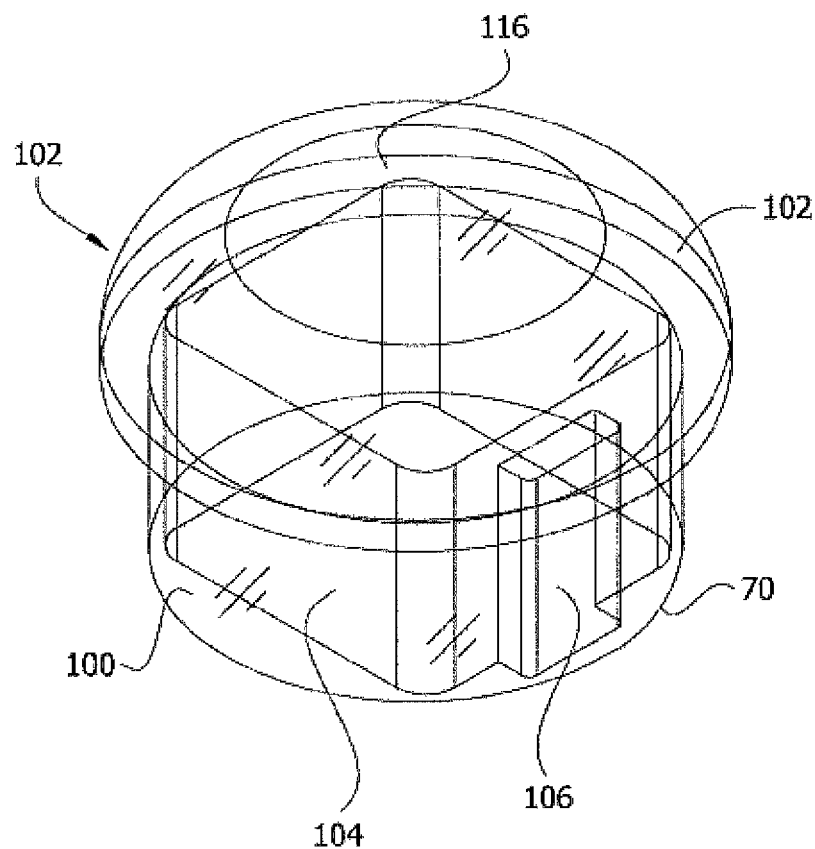
FIG. 10 is a schematic illustration showing a perspective view of a cap of the imaging assembly in FIG. 5, in accordance with one or more aspects of the invention.

Referring to FIGS. 9 and 10, the camera 84 and the LED 96 are illustratively shown as disposed in the optically transparent cap 70. The cap 70 can be configured to diffuse light emitted from any of the one or more LEDs 96, and, in some cases, to filter the emitted light into a range of or a particular frequency. The cap 70 can have an exterior surface comprising a cylindrical attachment portion 100 that is configured to couple or mate with the distal end of the tubular housing 50, and a dome-shaped portion 102 that may extend outward or project from the tubular housing. In one example, the cylindrical attachment portion 100 can be shaped and sized so that a snug fit is formed with the interior surface of the tubular housing 50. A bonding agent may be used to further secure the cylindrical attachment portion 100 to the tubular housing 50. The connection between the cap 70 and the housing 50 may be substantially waterproof to inhibit the ingress of liquid into the imaging assembly 18.

In some embodiments in accordance with one or more aspects of the invention, the cap 70 has an interior surface that defines a cavity extending inwardly from a proximal end of the cap. The cavity can provide or define a camera-receiving portion 104 and an LED-receiving portion 106. The camera receiving portion 104 can be correspondingly sized and shaped to snugly or tightly receive the sides 86B, 86C, 86D, 86E of the camera 84, and further can have a depth (indicated as "D" in FIG. 9) that is less than the height of the camera (indicated as "h" in FIG. 9) so that the camera extends out of the camera receiving portion 104 at the proximal end of the cap 70. This snug fit of the camera 84 in the camera-receiving portion 104 inhibits movement of the camera relative to the cap 70 and facilitates proper alignment of the cap 70 with the camera 84. The position of the cap 70 relative to the camera 84 may be adjusted or configured to at least partially reduce any effects that undesirably affect the quality of the image generated by the imaging assembly 18. In the exemplarily embodiment, the protruding portion of the camera housing that extends outside of the camera receiving portion can facilitate assembly by enabling the use of a fixture for precise positioning of the camera and the cap. In other variants, the cap may utilize different configuration to interface with the housing or other components of the imaging assembly. For example, one or more variants embodiments may involve having circular cylindrical volumes enclosing any of the one or more of the light sources and the imaging devices.

Referring further to FIG. 9, the interior of the cap 70 can be further configured to reduce unwanted light emitting from the LED 96 from entering the camera 84 and being sensed or detected by the camera. To minimize or at least partially reduce any reflection of undesirable light into the camera 84, an interior camera-opposing surface 108 of the cap 70, opposing the upper surface 86F of the camera housing 86, can be oriented or constructed to be substantially parallel to the upper surface 86F of the camera housing. Moreover, an interior light-opposing surface 110 of the cap 70 opposing the light emitting surface 98 of the LED 96 can be disposed to be spaced longitudinally, i.e., distally, from the camera-opposing surface 108 of the cap. A relatively sharp angle, e.g., a right angle, may be implemented and defined by the camera-opposing surface 108 and an interior surface 112 of the cap 70 that connects the interior surface 110 to the interior surface 108. This configuration should reduce any undesirable internal reflection of light emitted by the LED 96 into the camera 84.

Referring further to FIG. 10, the dome-shaped portion 102 of the exterior surface of the cap 70 includes central distal portion 116 that can be generally flat, e.g., generally planar. Side edges extending from the distal portion 116 to the base, e.g., proximal end of the dome-shaped portion, are round and generally smooth. Moreover, the base of the cap 70 has a cross-sectional size and shape that can be approximately the same as the cross-sectional size and shape of the housing 50 so that the cap transitions smoothly to the housing. Overall, this general shape of cap 70 is referred to herein as a truncated-dome shape. The flat, central distal portion 116 should minimize or at least reduce distortion in the field of view. In the illustrated embodiment, the flat, central distal portion 116 has a generally circular circumference and an area that is the same size or larger than the field of view to further minimize distortion in the field of view. Moreover, the portion of the interior surface of the cap 70 that opposes the flat central portion 116 of the exterior surface and the upper surface 86F of the camera 84 can also be flat and can be substantially in parallel with the flat central portion of the exterior surface, which should further minimize or at least reduce distortion in the field of view. The round edges of the cap 70 can facilitate insertion of the distal portion of the feeding tube assembly 12 into the subject and promotes comfort during intubation.

Figure 11:
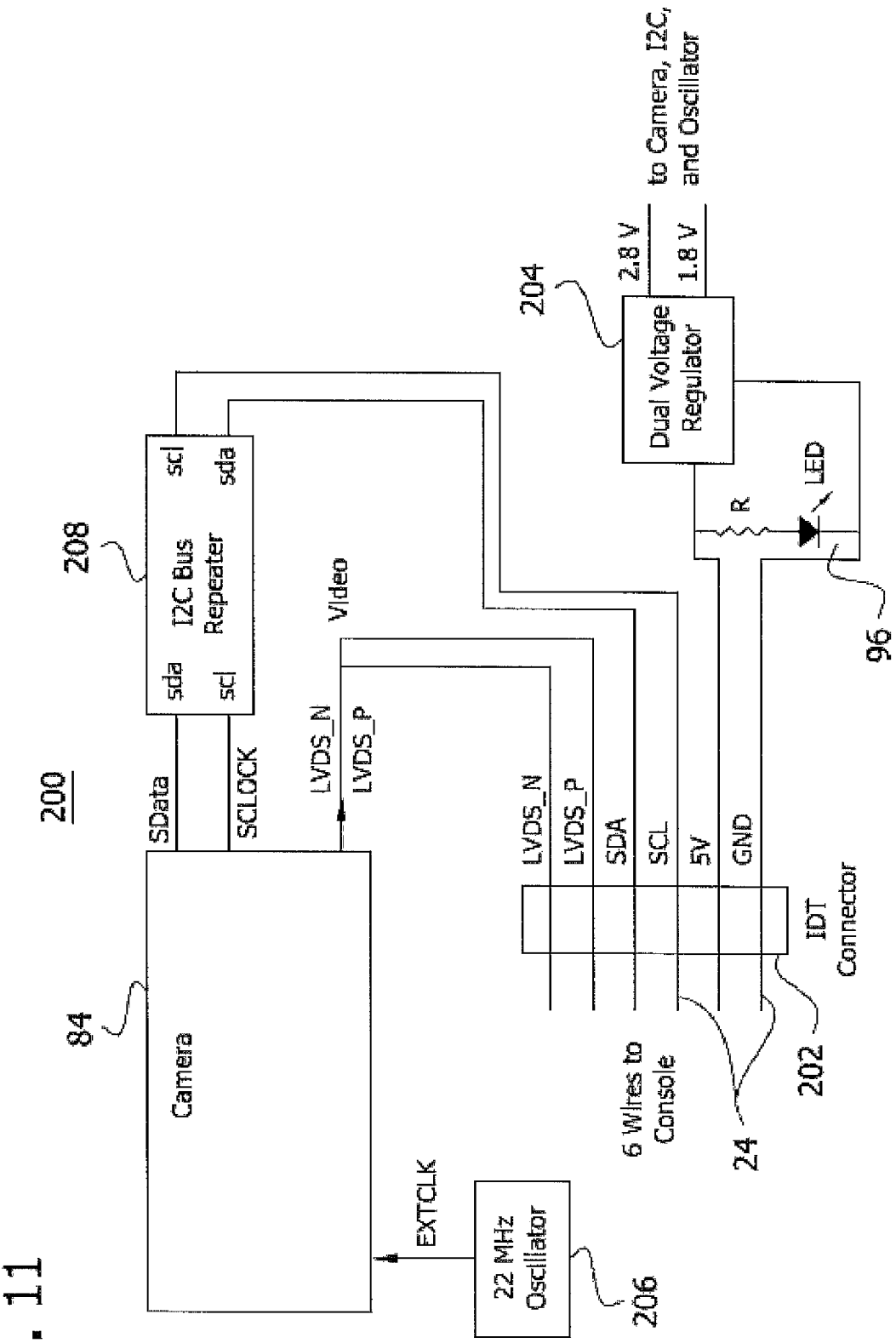
FIG. 11 is a block diagram of the flex circuit assembly in FIG. 7, in accordance with one or more aspects of the invention.
Figure 12:
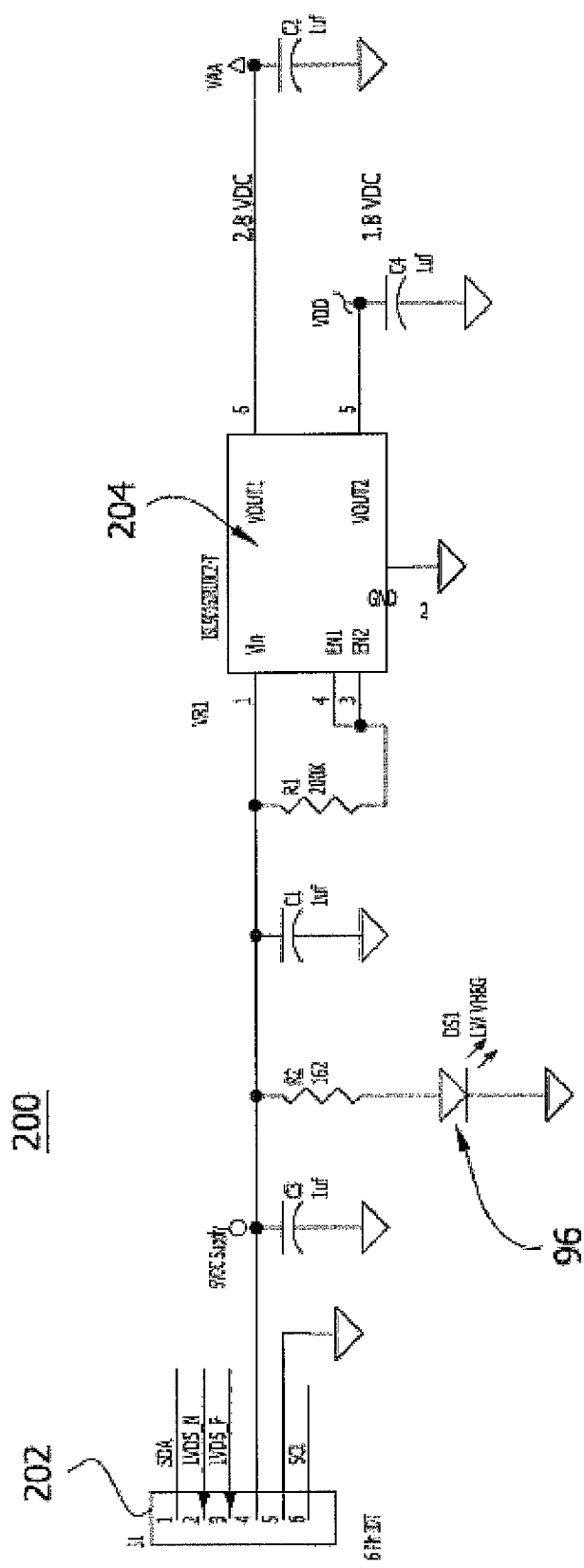
FIGS. 12 and 13 are circuit schematic illustrations of the flex circuit embodiment in FIG. 11, in accordance with one or more aspects of the invention.
Figure 13:
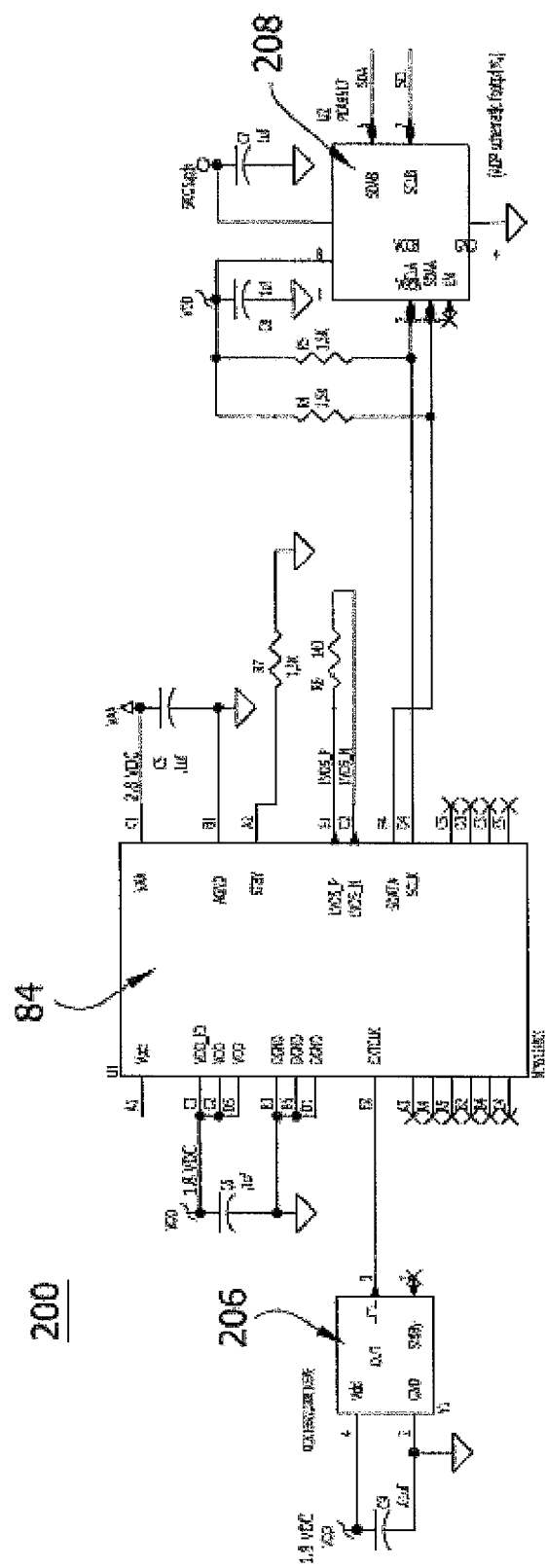

FIG. 11 shows an electrical block diagram directed to an exemplary electrical system 200 of the flex circuit assembly 60 in accordance with one or more embodiments of the invention. FIGS. 12 and 13 illustratively show circuit diagrams of the exemplary electrical system 200. The electrical system 200 can include an electrical conductor connector 202, such as an insulation displacement connector, for receiving the electrical conductors 24 from the outlet adaptor 20. According to the illustrated embodiment, the electrical conductors 24 include six signal lines. The six signal lines in the illustrated embodiment include two power supply lines, e.g., a power line, 5V, and a ground line, GND, two serial communication lines, e.g., a serial clock line, SCL, and a serial data line, SDA, and a differential pair, e.g., a low voltage differential signal positive line, LVDS_P, and a low voltage differential signal negative line, LVDS_N. The power supply lines (5V and GND) are electrically connected to the LED 96 for energizing the LED 96. In the illustrated circuit system 200, the power supply lines provide 5 Volt power to a white light LED, e.g., part number LW QH8G or LW VH8G available from OSRAM Opto Semiconductor GmnH, Germany. The power supply lines (5V and GND) are also electrically connected to a dual voltage regulator 204, or power supply, for providing power thereto. The dual voltage regulator 204 generates two different voltage lines from the power provided by the power supply lines. In the illustrated circuit system 200, the dual voltage regulator 204, e.g., part number ISL9016IRUJCZ-T available from Intersil Corporation, Milpitas, California, generates a 2.8 Volt power signal, e.g., analog supply voltage signal VAA, and a 1.8 Volt power signal, e.g., digital supply voltage signal VDD. The dual voltage regulator 204 is configured and electrically connected to supply voltage generated therefrom to an oscillator 206, a serial communication device 208, and the camera 84. In the exemplary electrical system 200, the camera 84 can be part number MTV9124M01, available from Aptina Imaging Corp., San Jose, Calif. However, other cameras or image sensors may be used without departing from the scope of the invention.

The oscillator 206, such as a 22 MHz oscillator, can be electrically connected to the camera 84 and configured to provide a timing signal (EXTCLK) thereto. The serial communication device 206, such as, an I2C bus repeater, available from Philips Semiconducor or NXP B.V, Germany, is electrically connected to the two serial communication lines (SDA, SCL) and to the camera 84 for allowing data, i.e., non-image data, to be communicated to and from the camera 84. For example, the serial communication lines (SDA, SCL) may be connected via the console connector 22 to an external computing device. The external computing device receives data representative of one or more camera settings, such as but not limited to resolution and frame rate. The camera settings can be communicated to the camera 84 via the serial communication lines (SDA, SCL) and the serial communication device 208. The camera 84 obtains images of the subject's anatomy in the field of view during and/or following intubation thereof and generates imaging signals such as a serialized digital video signal from the obtained images as a function of the camera settings communicated via the serial communication device 208. Operations performed by the camera 84 are synchronized as function of timing signal (EXTCLK) provided by the oscillator 206. The camera 84 outputs the signals, e.g., serialized digital video signal, to the differential pair lines (LVDS_N, LVDS_P) for transmission to the console connector 22 and to the console 23. The images obtained by the camera 84 may then be delivered, processed, and viewed via the console 23.

Figure 14:
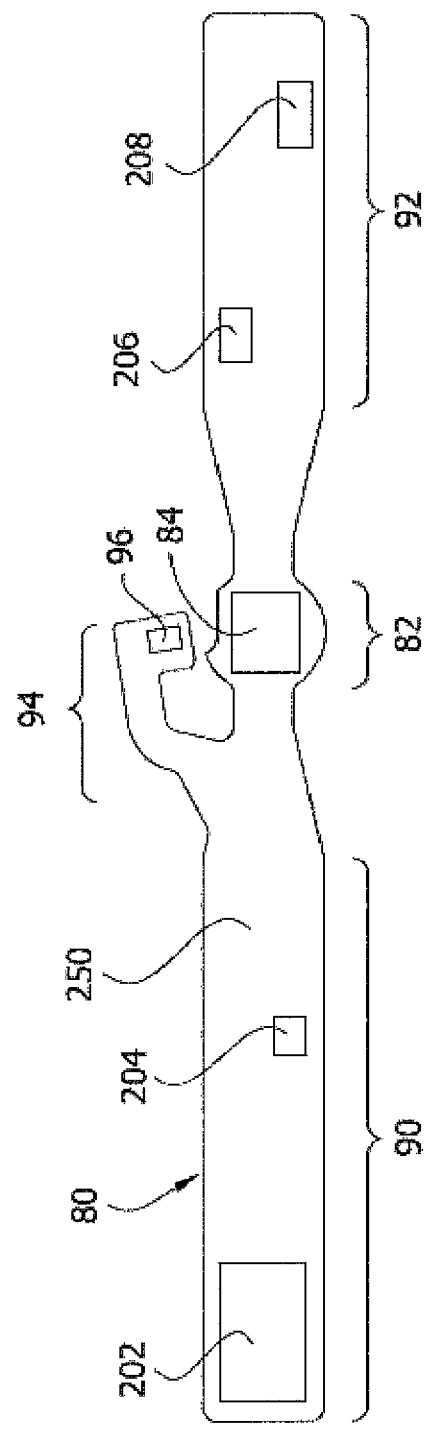
FIG. 14 is a schematic illustration showing a top plan view of the flex circuit assembly of the imaging assembly in FIG. 7, in an unfolded configuration, in accordance with one or more aspects of the invention.

FIG. 14 illustrates the flex circuit 80 in an unfolded, or flat, e.g., planar, configuration. In the unfolded configuration, the camera-mounting portion 82, the power-mounting portion 90, the data-mounting portion 92, and the light-mounting portion 94 all lie generally in the same plane and form a single planar surface, e.g., mounting face. In one embodiment, all of the electrical components of the electrical system, e.g., electrical system 200 for the imaging assembly 18 are attached to a single, generally planar mounting surface 250 of the flex circuit 80 when the flex circuit is in the unfolded configuration. Accordingly, the electrical components may be attached to the flex circuit 80 while it is in the unfolded configuration to facilitate manufacturing.

Relative locations of the electrical components of the exemplary electrical system 200 described above are shown in FIG. 14. In particular, the electrical conductor connector 202, e.g., insulation displacement connector, and the power supply 204, e.g., dual voltage regulator, can be attached to the mounting surface 250 of the power-mounting portion 90. A configuration, such as the illustrated configuration, in which the power supply 204 is typically located relatively close to the incoming electrical conductors 24, minimizes or reduces noise on the ground line (GND). The oscillator 206, e.g., timing generator, and the serial communication device 208, e.g., I²C bus repeater, can be attached to the mounting surface 250 of the data-mounting portion 92. The camera 84 can be attached to the mounting surface 250 of the camera-mounting portion 82. The exemplarily illustrated configuration locates the serial communication device 208 further from the electrical conductor connector 202 than the camera 84 because serial communication signals, e.g., serial data and serial clock signals, communicated between the serial communication device 208 and the electrical conductor connector 202 have a lower bandwidth than the video signal communicated from the camera 84 to the electrical conductor connector 202. An LED 96 is attached to the light-mounting portion 94. The camera-mounting portion 82 is shaped and configured so that the light-mounting portion 94 can be disposed to be flush with a side 86C of the camera housing when the flex circuit assembly 60 is in the folded configuration described above.

Figure 15:
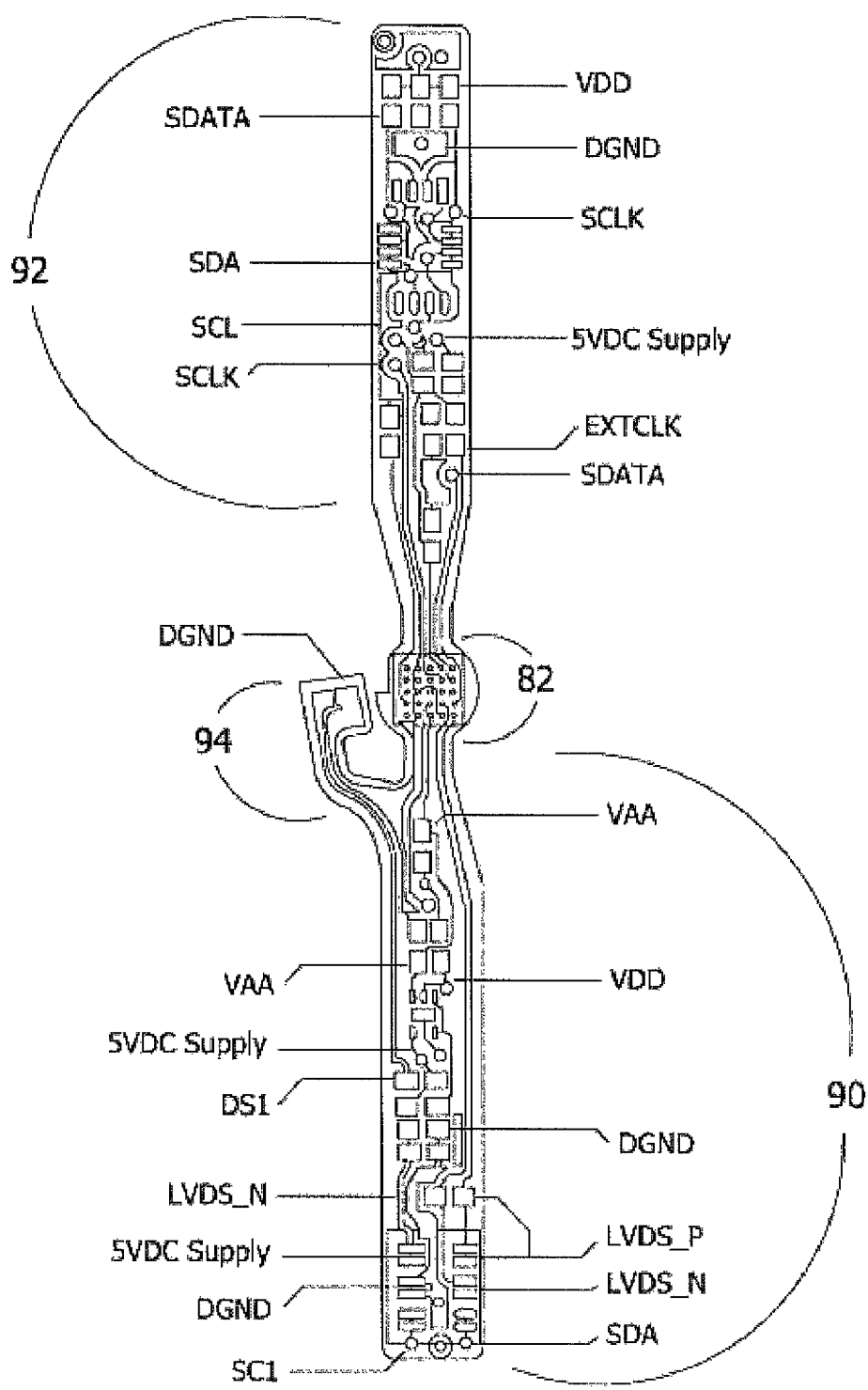
FIG. 15 is a schematic illustration showing a top view of a first substrate of the flex circuit assembly in FIG. 14, in accordance with one or more aspects of the invention.

In one embodiment, the flex circuit 80 of flex circuit assembly 60 is a two-layer circuit. In particular, the flex circuit 80 includes a first substrate and a second substrate, each having top and bottom surfaces. The first and second substrates may be composed of a flexible polyimide film. Electrically conductive material, e.g., copper, selectively disposed on the top surface of the first substrate forms a first circuit pattern, e.g., plurality of selectively connected traces. FIG. 15 illustrates a first circuit pattern for the exemplary electrical system 200 in accordance with some aspects of the invention. Electrically conductive material selectively disposed on the top surface of the second substrate forms a second circuit pattern. The first and second substrates are arranged in parallel with one another, e.g., stacked, so that the top surface of the first substrate directly opposes the bottom surface of the second substrate. The first circuit pattern and the second circuit pattern are electrically connected together by using, for example, vias, and connected with the electrical components attached to the flex circuit to form a two-layer circuit. The flex circuit 80 may be composed of other material and may be formed in other ways without departing from the scope of the present invention.

In one embodiment, the light-mounting portion 94 of the flex circuit 80 is configured to function as a heat sink. The electrically conductive material on the top surface of the first substrate and the electrically conductive material on the top surface of the second substrate and can be connected together using, for example, vias, to conduct heat from the first substrate to the second substrate. The traces formed on the second substrate of the light-mounting portion of the flex circuit can be wider relative to traces formed on other portions of the first and second substrates. For example, the wider traces may have a width of about 0.008 inches. This configuration minimizes or can reduce the likelihood of a temperature increase resulting from heat generated by the LED 96, and can allow a greater current to be provided to LED 96 to maximize or increase the illumination capability generated by the LED 96, while preventing or reducing the likelihood of any damage to the LED 96 and disturbances to the patient caused by undesirable or unacceptable high temperatures.

Referring to FIGS. 7, 8, and 14, in order to convert the flex circuit assembly 60 from the flat configuration to the folded configuration, the power-mounting portion 90 and the data-mounting portion 92 are folded toward each other at first fold lines 97 (FIGS. 7 and 8) to form the camera-mounting surface 82 between the fold lines 97. The power-mounting portion 90 and the data-mounting portion 92 can be folded a second time at second fold lines 99 so that the two portions are generally parallel and in opposing relationship to one another. The light-mounting portion 94 also can be folded inwardly toward the camera-mounting portion 82.

Alignment of the power-mounting portion 90 and the data-mounting portion 92 during assembly can be facilitated because there would be no components disposed on the inner or back surface of the flex circuit, i.e., the components are mounted on the mounting surface. The alignment of the power-mounting portion 90 and the data-mounting portion 92 also can improve the alignment of the camera to a desired orientation. The stresses and forces associated with the foldlines 97 and 99 on either side of the camera-mounting surface 82 balance each other out. As a result, the equivalent or counteracting stresses or forces induces positioning the camera 84 into a particular orientation such that the lens 88 is aligned with the cap 70 and the viewing field of view of the lens 88 is can be coincident with the axis of the tubular housing 50.

Figure 16:
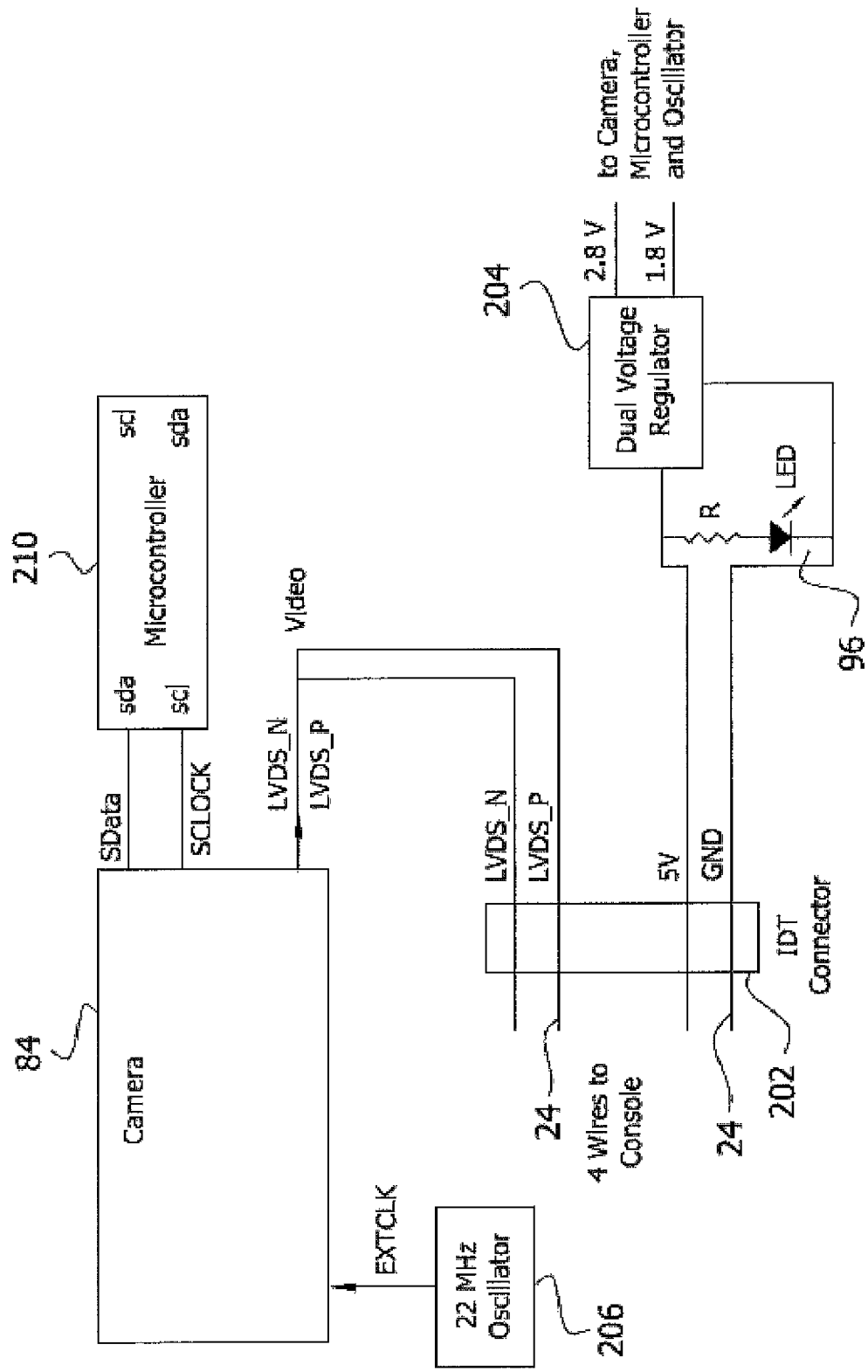
FIG. 16 is a block diagram of the flex circuit assembly, in accordance with one or more aspects of the invention.

FIG. 16 is a block diagram of an exemplary flex circuit electrical system according to an alternative embodiment of the invention. As shown, the electrical conductors include four cables constituting four signal lines. The four signal lines in the illustrated embodiment include two power supply lines, e.g., a power line, 5 V, and a ground line, GND, and a differential pair, e.g., a low voltage differential signal positive line, LVDS_P, and a low voltage differential signal negative line, LVDS_N. A microcontroller 210 cooperates with camera 84 to allow integration into feeding tube assembly 10. The camera 84 includes, for example, an I2C command/control interface and a serialized digital video output interface. The microcontroller 210 can send command and control signals directly to camera 84 rather than transmitting these signals over the length of the tube. Other operating parameters described herein, such as the exemplary embodiments associated with FIGS. 11-13, may be implemented in this variant.

Figure 17:
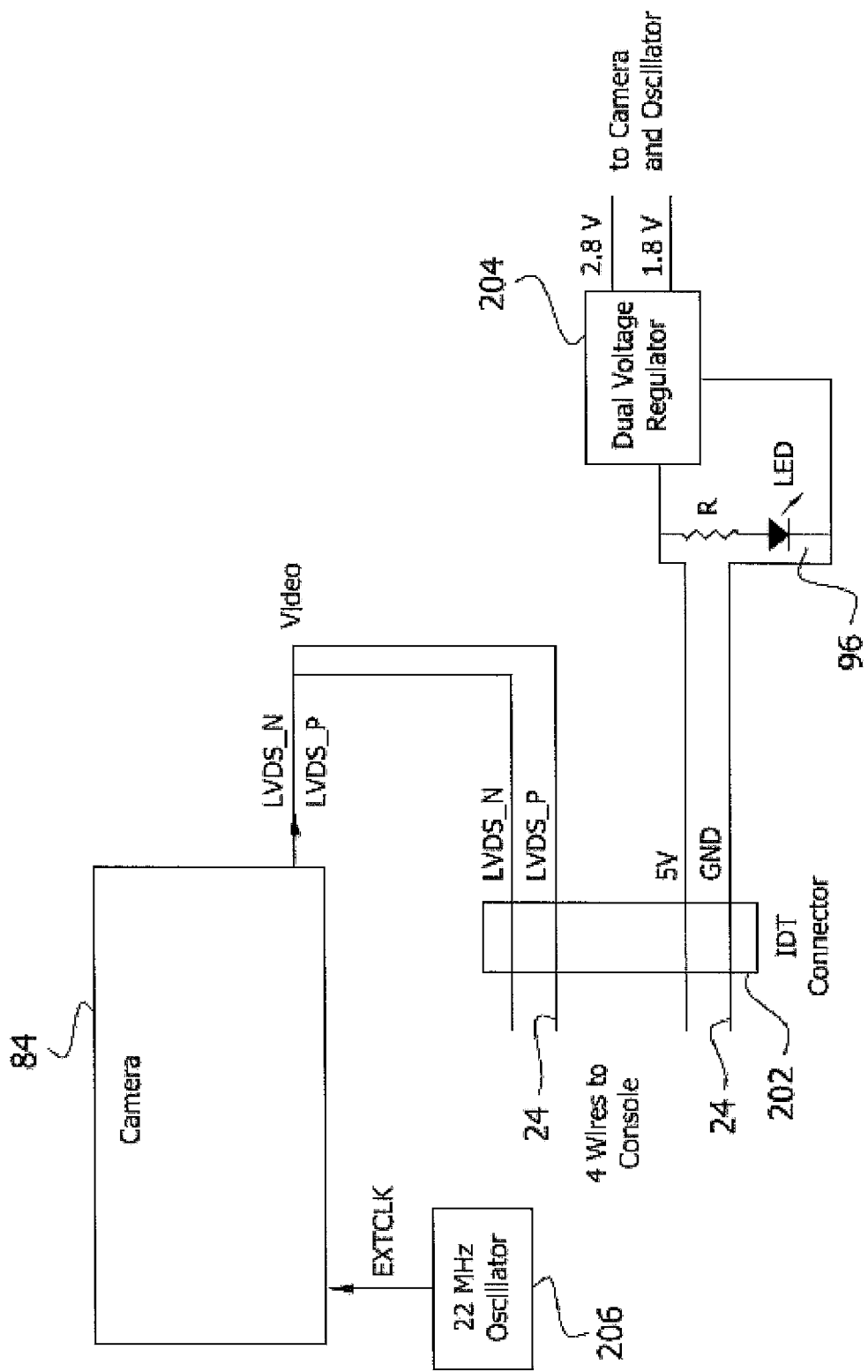
FIG. 17 is a block diagram of the flex circuit assembly, in accordance with one or more aspects of the invention.

In FIG. 17, the electrical conductors 24 include four cables constituting four signal lines in accordance with one or more further embodiments of the invention. The camera 84 can be customized to operate automatically and/or autonomously to a predefined operating protocol when powered up or energized. In this embodiment, camera 84 does not use or rely on external, incoming command/control signals. The operating parameters of the camera 84, such as, but not limited to, exposure, white balance, can be pre-programmed, pre-set, or permanently set to custom or tailored values for, for example, a particular or predefined application. In one embodiment, for example, the custom values would typically be stored in an associated memory structure. Camera 84 can include a sequencer (not shown), such as a microcontroller integrated in the camera module itself, which has a one time programmable memory (OTPM) (not shown) that can be programmed with the custom values. Alternatively, camera 84 can include hardware registers (not shown) that have the custom values stored therein, in which case the sequencer may be optionally operable. Other operating parameters described herein may be implemented in this embodiment.

Figure 18:
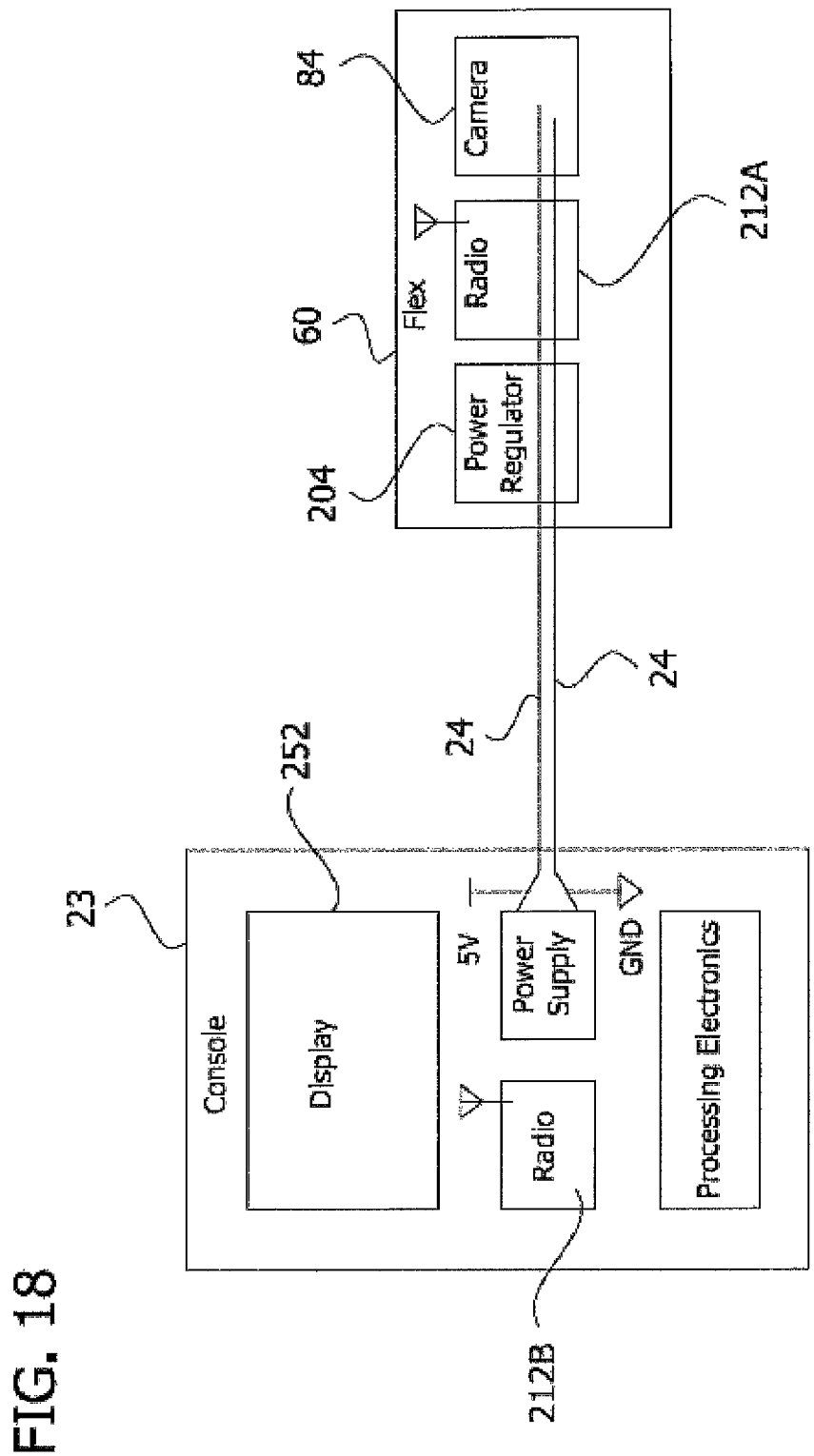
FIG. 18 is a block diagram of an exemplary feeding tube system, in accordance with one or more aspects of the invention.

FIG. 18 illustrates yet another embodiment of an exemplary flex circuit electrical system. As shown in FIG. 18, the electrical conductors 24 include two cables constituting two signal lines. The two signal lines in the illustrated embodiment include two power supply lines, e.g., a power line, 5V, and a ground line, GND, for supplying power from a console to the flex circuit 60. The console 23 can energize or provide power to the flex circuit 60 and can regulate voltage as needed to power a radio 212A as well as the camera 84 and other components of the flex circuit 60. The camera 84 can then send imaging signals, such as video data, via radio 212A wirelessly to a corresponding radio 212B located at the console. In an alternative embodiment, the console 23 and the camera 84 can communicate bi-directionally via radios 212A, 212B to exchange, for example, non-video data. Providing power to camera 84 in this manner can eliminate the need for a limited-capacity energy source, such as a battery, in the camera module itself.

Reducing the number of signal lines as shown in FIGS. 16-18, especially when combined with a flex circuit, may reduce cost and improve reliability and ease of assembly. Further, fewer conductors can reduce the likelihood of inadvertently switching lines and incorrectly connecting them during assembly.

Figure 4A:
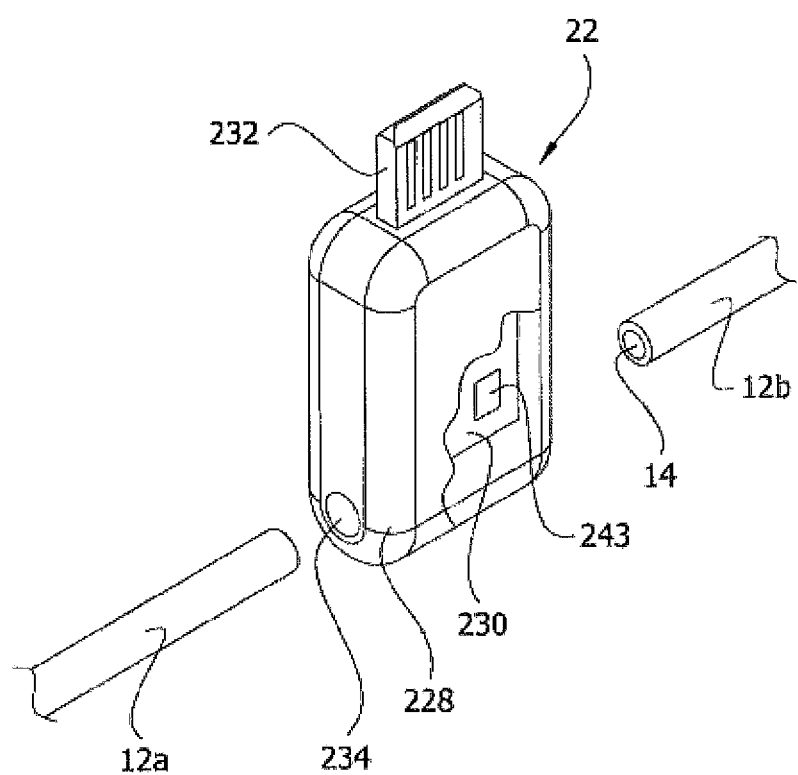
FIG. 4A is schematic illustration showing a perspective view of a console connector of the feeding tube assembly in FIG. 1, showing internal components and including feeding tube segments of a feeding tube, in accordance with one or more aspects of the invention.

Referring to FIGS. 2 and 4A, the exemplarily illustrated console connector 22 includes a connector housing 228 and a printed circuit board (PCB) 230, secured to the connector housing. The PCB 230 includes an edge connector 232 extending outward from the housing 228 so that an electrical component-mounting portion of the PCB is disposed in the connector housing 228 and the edge connector is exposed and thus can be generally accessible for a connection thereto. In the illustrated embodiment, the connector housing 228 defines a tube-connection opening 234 in which the first and second tube segments 12a, 12b are secured, such as by an adhesive, to fluidly connect the first and second tube segments. The tube-connection opening 234 may partially define the feeding passage 14, or the feeding passage may be entirely defined by the tube segments 12a, 12b. In one non-limiting example, a one-piece tube 12, incorporating or in lieu of segments 12a and 12b, extends through the tube connection opening 234, such that the feeding passage is entirely defined by the tube and is not in fluid communication with any portion of the console connector 22. The tube 12 may be secured within the tube-connection opening 234, such as by adhesive. The console connector may be of other configurations and may be secured to the feeding tube assembly at other locations.

The electrical conductors 24 extend from the first tube segment 12a into the connector housing 228 and are electrically connected to the PCB 230. An interface cable 242 or other signal-transmitting component can be removably connectable to the edge connector 232 to effect communication and data exchange between the console 23 and the imaging assembly 18. As explained in more detail below, an electronic memory component 243, such as electrically erasable programmable read-only memory (EEPROM), may be mounted on the PCB 230 to allow information, i.e., data, to be stored and/or written thereon and to be accessible by the console 23, i.e., a microprocessor 254 of the console 23, or another external device. The PCB 230 may have additional or different electrical components mounted thereon, or the PCB may be omitted such that the electrical conductors are operatively connected to the PCB 230.

Figure 4B:
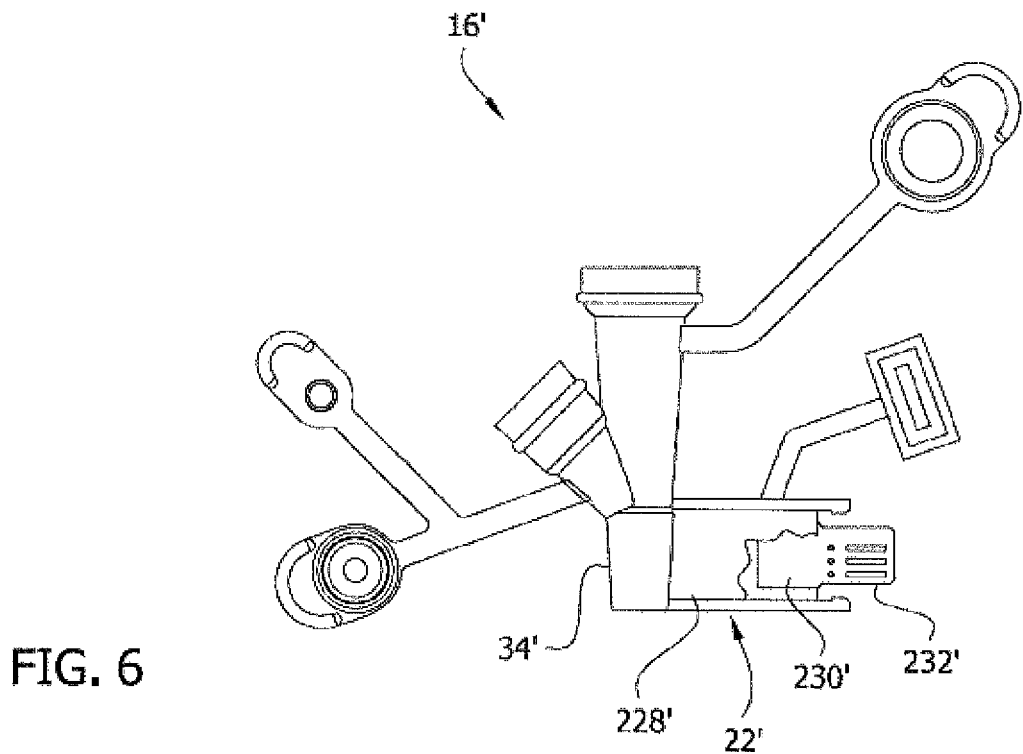
FIG. 4B is a schematic illustration showing another embodiment of an inlet adaptor for the imaging feeding tube assembly, in accordance with one or more aspects of the invention.

In another embodiment, a console connector may be formed on or secured to an inlet adaptor. Referring to FIG. 4B, in one embodiment of the invention, a housing 228' of a console connector 22' is formed integrally with an inlet adaptor 16'. The console connector housing 228' extends laterally outward from an outlet port 34' of the inlet adaptor 16'. Like the previous embodiment, the current console connector 22' optionally includes a PCB 230' with an edge connector 232' for use in communicatively connecting the imaging assembly with the console. An electronic memory component, such as an EEPROM (not shown) may be mounted on the PCB 230', as disclosed above and explained in more detail below. The feeding tube assembly may include a different type of connection for connecting the imaging assembly 18 to the console 23.

Referring to FIG. 3, the illustrated interface cable 242 includes first and second interface connectors 244, 246 on opposite longitudinal ends of the cable. The first interface connector 244 is releasably mateable with and electrically connectable to the edge connector 232, and the second interface connector 246 is releasably mateable with and electrically connectable to the console 23. One or both of the interface connectors 244, 246 may be discriminating connectors, i.e., non-universal connectors, that will only mate and connect with respective connectors associated with the feeding tube assembly 10 and the console 23. Moreover, the edge connector 232 or other connector may be disposed within a socket having a shape that selectively and discriminatingly mates with a corresponding, e.g., complementarily configured, first interface connector 244. The socket and the first interface connector 244 may include engagement structures, such as ribs or other components that provide a friction-fit between the connector and the socket to inhibit inadvertent disconnection. The connection between the interface cable 242 and the console connector 22 may be of other configurations without departing from the scope of the present invention.

Referring still to FIG. 3, the interface cable 242 may include a control device, such as a button 248, to allow the user to record a still image, e.g., take a snapshot image, of real time video being displayed on the console 23. Actuating the button 248 or other control device sends a signal to the console 23 instructing the console to record image information, e.g., a still image along with associated temporal information. In one example, the control device 248 can be proximate or on the first interface connector 244; for example, the control device can be closer to the first interface connector than the first interface connector 246. In one or more exemplary embodiments of the invention, the control device can be provided on the first interface connector or within 12 inches of the first interface connector. The console 23 may also include a snapshot control function, e.g., an icon, button, or other actuation device that allows the user to take and record a snapshot image using the console, that can be optionally stored in a memory structure, and which may include ancillary information such as the date and time. In some situations or embodiments it is envisioned that during insertion of the feeding tube assembly 10 in the patient, the console 23 may be located at a distance that is not within reach of the user, such as a medical practitioner. Thus, although the images, e.g., video, may be viewable on the console 23, the user may not be able to reach the console to perform additional operations or functions on the console during insertion of the feeding tube assembly 10. Accordingly, by providing a control device 248 on the interface cable 242, and more specifically, by providing a control device that is adjacent the first interface connector 244, the user can take and record a snapshot image without having to reach for the console 23. The interface cable 242 may be of other configurations without departing from the scope of the present invention.

As shown in FIG. 3, the illustrated console 23 can include a console housing 250, a console display 252, such as an LCD or other electronic display, secured to the housing, and a microprocessor 254 disposed in the housing. In the illustrated embodiment, the microprocessor 254 communicates with the imaging assembly 18 through the interface cable 242 and the electrical conductors 24. The microprocessor 254 can be configured to receive the imaging signal or video signal transmitted by the imaging assembly 18 and display real-time images associated with the imaging signal on the display. As disclosed in more detail below, the microprocessor 254 can be optionally configured to display a graphical user interface on the console display 252, or a different display. The console 23 can include one or more user input devices to allow the user or operator to communicate with the microprocessor 254 to perform various operations using the console 23. The display 252 may be a touchscreen, such as a touchscreen LCD or other types of displays, which also functions as a user input device. In one embodiment, the touchscreen allows the image to be enlarged or reduced by touching the screen with two fingers and either moving apart to enlarge or bringing together to reduce the image size. Other user input devices, in addition to or in lieu of the touchscreen display 242, such as a mouse, a keyboard, a joystick, or other user input devices, may also be provided. Some other devices may include, without limitation, the ability to accept and act on voice commands or upon gestures by the clinician. These latter input devices have the advantage of not requiring that one be able to touch the console. Other ancillary components can be utilized in the console 23, including, but not limited to power supply subsystems and serial buses.

Referring to FIG. 4A, as disclosed above the console connector 22 on the feeding tube assembly 10 may include an electronic memory component 243, such as an EEPROM, for storing and/or writing data thereon that is accessible by the console 23 or other internal or external devices associated with the feeding tube assembly, such as the enteral feeding pump. One or more of the following types of information may be provided on or written to the electronic memory component in one or more embodiments of the present invention.

In one non-limiting example, data relating to the feeding tube assembly 10 may be written, stored, or otherwise incorporated into the electronic memory component 243. For example, data indicating the lot code and/or the item code, e.g., serial number, may be written to the electronic memory component 243, and be retrievable by the console 23 as a predefined identifier. Moreover, a proprietary verification code may be included in the electronic memory component 243 to provide information that can facilitate verification to the console 23 that the feeding tube assembly 10 is a valid feeding tube to be used with the console. The console 23 may be configured, by, for example, executing instructions, to verify that the feeding tube assembly is an acceptable, proper, unexpired, or compatible feeding tube assembly before allowing operation or additional operation. Without proper validation, for example, the console 23 may inhibit images from displaying on the console if the feeding tube assembly 10 does not have valid information, such as an acceptable code or an acceptable predefined identifier. In addition, data indicating whether the feeding tube assembly 10 is sterilized may be written to the electronic memory component 243. Other information relating to the feeding tube assembly 10 may also be written to or otherwise incorporated in the electronic memory component 243. The electronic memory component may thus serve as a validation assembly or key that would provide one or more predefined identifying information, e.g., a predefined identifier, that can be utilized by the console before or during operation thereof.

In another non-limiting example, the data indicating time, i.e., time stamps, relating to the feeding tube assembly 10 may be written to the electronic memory component 243. For example, the date of manufacture of the feeding tube assembly 10 may be written to electronic memory component 243. When the feeding tube assembly 10 is connected to the console 23, such as by the interface cable 242, the console may read the data indicating the date of manufacture. In one non-limiting example, the console 23 may use the date of manufacture to determine if the feeding tube assembly 10 has exceeded its storage life. If the feeding tube assembly 10 has exceeded its predetermined storage life, the console 23 may be configured or execute programmed instructions that perform at least one of initiate an alarm, communicate a message indicating that the storage life is exceeded, and prevent viewing of images from the imaging assembly 18. In another example, upon connection of the feeding tube assembly 10 with the console 23, the console may be programmed to write a start date of service or date of first use on the electronic memory component 243. This start date can be used as a reference to determine when the predefined usage life of the feeding tube assembly 10 has been exceeded or is about to expire. For example, after writing the start date to the electronic memory component 243, the console 23 may be configured to determine the usage duration or use life of the feeding tube assembly, and compare the elapsed usage duration with an expiration date (and time) to determine the remaining usage life or whether the service life, usage time, or both, of the feeding tube assembly will expire or has expired. Other variants may involve periodically, continually, or continuously determining whether the current date or usage date exceeds the expiration date. If the console 23 determines that the usage life of the feeding tube assembly 10 has expired, then the console may be programmed to at least one of initiate an alarm, communicate a message indicating that the usage life is expired, make a record on any recorded images, and prevent viewing of images from the imaging assembly 18. The cumulative use time may be determined by writing time stamps to the electronic memory component 243 to determine the hours of actual use.

The console 23 may be configured to write other information to the electronic memory component 243. For example, the console 23 may be programmed to write a serial number or other identifier associated with the console so that other consoles and other devices, such as enteral feeding pumps, can read the electronic memory component 243 and determine which console was used with the selected feeding tube assembly 10. In another non-limiting example, the console can be configured to write to the electronic memory component 243 patient specific information including, for example, the subject's, e.g., the patient's, name, the subject's identification code, and other information relating to the patient, including but not limited to, the type of enteral product to be fed to the patient as well as the patient's feeding schedule, feeding duration, associated feeding settings, or other historical information. The patient information may be written to the electronic memory component 243 before the feeding tube assembly 10 is connected to the console 23, and the console may be programmed to read the patient information. Alternatively, the user may use the console 23 to write the patient's information to the electronic memory component 243. The patient's information may be encrypted to ensure patient confidentiality.

In yet another non-limiting example, a placement-confirmation time stamp or some other confirmation identifier may be written to the electronic memory component 243 to indicate that the proper placement of the feeding tube assembly 10 in the patient was confirmed. The console 23 may be configured to write the time stamp to the electronic memory component 243 when the user indicates to the console that the feeding tube assembly is properly located. For example, the user may press a button or perform some other operation to confirm proper placement. In addition to a time stamp or other confirmation identifier, a username or other user identification can be written to the electronic memory component 243.

Figure 19:
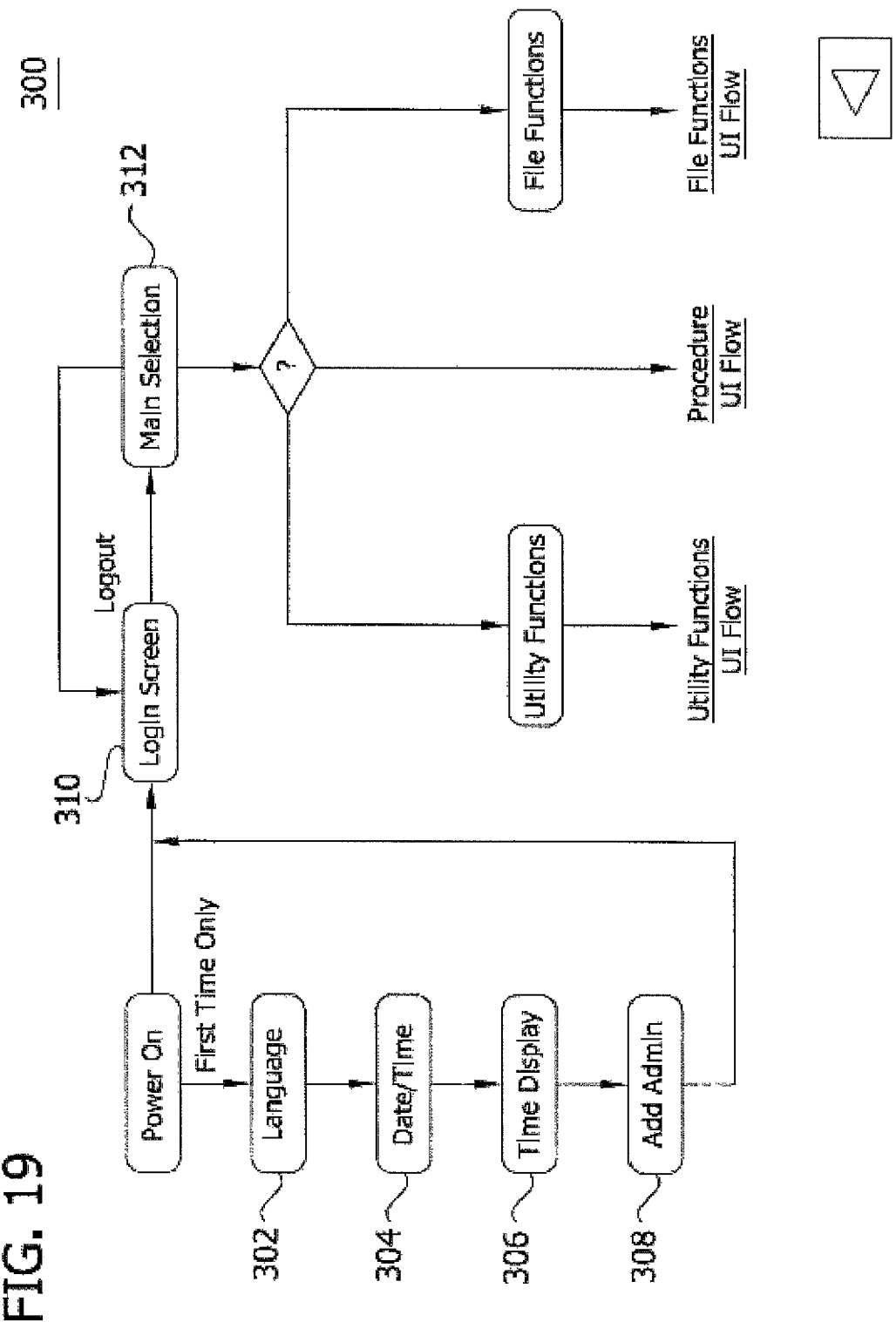
FIG. 19 is a flow diagram showing an exemplary graphical user interface screen flow, in accordance with one or more aspects of the invention.

FIGS. 19-31 illustrate one or more features relating to an exemplary graphical user interface of the console. One or more of the features described herein may be incorporated into various embodiments of the invention. FIG. 19 is a flow chart illustrating the operations of the graphical user interface when the console 23 is powered on for the very first time, or when the console is activated after a predetermined time period of non-use by a user. The predetermined period of non-use can be one month, six months, or even one year. Other triggering conditions that may affect a first time start may involve a loss of power.

As illustrated, a user interface screen prompts a user to indicate whether the user is the very first user of the console 23 ("initial user"), or whether the user has already been associated with the console. If the user is the initial user, the console 23 grants the initial user administrator status along with associated privileges for accessing all or predetermined features of the console. Accordingly, at 302, the initial user is prompted to select a language (labeled "Language") that will be displayed on the user interface screens to communicate with users. At 304, the initial user is prompted to enter the current date and time, and optionally to specify a format for displaying the time (labeled "Date/Time"). At 306, the initial user is optionally prompted to enter time tracking options for display by the user interface (labeled "Time Display"). The initial user can select one of the following options: the current time of day is tracked and displayed by the console 23; the elapsed amount time for the current procedure being conducted by the feeding tube assembly 10, e.g., initiated when patient data is entered, is tracked and displayed by the console; both, the current time of day and the elapsed amount of time for the current procedure being conducted are tracked and displayed by the console. At 308, the initial user is optionally prompted to set up an administrator account by entering a username and a password.

If the user indicates that the user is not the very first user of the console 23, the console, at 310, presents to the user a log-in user interface screen. The user enters a username and password. If the user enters a valid username and password associated therewith, the user is logged in. If the console 23 determines that the username and password are not valid, the console presents the user with a log-in retry, i.e., message and another opportunity to log in. In one embodiment, after a predefined number of log-in attempts, the console 23 may be reset; all patient data, user data, and device data may be deleted, locked or becomes otherwise inaccessible. If the user is successfully logged in, at 312, the user is presented with a main selection user interface screen. The main selection user interface screen can present the user with one or more of the following navigational options: utility functions, procedure screen, file functions, and logout. The navigational options may be presented via text and/or graphical icons. In addition, a portion of the main selection user interface screen (labeled "Preview Video" or graphically represented as a movie reel icon, for example) is dedicated to providing the user with video data if video data is being received from the imaging assembly 18 when the main selection user interface screen is being accessed. As described below, this generally occurs when the user selects the main selection user interface screen after initiating a procedure.

In one embodiment, the console 23 is configured to recognize a plurality of classes or statuses of users and to limit operations that may be performed by the console as a function of a class associated with each user. For example, the console 23 may be configured to recognize four classes of users: operators, administrators, approvers, and maintainers. The console 23 can be configured to authorize the operator class of users to view video data that is received from the imaging assembly 18. The console 23 can be configured to authorize the administrator class of users to create or establish user accounts or other operator accounts, along with respectively associated data storage substructures, and to view video data that is received from the imaging assembly 18. The console 23 is configured to authorize the approver class of users to view video data or imaging data that is received from the imaging assembly 18 and to annotate approval data onto the video data or imaging data received from the imaging assembly. The console 23 can be configured to authorize the maintainer class of users to perform maintenance functions to the console such as software updates. However, the console 23 only authorizes the maintainer class of users to operate the console if the console is not storing any patient data, e.g., patient data must be deleted from console before a maintainer user is authorized to operate the console.

If the user selects the utility functions from the main selection user interface screen, a utility functions user interface screen can be presented to the user. The options presented to the user on the utility functions user interface screen are typically based on the class or status associated with the user. If the user is an operator or an approver, the user can be presented with a utility functions user interface screen. The console can then provide the user with the "Language" option and the "Preview Video" feature discussed above. The utility functions user interface screen also can provide the user with a "User Manager" option which allows the user to navigate to a user manager navigation user interface screen that allows the user to change his/her password. If the user is an administrator, a utility functions user interface screen presented to the user has the "Language," "Date/Time," "Time Display," and "Preview Video" options discussed above. A "User Manager" option can also be provided, which allows the user to navigate to a user manager user interface screen. A user manager user interface for the administrator allows the administrator to add a user via the user interfaces. The utility functions user interface screen presented to the administrator also can also have an option, labeled "Reset/Erase Console," for resetting, e.g., deleting patient data, user data, and device data, or erasing the console, e.g., deleting patient data and device data, and for performing a software update, labeled "SW Update". In addition to the options presented to an administrator user, the utility functions user interface screen presented to a maintainer user additionally provides the maintainer user with the option to perform maintainer functions (labeled "Maintainer Functions"). For example, "Maintainer Functions" may include software debugging functions.

Referring again to the main selection user interface screen if the user selects the "Procedure Screen" option, a patient information user interface screen is displayed to the user via the console 23. The patient information user interface screen prompts the user to enter a name and identification for the patient for which the procedure is being performed. If the user enters the name and identification of the patient, the procedure main user interface screen is displayed to the user and the console 23 begins receiving video data from the imaging assembly 18 of the feeding tube assembly 10 so long as the feeding tube assembly 10 is correctly connected to the console. If the user does not enter the name and identification of the patient, e.g., leaves the Patient Name and Patient ID fields blank, the user is presented with the blank patient information user interface screen. The blank patient information user interface screen allows the user to select to proceed without the entering the patient information or to enter the patient information. If the user selects to enter the patient information, the user can be re-directed to the patient information user interface screen. If the user selects to proceed without entering the patient information, the procedure main user interface screen is displayed to the user and the console 23 begins receiving video data from the imaging assembly 18 of the feeding tube assembly so long as the feeding tube assembly 10 is correctly connected to the console. If the feeding tube assembly 10 is not connected or is incorrectly connected to the console, the user is presented with an error message.

In one embodiment, the patient information may be manually entered by the user. In another embodiment, the console 23 may include a bar code scanner (not shown) for scanning the patient's bar code wristband to obtain the patient information. In yet another embodiment, the patient information can be provided on the electronic memory component 243. After communicatively connecting the feeding tube assembly 10 to the console 23, the console may read and record the patient information from the electronic memory component 243. This embodiment may be combined with the bar code scanner embodiment and/or the manual-input embodiment to provide a cross-check for the patient to ensure that the correct medical procedure, e.g., enteral feeding, is being provided to the correct patient.

Figure 20:
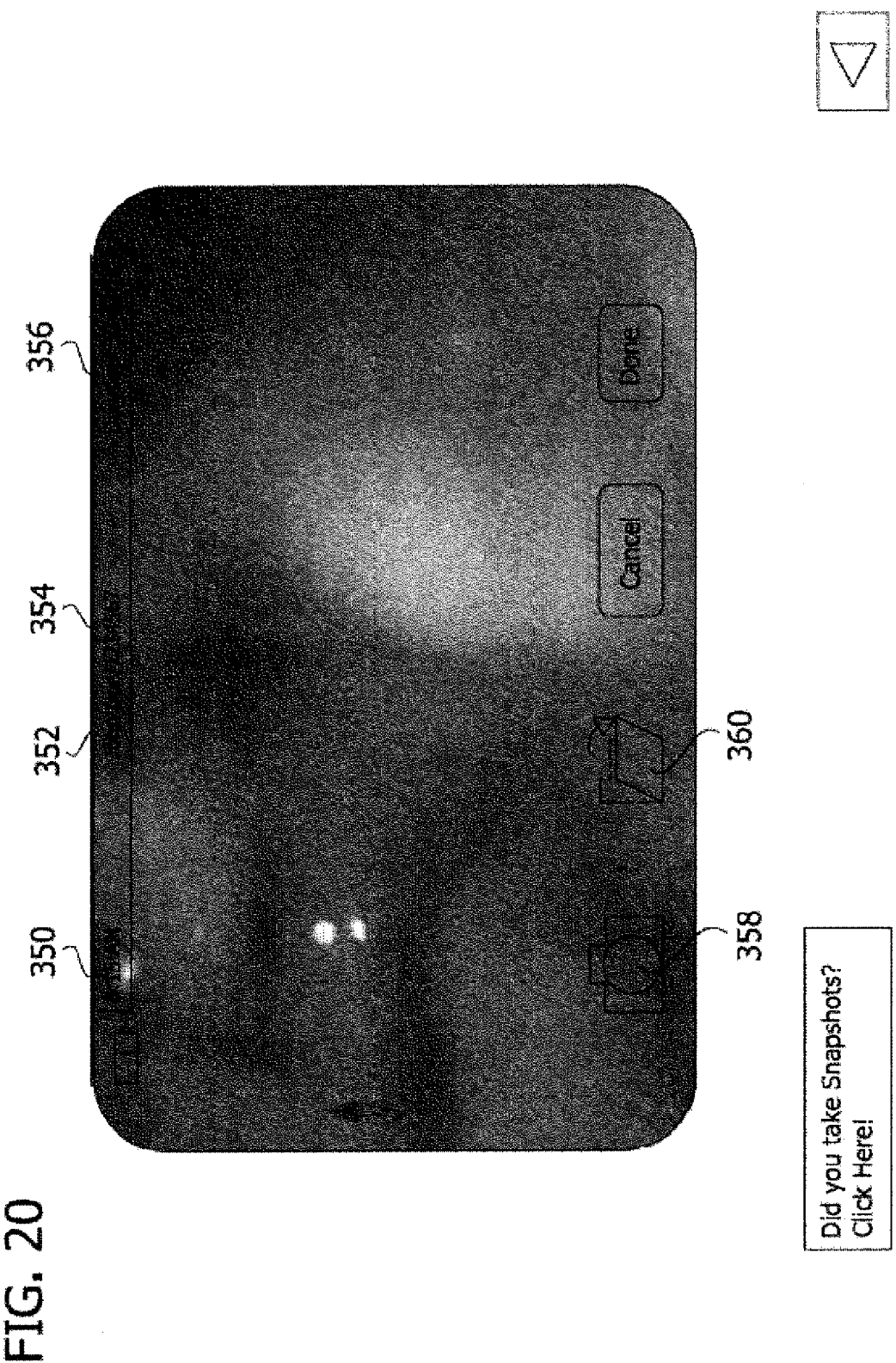
FIGS. 20-31 are schematic illustrations showing exemplary graphical user interface screens displayable by a console, in accordance with one or more aspects of the invention.
Figure 21:
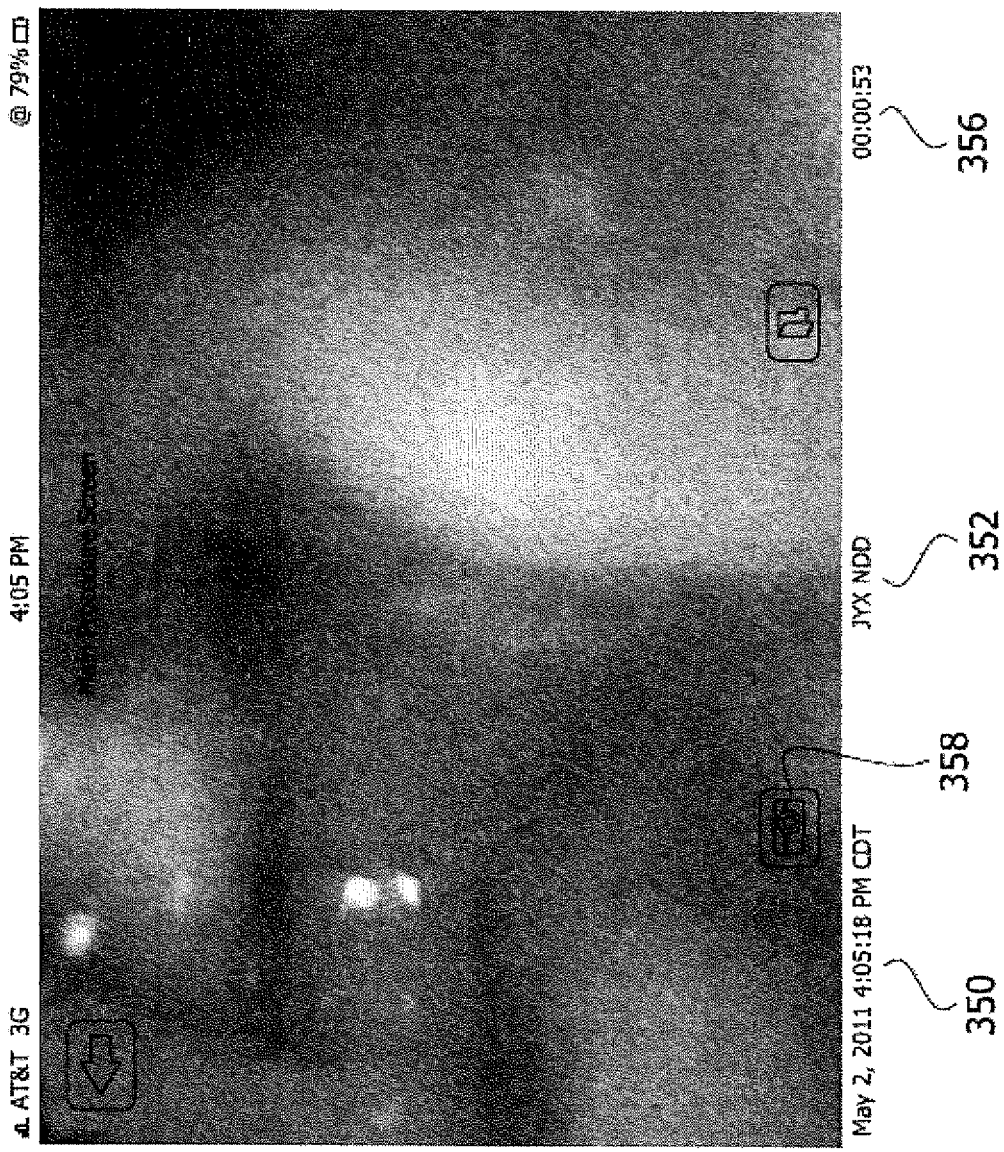
Figure 22:
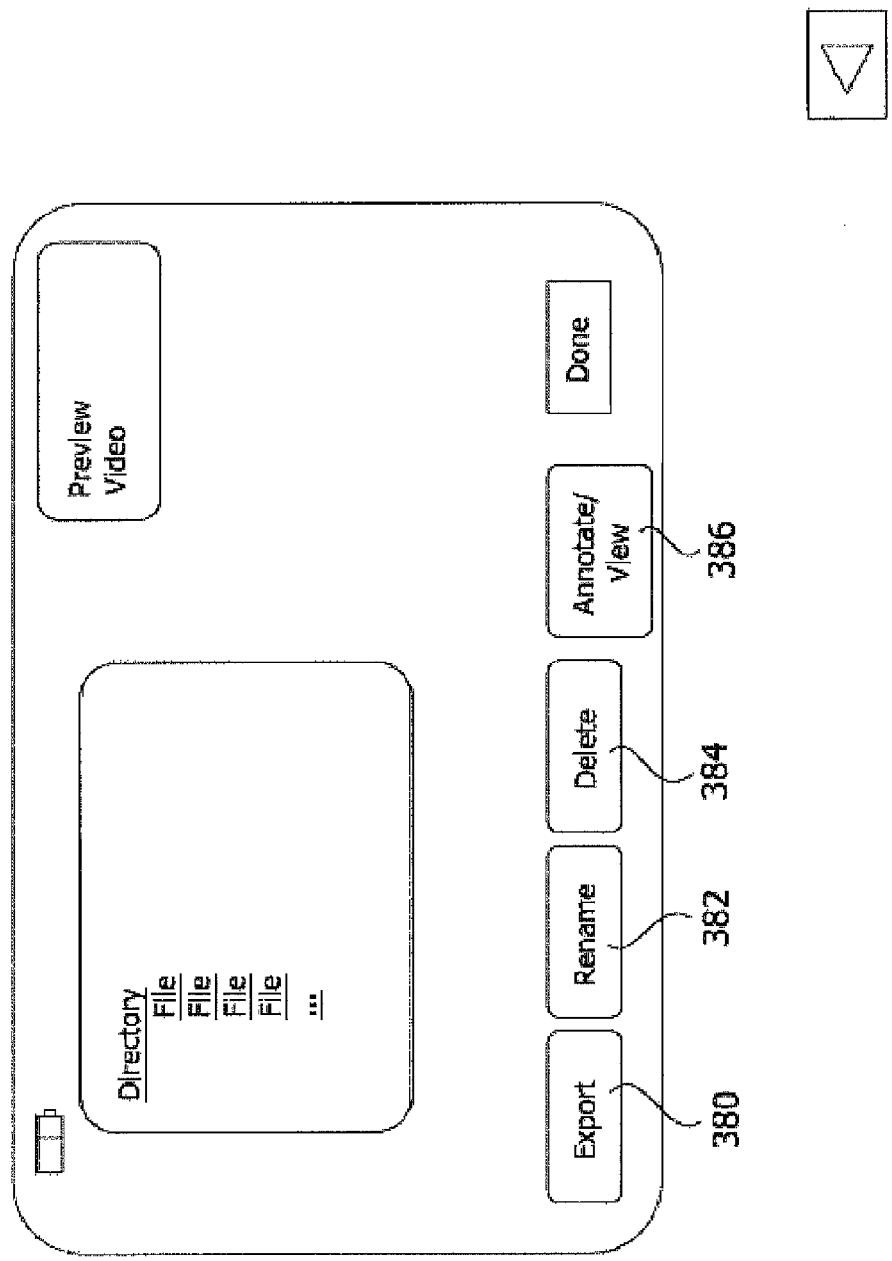
Figure 23:
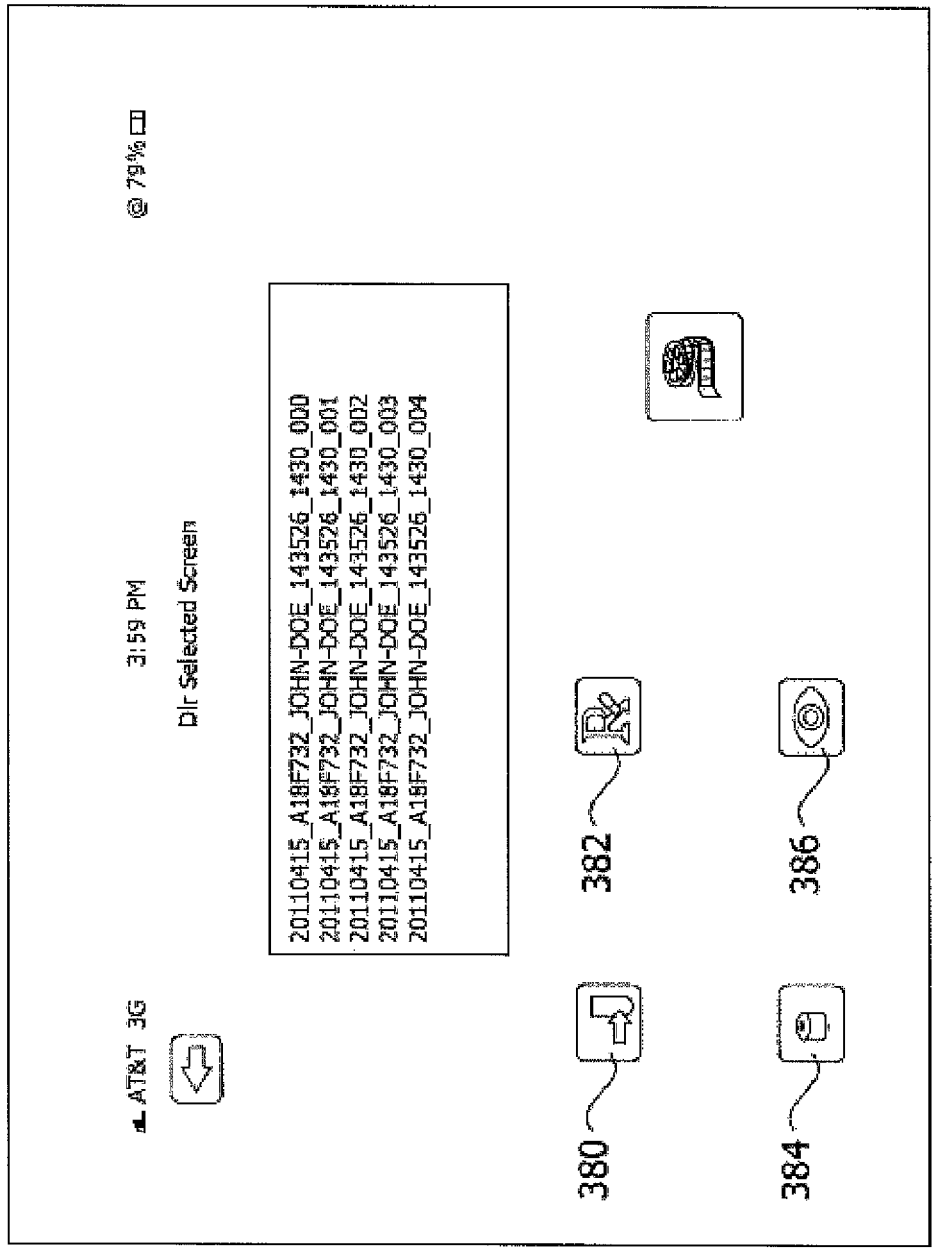
Figure 24:
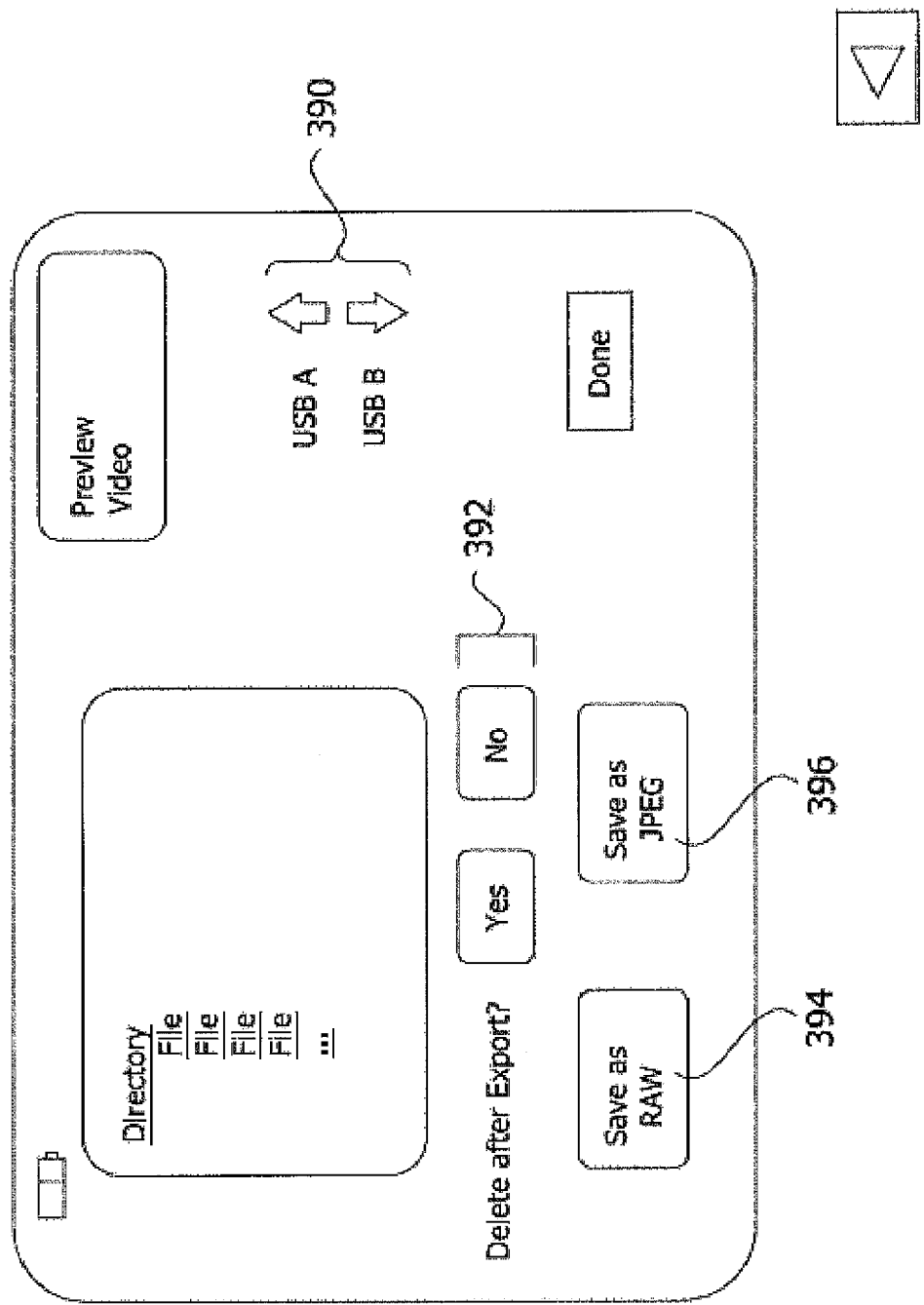
Figure 25:
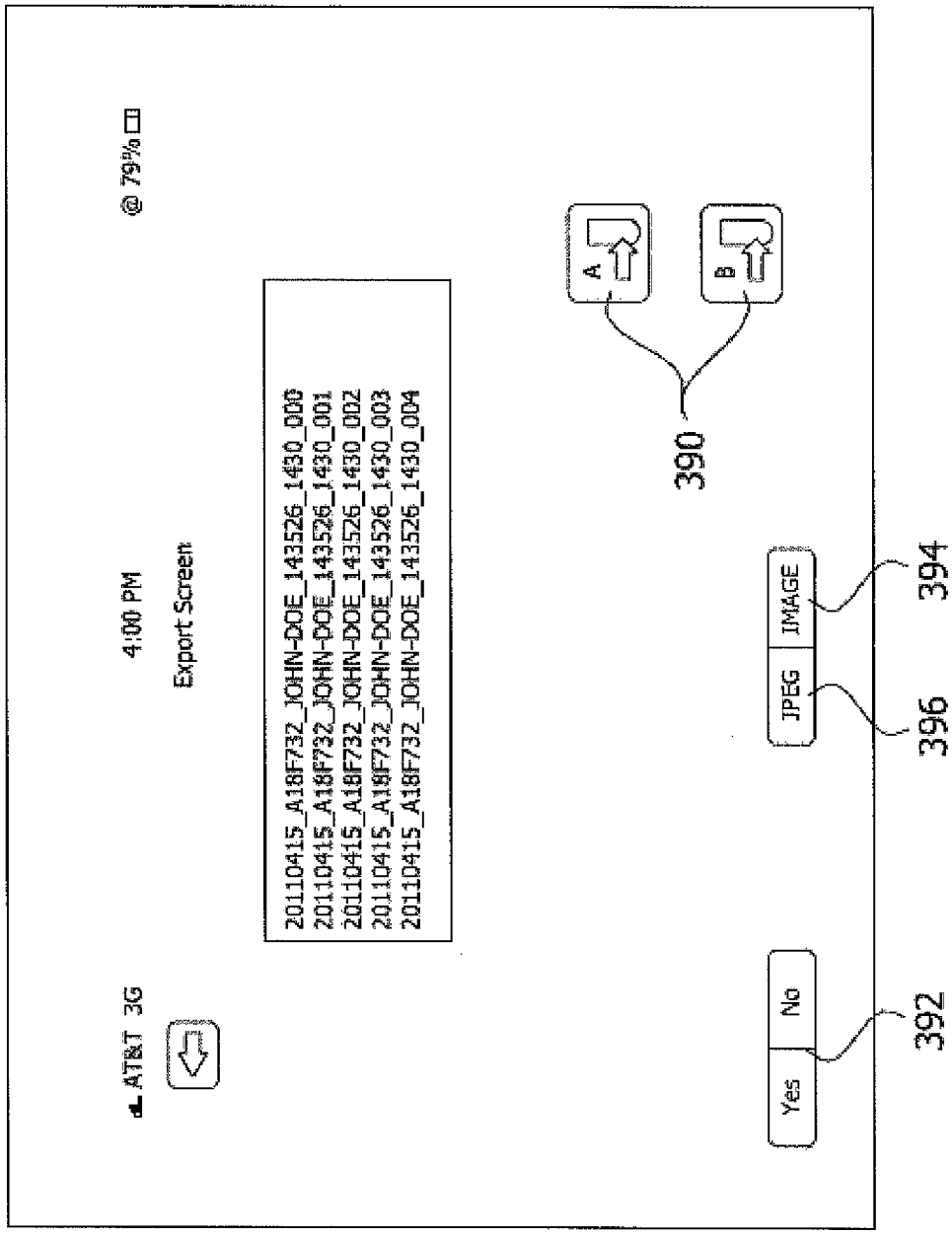

As illustrated in FIGS. 20 and 21, alternative procedure main user interface screens can display the video data or the rendered or processed imaging data being received by the console 23 from the imaging assembly 18. The procedure main user interface screen also can display any of the current time if selected by the user at 350, the patient name and identification number if entered by the user at 352 and 354, respectively, and the time elapsed for the current procedure if selected by the user at 356. The time elapsed for the current procedure begins when the user enters the patient name and identification or selects to proceed without entering the patient name and identification. The procedure main user interface screen also includes an option, e.g., icon or button with text, for taking a snapshot at 358. The snapshot option 358 allows a user to select to store the current frame of the video data or the rendered imaging data collected by the console from the imaging assembly 18. Identifying information about the snapshot may be automatically provided and/or entered by the user on the console for later identification of the snapshot. As disclosed above, the interface cable 242 may include a control device 248, which may be provided in addition to or in lieu of the snapshot option 358 on the console 23. At 360, the procedure main user interface screen provides the user with the file functions option (labeled "File Functions" or illustrated as a folder icon) which allows the user to access files stored by the console. The "File Functions" option may also be accessed directly from the main selection user interface screen. Upon selecting the "File Functions" options from either the procedure main user interface screen of FIGS. 19A and 19B, for example, or the main selection user interface screen, the user is directed to the file functions user interface screen.

The file functions user interface screen presents a user with a list of directories stored on the console, and also includes the "Preview Video" feature discussed above. Each directory represents the video data or the rendered imaging data that is stored in connection with one particular feeding tube assembly 10. In one embodiment, the console 23 can read a serial number or other unique identifier from the console connector 22. The serial number or other identifier may be specific to the feeding tube assembly 10 such that it distinguishes it from all other feeding tube assemblies. In the illustrated embodiment, the console connector 22 includes the electronic memory component 243 that stores the identifier for the feeding tube assembly 10. All of the data that is received from the feeding tube assembly 10 having a particular serial number or other identifier can be stored under a single directory in the console 23. Data that is received from a feeding tube assembly 10 having a different serial number or other identifier can be stored under a different directory.

A user may select a directory for viewing and/or editing from the file functions user interface screen. When the directory is selected from the file functions user interface screen, the user is directed to the file functions directory selected user interface screen (alternative embodiments illustrated in FIGS. 22 and 23). This user interface presents the list of files, e.g., image files, associated with the selected directory. The image files represent the images selected by the user via the snapshot option. The user is able to select at least one file from the image directory and export the file via the "Export" option 380, rename the file via the "Rename" option 382, delete the file via the "Delete" option 384, and annotate or view the file via the "Annotate/View" option 386.

If the user selects the "Export" option 380 from the file functions user interface screen, the raw/JPEG user interface screen (alternative embodiments illustrated in FIGS. 24 and 25) is displayed. This user interface presents the list of files associated with the previously selected directory and allows the user to select one or more files. The user interface allows the user to specify a particular console universal serial bus (USB) port at 390 through which the selected files will be exported. A suitable number of busses may be provided. In one embodiment two, stacked busses are provided. In another embodiment, the console 23 may additionally or alternatively be configured to export the selected files wirelessly to a receiving device and/or to export the selected files to the receiving device via an Ethernet connection. At 392, the user is also presented at 392 with the option to delete the selected files from the console once the selected files have been exported. At 394 and 396, respectively, the user is prompted to select whether to export the file as an uncompressed file, e.g., raw file, or to export the file as a compressed file, e.g., JPEG file.

If the user selects the "Rename" option 382 from the file functions user interface screen, a rename user interface screen is presented to the user to allow the user to rename the file. In one embodiment the default format of the file is DATE_SUD-SN_PT-NAME_PTID_TIME_SEQ#.img, wherein DATE=the current date (e.g., yyymmdd) set to the console via the "Date/Time" feature SUD-SN=single use device serial number (e.g., the identifier retrieved by the console 23 from the console connector 22)

PT-NAME=patient name as entered by the user via the patient information user interface screen PT-ID=patient identifier as entered by the user via the patient information user interface screen TIME=the current time (e.g., hhmmss) set to the console via the "Date/Time" feature SEQ#=the image number as received from the imaging assembly, wherein the first image sent from the imaging assembly has an image number of 1 and the image number for each image received thereafter is incremented by one.

In one embodiment, the "Rename" option 382 allows the user to change only the SEQ# portion of the file name.

If the user selects the "Delete" option 384 from the file functions user interface screen, the delete user interface screen is presented to the user to allow the user to delete files. The delete user interface screen can provide the user with a list of the files included in the previously selected directory. The user can select one more files from the directory and then select the delete option, e.g., delete button or icon. When the user selects the delete option from the delete user interface screen, the user is prompted via the delete confirmation user interface screen, to confirm that the selected files should be deleted from the console. Once the user confirms that the selected files should be deleted, the selected filed are deleted from the console.

Figure 26:
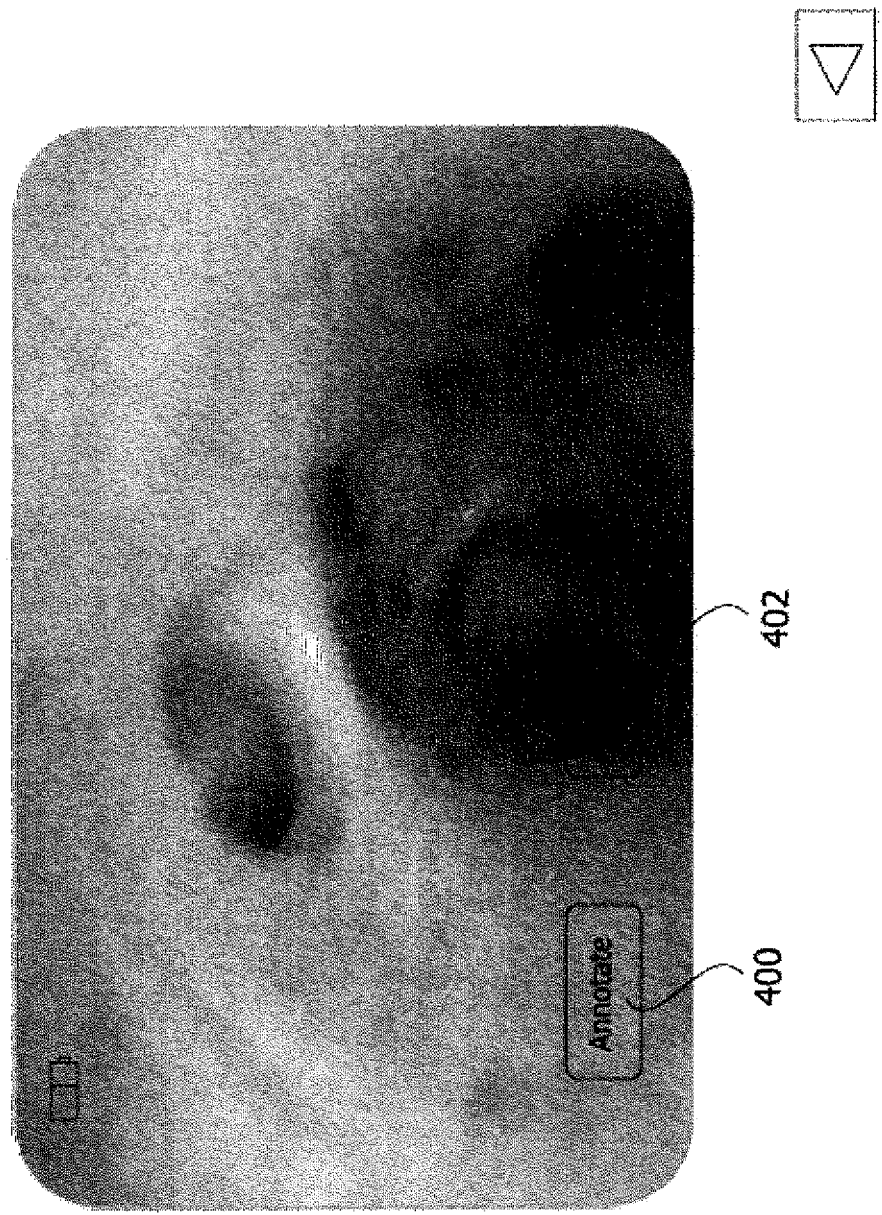
Figure 27:
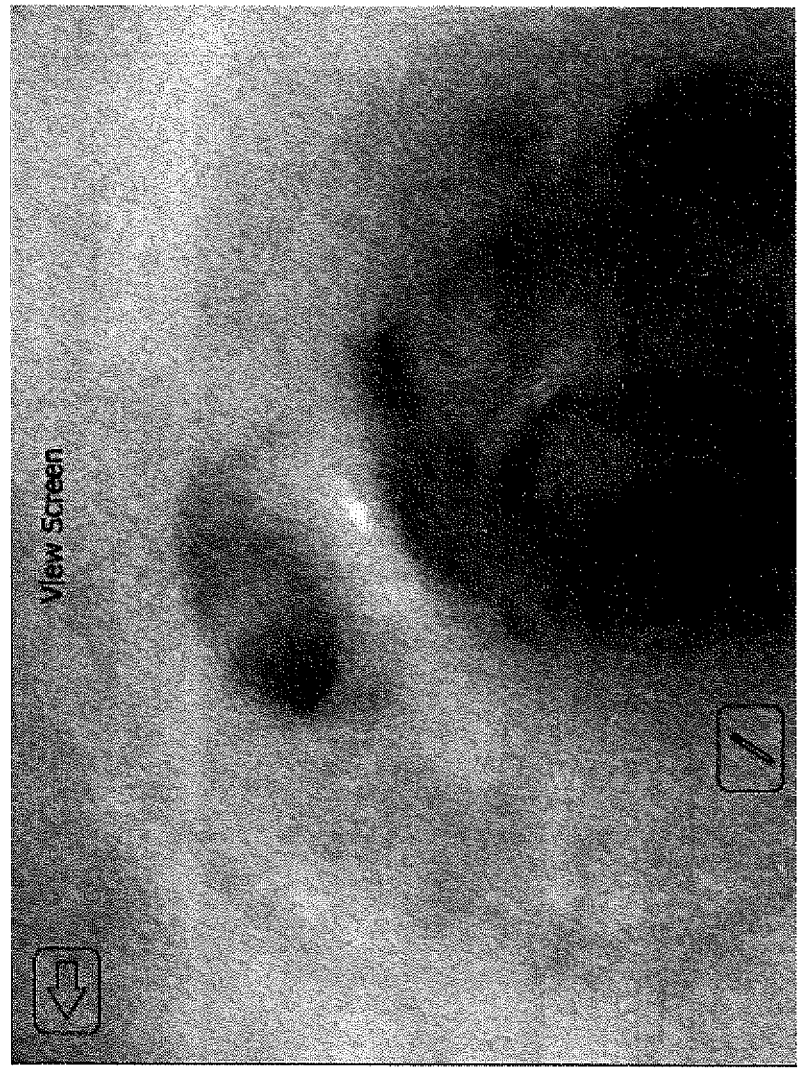
Figure 28:
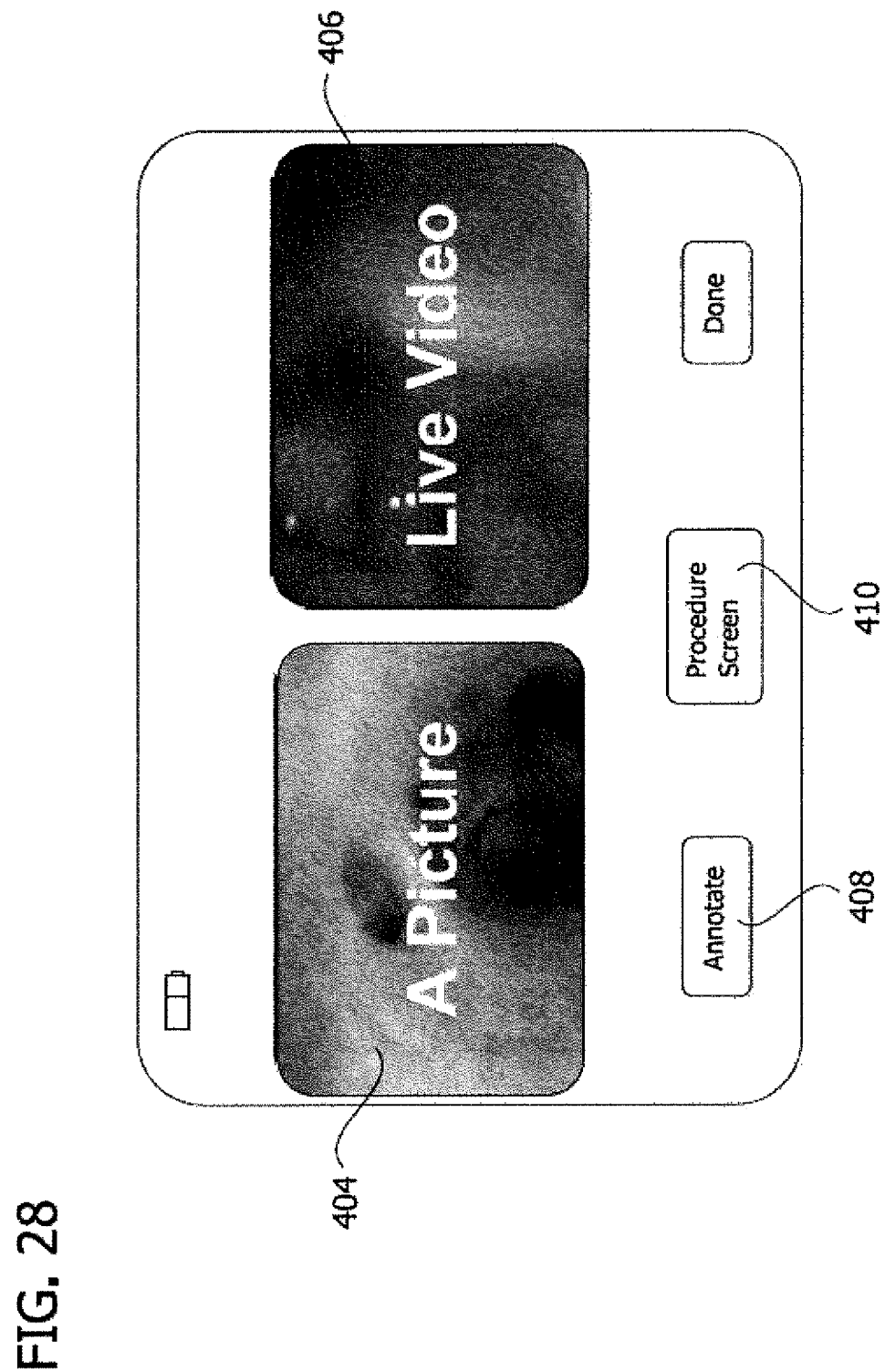
Figure 29:
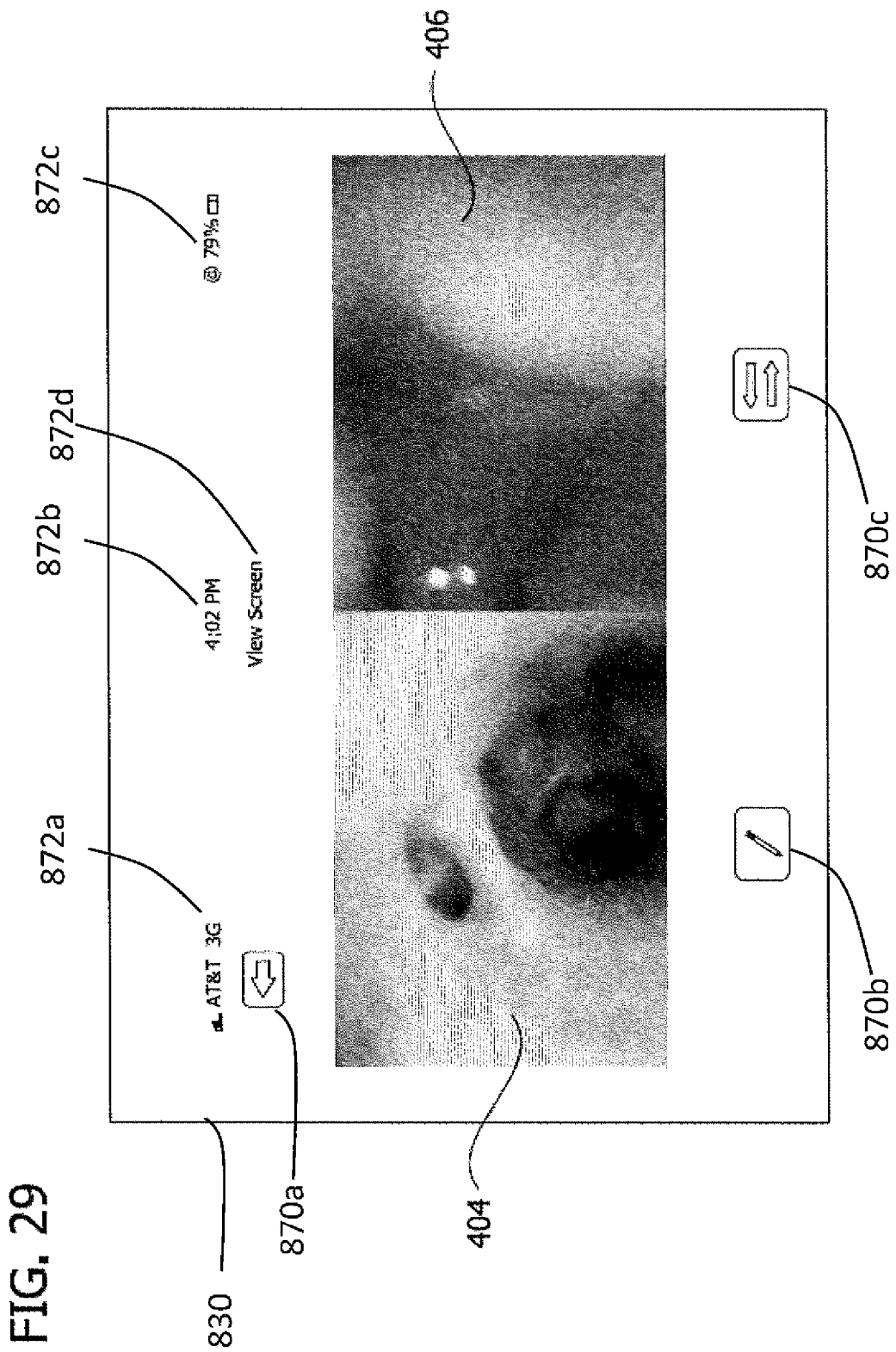
Figure 30:
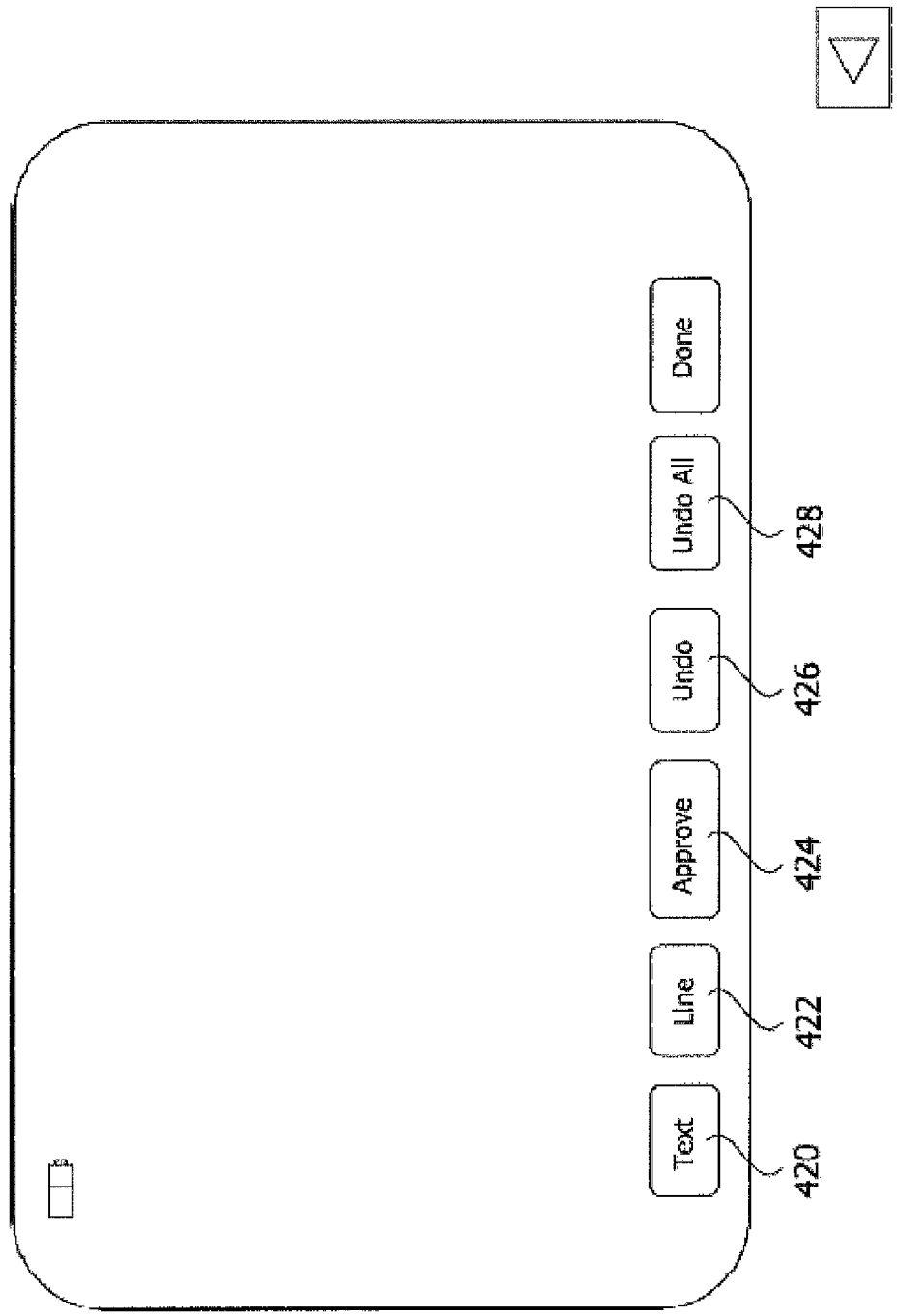

If the user selects the "Annotate/View" option 386 from the file functions user interface screen, a view user interface screen as shown in the alternative embodiments of FIGS. 26 and 27 is displayed. The view user interface screen can display the image stored in the selected file. The view user interface screen also can provide the user with an "Annotate" option at 400 and a "Compare to Video" option at 402. If the user selects the "Compare to Video" option at 402, the console 23 presents a compare user interface screen to the user (alternative embodiments illustrated in FIGS. 28 and 29). A first portion 404 of the compare user interface screen displays the image stored in the selected file. A second portion 406 of the compare user interface screen can display video data or rendered imaging data currently being received by the console from the imaging assembly 18. The images on both the first and second portions 404, 406 can in one embodiment be zoomed or panned. By comparing a previously captured image illustrating prior tube placement within a patient to current video data illustrating current tube placement within the patient, a user can determine whether the tube has migrated within the patient. Additionally or alternatively, a user can compare an image of a previously placed tube to current information representative of a current tube placement to facilitate assessment as to whether the tube currently appears to be placed appropriately. It should be noted that the first portion 404 and the second portion 406 of the compare user interface screen are illustrated as being horizontally aligned; however, the first and second portions, 404 and 406 maybe alternatively arranged with respect to one another, e.g., vertically aligned, and may be modified by the user without departing from the scope of the invention.

The compare user interface screen provides the user with an "Annotate" option at 408 and a "Procedure Screen" option at 410. If the user selects the "Procedure Screen" option 410, the console redirects the user to the patient information user interface screen described above. If the user selects the "Annotate" option 408 from the compare user interface screen (FIGS. 28 and 29), or the "Annotate" option 400 from the view user interface screen (FIGS. 26 and 27), the console presents the user with an annotate user interface screen illustrated in the alternative embodiments of FIGS. 30 and 31. The annotate user interface screen presents the user with a "Text" option at 420, and "Line" option at 422, and "Approve" option at 424, an "Undo" option at 426, and an "Undo All" option at 428.

If the user selects the "Text" option 422, the annotate user interface screen allows the user to indicate, e.g., by touching or clicking, the portion of the image being displayed on the annotate user interface screen where the user would like to place the center of the text. After receiving the user input indicating the location of the text, the annotate user interface screen displays additional options to the user. In particular, the annotate user interface screen provides the user with the option to select text naming an anatomical structure from a text list of anatomical structures. The annotate user interface also provides the user with the option to add free-text to the image. If the user selects text naming an anatomical structure from the text list, the selected text appears on the screen centered over the user-selected text location. If the user selects to add free-text to the image, the annotate user interface screen adds a keyboard to the annotate user interface screen and allows the user to enter text accordingly. If the keyboard on the annotate user interface screen covers the user-selected text location, the text entered by the user is moved upward until the user finishes entering the text. Once the text entry has been completed, the entered text can be displayed on the screen centered over the user-selected text location.

If the user selects the "Line" option 422 the annotate user interface screen allows the user to indicate, e.g., by touching or clicking, the portion of the image being displayed on the annotate user interface screen where the user would like to place a first end of a line segment. The user may then indicate, e.g., via a drag and drop operation, where the second end of the line segment should be located on the annotate user interface screen. If the "Undo" option 426 is selected, the last unsaved annotated item, e.g., text, line segment, is removed from the image. This operation can be repeated until there are no unsaved annotated items remaining in the image. If the "Undo All" option 428 option is selected, all unsaved annotated items are removed from the image.

If the user selects the "Approve" option 424, the user can be re-directed to the approver user interface screen. The approver user interface screen prompts a user to enter his/her username and password. Once the username and password are entered, the console attempts to authenticate the user as being associated with approver status. If the user is authenticated, a message, such as "Approved by USERNAME on DATE at TIME" is added to the image, e.g., upper left of image beneath the patient identification information, wherein USERNAME=the username of the current user as entered in the approver user interface screen DATE=the current date (e.g., yyymmdd) set to the console via the "Date/Time" feature TIME=the current time (e.g., hhmmss) set to the console via the "Date/Time" feature Once an approver user has indicated that he/she approves the placement of the tube, the patient is allowed to be provided with nutrients via the feeding tube assembly 10. For example, the console may be configured to provide a signal that allows operation of feeding pump.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with computer-executable instructions. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

Figure 32A:
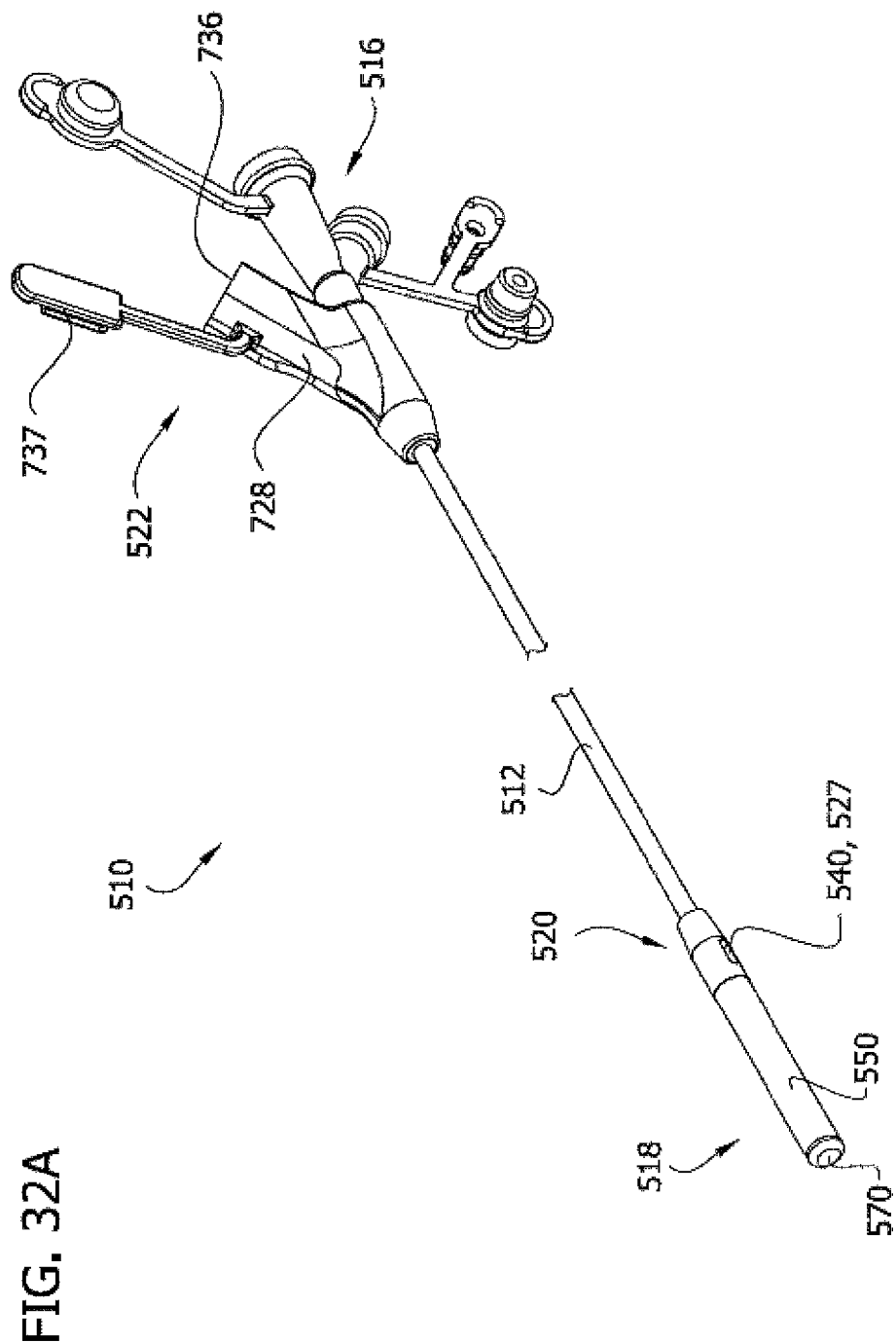
FIG. 32A is a schematic illustration showing a perspective view of an imaging feeding tube assembly, in accordance with one or more aspects of the invention.
Figure 34:
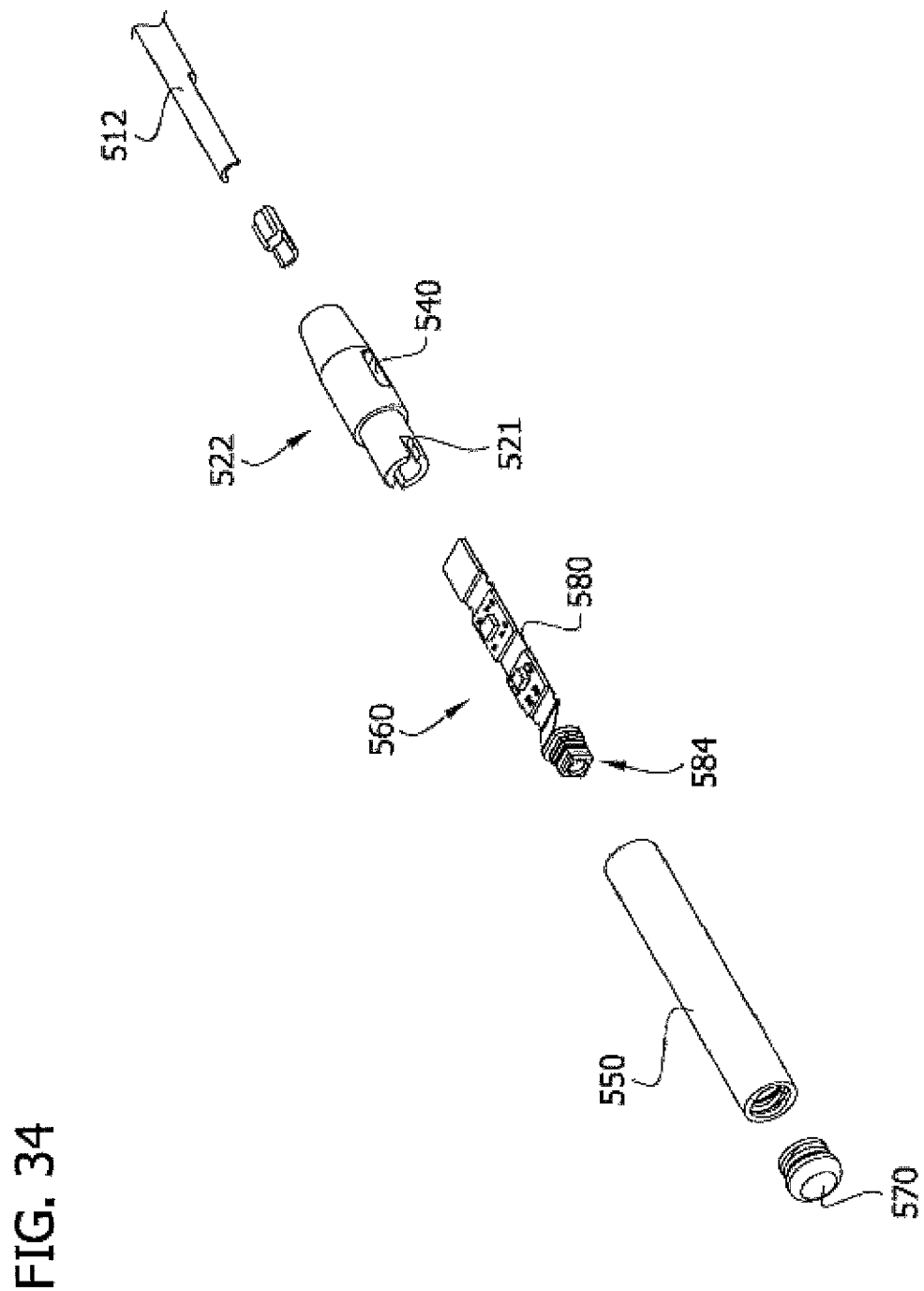
FIG. 34 is a schematic illustration showing an exploded perspective view of an imaging assembly of the imaging feeding tube assembly in FIG. 32A, in accordance with one or more aspects of the invention.
Figure 35:
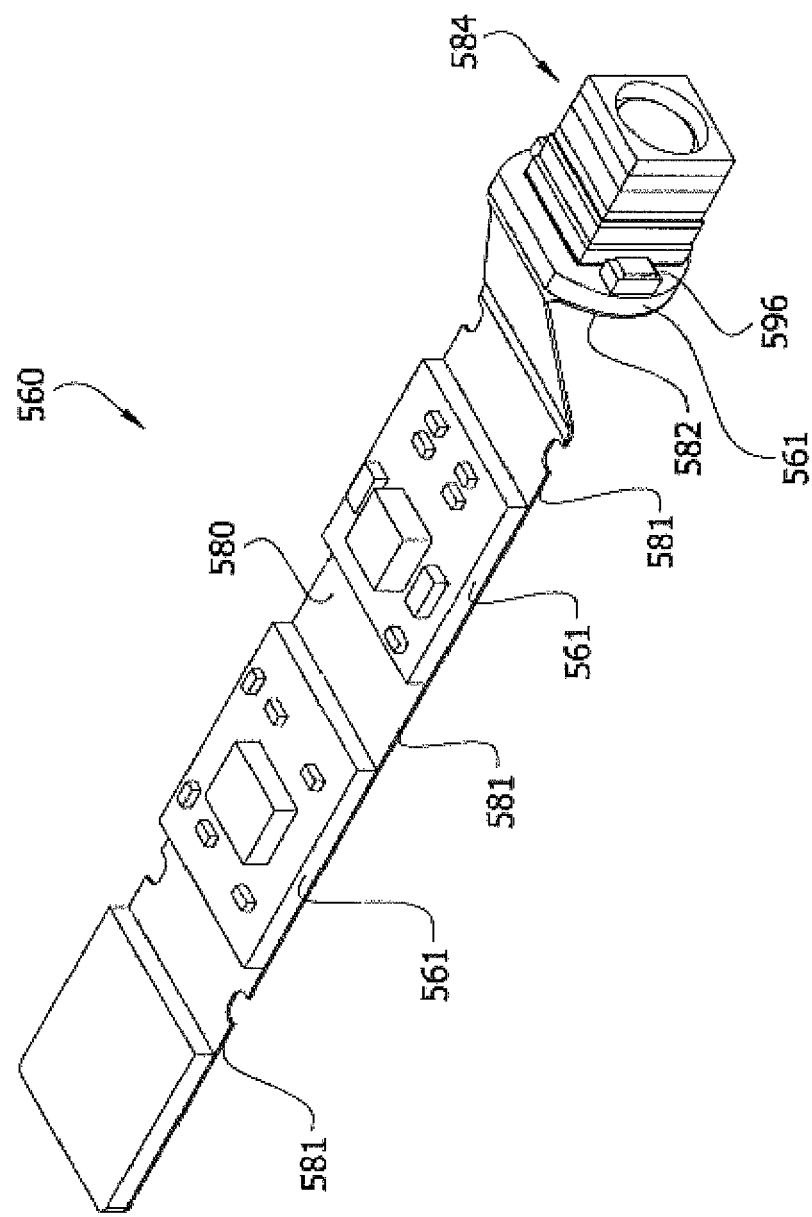
FIG. 35 is a schematic illustration showing a perspective view of a rigid-flex circuit assembly, in accordance with one or more aspects of the invention.
Figure 36:
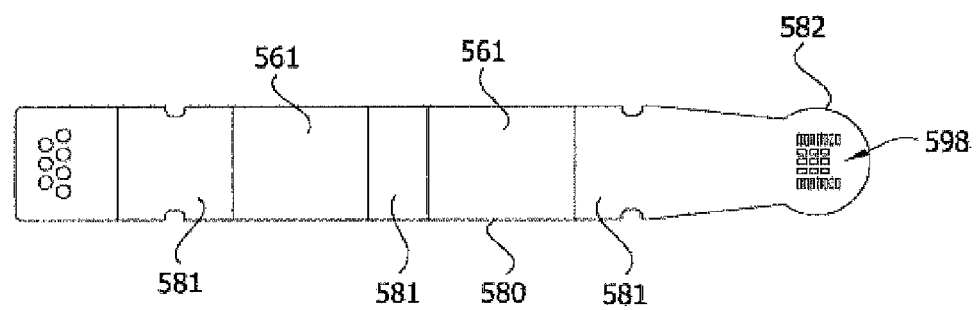
FIG. 36 is a schematic illustration showing a top plan view of a rigid-flex circuit, in accordance with one or more aspects of the invention.

Referring to FIGS. 32A-42, another embodiment of the imaging feeding tube assembly is generally indicated at 510. This embodiment is similar to the various embodiments disclosed above, and like components are indicated by corresponding reference numerals plus 500. Referring to FIGS. 32A and 32B, the imaging feeding tube assembly 510 includes a feeding tube 512, a inlet adaptor, generally indicated at 516, adjacent a second longitudinal end, i.e., a proximal end, of the tube, an imaging assembly, generally indicated at 518, adjacent a first longitudinal end, i.e., a distal end, of the tube, and a console connector, generally indicated at 522, secured to the tube intermediate the inlet adaptor 516 and the imaging assembly 518. The imaging feeding tube assembly 510 may be used with the console 23, or a different console or display, for displaying one or more images generated by the imaging assembly 518, as disclosed above. The inlet adaptor 516 is analogous to the inlet adaptor 16, and therefore, reference is made to the prior inlet adaptor for an explanation of various features of the inlet adaptor 516. Unless otherwise specified below, disclosures relating to the components of the previous feeding tube assembly embodiment 10, set forth above herein, also apply to the components of the current feeding tube assembly embodiment 512.

Figure 33:
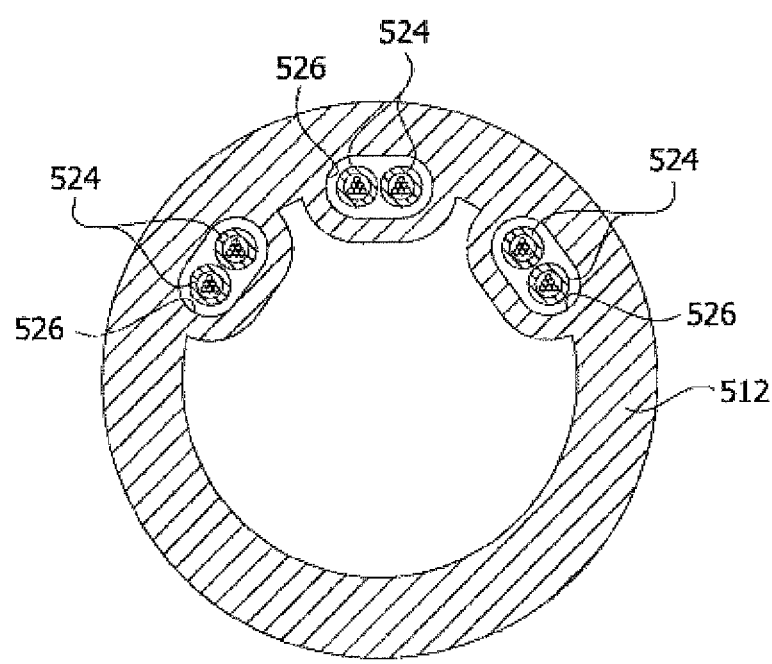
FIG. 33 is a schematic illustration showing a cross-sectional view of a feeding tube of the imaging feeding tube assembly in FIG. 32A, in accordance with one or more aspects of the invention.

The tube 512 can be a one-piece tube. Referring to FIG. 33, electrical conductors 524 (broadly, a signal transmission component) extend longitudinally along substantially the entire length of the tube 512 from the imaging assembly 518 to the console connector 522. In the illustrated embodiment, there are six electrical cables 524 for powering the imaging assembly 518 and transmitting data between the console, e.g., console 23, and the imaging assembly, although there may be more or less cables without departing from the scope of the present invention. In the illustrated embodiment the cables 524 are disposed in three separate and distinct conductor passages 526. The cables 524 are provided in pairs, with each pair being disposed within the same conductor passage 526 in the tube wall. In one example, the cables 524 and the tube 512 may be co-extruded so that the cables are embedded in the tube wall. After co-extrusion, the cables 524 may be laser ablated to remove the respective jackets and/or mechanically stripped to expose the wires so that the cables can be electrically connected to the imaging assembly 518 and the console connector 522.

Referring to FIGS. 34-37, the imaging assembly 518 can include an elongate housing 550; a flex circuit assembly, generally indicated at 560 (FIG. 35), including a camera 584 and a light source 596 mounted thereon and received in the housing; and a cap 570 attached to the camera at a first longitudinal end, e.g., distal end, of the imaging assembly. In this embodiment, a flex circuit 580 of the flex circuit assembly 560 can be a rigid-flex circuit including one or more space apart rigid structures 561 mounted on the flex circuit which inhibit bending. The electrical components, such as those described above with respect to the previous embodiment, are mounted on the rigid structures 561. The rigid-flex circuit 560 is capable of bending at bending locations 581 between the rigid structures 561 such that the rigid-flex circuit is capable of selectively deforming solely at the bending locations 581 along the length of the folded rigid-flex circuit. The light source 596 and the camera 584 are mounted on the same distal camera-mounting portion 582 of the rigid-flex circuit 560, which extends generally transverse to the longitudinal axis of the imaging assembly 518. In the illustrated embodiment, the camera-mounting portion 582 can have one of the rigid structures 561 mounted thereon, to which the camera 584 and the light source 596 can be secured.

Electrical components for operating the imaging assembly 518 may be similar or the same as the electrical components disclosed above for operating the previous embodiment of the imaging assembly 18. In addition to those electrical components, the rigid-flex circuit 560 includes decoupling capacitors, generally indicated at 598, for providing a stable supply voltage with low noise to the camera 84. In the illustrated embodiment, the decoupling capacitors 598 are embedded in the camera-mounting portion 582 of the rigid-flex circuit 560 between layers thereof. In this way, the decoupling capacitors 598 are immediately adjacent the camera 584.

Figure 40:
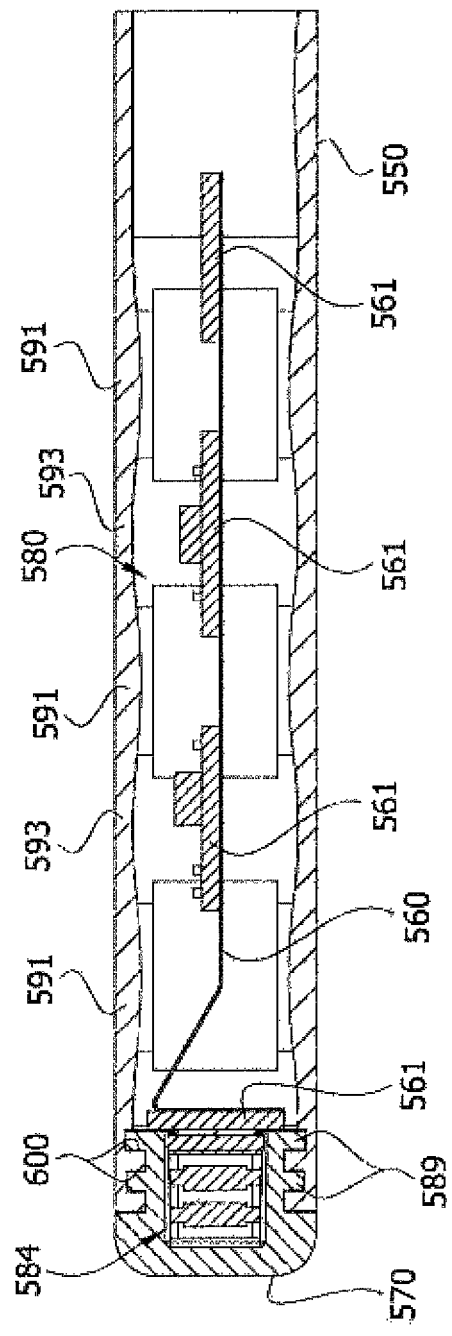
FIG. 40 is a schematic illustration showing a longitudinal section view of the housing of the imaging assembly in FIG. 34, in accordance with one or more aspects of the invention.
Figure 42:
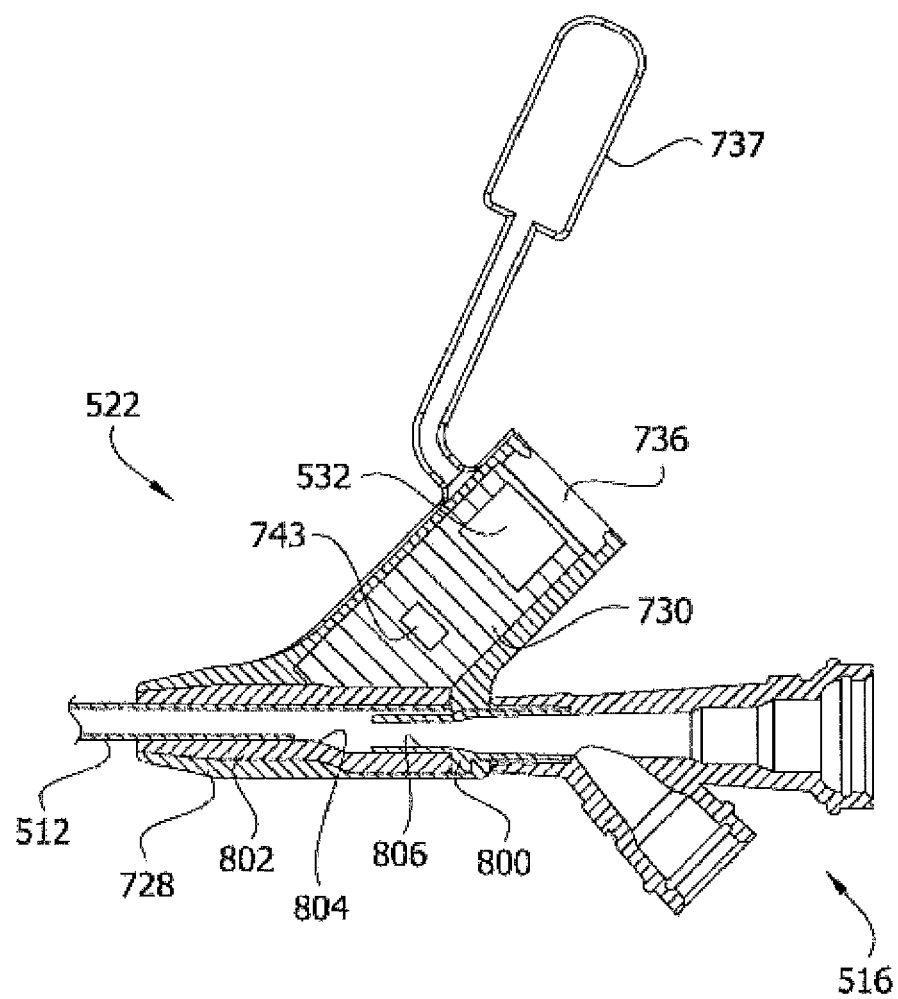
FIG. 42 is a schematic illustration showing a cross-sectional view of a console connector of the imaging feeding tube assembly, in accordance with one or more aspects of the invention.

Referring to FIGS. 40 and 42, the cap 570 may be similar to the cap 70 except that the cavity in the cap 570 is typically sized and shaped for receiving the camera 584 only, without the camera and the LED 596 as in the previous embodiment. In addition, referring to FIG. 40, the cap 570 includes a plurality of radial locking ribs 589 received in corresponding radial locking grooves 600 formed on the interior surface of the housing 550. The engagement between the locking ribs 589 and the locking grooves 600 inhibit longitudinal movement between the housing 550 and the cap 570. The cap 570 may be of other configurations without departing from the scope of the present invention.

In one non-limiting example (FIG. 40), the housing 550 may be molded and include longitudinally spaced apart reinforcing structures 591, i.e., wall portions of housing 550 with increased thicknesses, and bending locations 593 with wall thickness of housing 550 less that at structures 591 disposed between the reinforcing structures. The reinforcing structures 591 are typically disposed adjacent the electronic components and the rigid structures on the rigid-flex circuit 580, while the bending locations 593 are typically disposed adjacent the bending locations on the rigid-flex circuit. Through this configuration, the cap 550 further promotes bending of the imaging assembly 518 at selected locations along its length and inhibits bending at longitudinal locations where the electronic components are located. The difference in wall thickness of housing 550 with respect to structures 591 and locations 593 can be less than about 25%, less than about 10%, or less than about 5%.

In another non-limiting example (FIG. 41), the housing 550 may be molded over the cap 570, the rigid-flex circuit assembly 560, and the imaging assembly connector 520 to form an integral imaging assembly 518. For example, the cap 570, the rigid-flex circuit assembly 560, and the imaging assembly connector 520 may be placed in a fixture of an overmolding process, and then the housing 550 may be molded over the components. The material for overmolding may comprise urethane or other material. In yet another embodiment, the housing 550 may be pre-formed and the cap 570 and the imaging assembly connector 520 may be secured to the respective ends of the housing, such as by solvent bonding or in other suitable ways.

Figure 38:
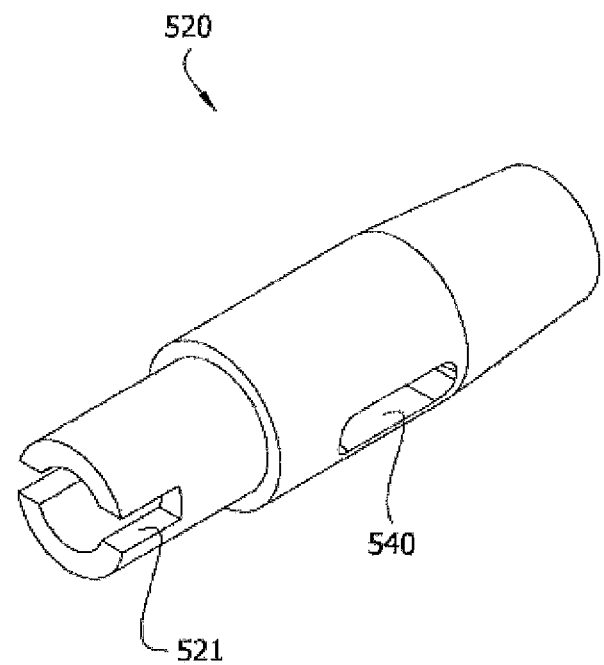
FIG. 38 is a schematic illustration showing a perspective view of an imaging assembly connector of the imaging feeding tube assembly in FIG. 32A, in accordance with one or more aspects of the invention.
Figure 41:
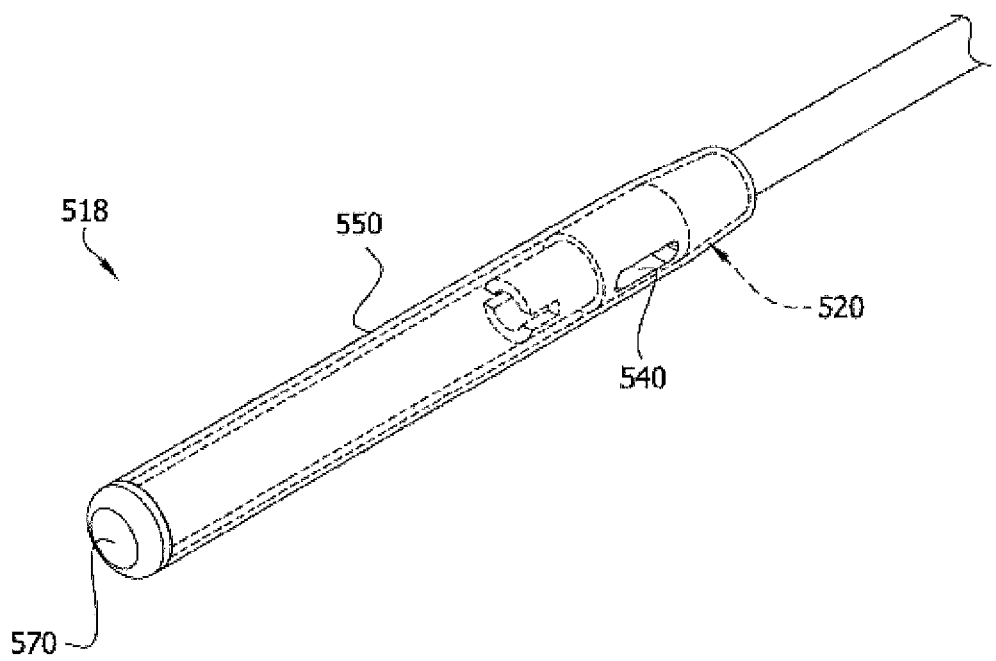
FIG. 41 is a schematic illustration showing an imaging assembly, in accordance with one or more aspects of the invention.

Referring to FIGS. 32A, 32B, 38, and 39, as with the previous feeding tube assembly 10, the current feeding tube assembly 510 includes an imaging assembly connector, generally indicated at 520. Like the previous embodiment of the imaging assembly connector 20, the current imaging assembly connector 520 defines a feeding passage outlet 540 that is in fluid communication with the feeding passage 514 of the tube 512. In the illustrated embodiment, the first longitudinal end of the tube 512 is received and secured in the feeding passage outlet 540 of the imaging assembly connector 520 to provide fluid communication therebetween. The outlet 540 is closed adjacent to prevent liquid nutrients from entering the imaging assembly 518. Thus, the imaging assembly 518 is not in fluid communication with the feeding passage 514. Instead, the feeding solution is dispensed laterally from the outlet 540 and to the patient (only one such lateral opening is shown in FIGS. 32 and 38).

Figure 39:
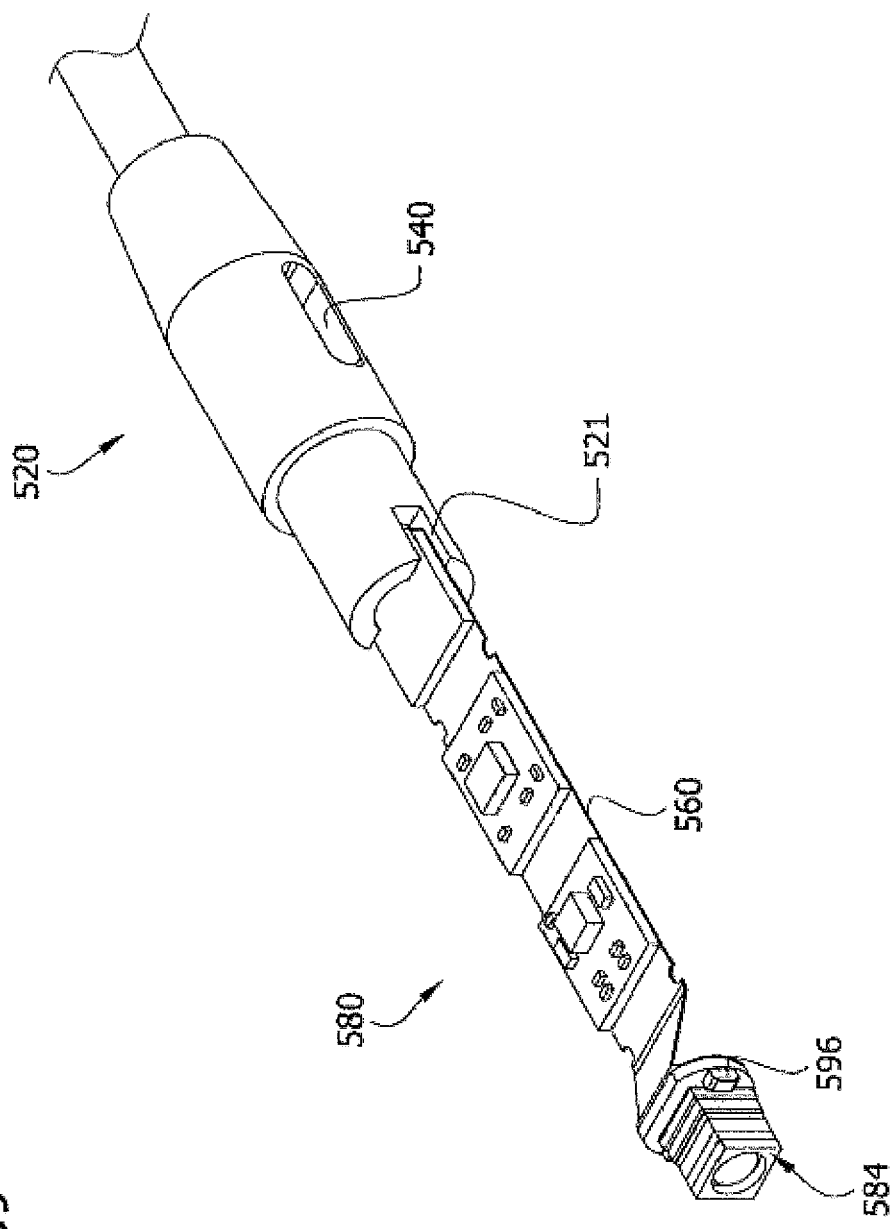
FIG. 39 is a schematic illustration showing a perspective view of the imaging assembly in FIG. 34, with a housing removed therefrom to show internal components, in accordance with one or more aspects of the invention.

Referring to FIGS. 38 and 39, a first longitudinal end, e.g., a distal end, of the imaging assembly connector 520 defines an alignment slot 521 for receiving a proximal end of the rigid-flex circuit assembly 560. The alignment slot 521 facilitates proper positioning of the rigid-flex circuit assembly 560 relative to the imaging assembly connector 520. The imaging assembly connector 520 may be of other configurations without departing from the scope of the present invention.

Referring to FIG. 42, the console connector 522 can be secured to the feeding tube 512 and can extend laterally outward therefrom. The present illustrated console connector 522 includes a housing 728, and a PCB 730, an inlet adaptor connector 800, and a feeding tube connector 802 secured to the housing. A connector, such as a USB port connector 532, may be mounted on the PCB 730 for communicatively connecting an interface cable to the PCB 730. In another embodiment, the PCB 730 may include an edge connector, as disclosed above with respect to the previous embodiment. An electronic memory component 743 may be mounted on the PCB 730. The housing 728 can define a socket 736 having a size and shape for mateably receiving an interface connector (not shown) having a corresponding size and shape. A connector cap 737 can be tethered to the housing 728 for selectively closing the socket 736 when it is not in use.

The housing 728 may be molded over the inlet adaptor connector 800 and the feeding tube connector 802 to secure the connectors to the housing. The proximal end of the feeding tube 12 is secured within a connection passage 804 in the feeding tube connector 802. The inlet adaptor connector 800 connects the inlet adaptor 516 to the console connector 522 and defines a passage 806 that fluidly connects the inlet adaptor 516 to the feeding tube 512. In another embodiment (not shown), the one-piece feeding tube 512 may pass through an opening in the console connector 522 and connect directly to the inlet adaptor 516. The housing 728 may be secured to the feeding tube 512 using adhesive or in other ways. The housing 728 may be secured to the inlet adaptor 516, more specifically, to the distal end of the inlet adaptor so that the housing abuts the inlet adaptor. The console connector 522 may have other configurations without departing from the scope of the present invention.

Figure 43:
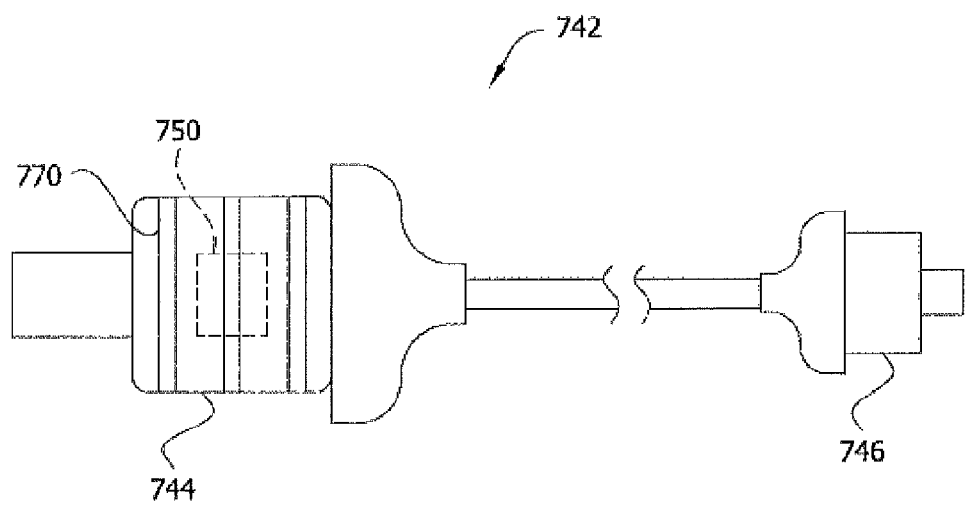
FIG. 43 is a schematic illustration showing an interface cable, in accordance with one or more aspects of the invention.
Figure 37:
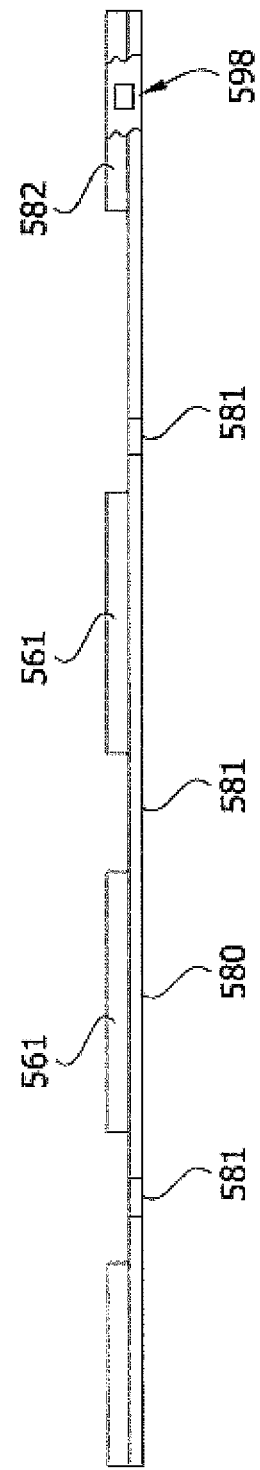
FIG. 37 is a schematic illustration showing a side, elevational view of a rigid-flex circuit, in accordance with one or more aspects of the invention.

Referring to FIG. 43, another embodiment of an interface cable for connecting the feeding tube assembly 10, 510 to the console 23 is indicated at 742. The interface cable 742 is similar to the interface cable 242 of the previous embodiment. Like the previous interface able embodiment 242, the present interface cable 742 can include first and second interface connectors 744, 746 on opposite ends of the cable. The illustrated first interface connector 744 is sized and shaped to mate, e.g., to be selectively inserted into, the socket 736 of the console connector 522 and to make connection with the USB port connector 532, or an edge connector or another connector associated with the console connector. The first interface connector 744 includes annular ribs or beads 770 that engage an interior surface of the socket 736 to form a substantially liquid-tight seal therewith to prevent the ingress of fluid into the socket. The second interface connector 746 is sized and shaped to mate, e.g., to be selectively inserted into, with a corresponding socket of the console 23 and to make connection with the console. The first and second interface connectors 744, 746 and the corresponding sockets 736 can be configured so that the first interface connector 744 is not mateable with the socket on the console 23 and the second interface connector 746 is not mateable with the socket 736 of the console connector 522. The interface cable 742 may be of other configurations without departing from the scope of the present invention.

In the illustrated embodiment, first interface connector 744 can include an imaging signal buffer component 750, e.g., an I$^2$C buffer component, which drives imaging signals, e.g., I$^2$C signals, between the imaging assembly 18, 518 and the console. By locating the imaging signal buffer component 750 in the first interface connector 744, the capacitance is split approximately equally between the conductors 24, 524, e.g., wires in the cables, in the feeding tube assembly 10, 510 and the conductors, e.g., wires, in the interface cable 742. This configuration minimizes or reduces capacitance in any one segment of the system and maximizes or improves the image signal integrity. Moreover, the first interface connector 744 and the imaging signal buffer component 750 will be desirably adjacent the feeding tube assembly 10, 510 because the console connector 22, 522 is mateable only with the first interface connector, and not the second interface connector 746. The interface cable 742 may not include an imaging signal buffer component 750 and may be of other configurations without departing from the scope of the present invention.

One or more aspects of the invention can involve a catheter can be feeding tube having an imaging assembly with an imaging device or sensor. The imaging assembly can generate and transmit imaging signals generated by the imaging device. The system can include a console adapted to receive the imaging signals and present images corresponding to the imaging signals on a display. Further, the console can be configured to selectively present a reference menu on the display including menu items. The menu items correspond to reference materials comprising any one or more of photographs, video recordings, audio recordings, diagrams, animations, and text. The materials provides information about any one or more of anatomy, patient preparation, imaging catheter preparation, imaging catheter placement, imaging catheter operation, imaging catheter features, console preparation, console operation, console features, system operation, system features, contact information, help information, and support information. One or more aspects of the invention can be directed to an imaging catheter system, comprising a feeding tube having an inlet connectable to a source of feeding fluid, an outlet distal from and fluidly connected to the inlet through a feeding passage, and an imaging device disposed proximate the outlet, the imaging device configured to generate and transmit imaging signals corresponding to an image of an anatomy of a patient; and a console comprising a display and memory having stored therein a plurality of reference materials selected from the group consisting of audiovisual data such as videos, audio, and photographs, textual data such as diagrams, animations, and text, and combinations thereof. In some cases, each of the plurality of reference materials can provide information about at least one of anatomy, patient preparation, imaging catheter preparation, imaging catheter placement, imaging catheter operation, imaging catheter features, console preparation, console operation, console features, system operation, system features, and contact information. Preferably, the console is configured to receive the imaging signals, present at least a portion of at least one image corresponding to the imaging signals on the display, and present a reference menu on the display including menu items corresponding to at least one of the reference materials. The at least one of the plurality of reference materials can include a photograph showing an anatomical landmark. The anatomical landmark can be one of a bronchus, larynx, a tracheal ring, cardia, pyloric sphincter or pylorus, cricoid cartilage, bronchial split, esophageal junction, stomach folds, duodenal folds, and a pyloric orifice.

One or more further aspects of the invention can be directed to a method of facilitating use of or providing a feeding tube assembly. The method can comprise providing a feeding tube having an inlet connectable to a source of feeding fluid, an outlet distal from and fluidly connected to the inlet through a feeding passage, and an imaging device disposed proximate the outlet, the imaging device configured to generate and transmit imaging signals corresponding to an image of an anatomy of a patient; and providing a console comprising a display and memory having stored therein a plurality of reference materials selected from the group consisting of photographs, video recordings, audio recordings, diagrams, animations, text, and combinations thereof. In accordance with some particular embodiments, each of said reference material can provide information about at least one of anatomy, patient preparation, imaging catheter preparation, imaging catheter placement, imaging catheter operation, imaging catheter features, console preparation, console operation, console features, system operation, system features, and contact information. In some cases, the console can be configured to receive the imaging signals, present at least a portion of at least one image corresponding to the imaging signals on the display, and present a reference menu on the display including menu items corresponding to at least one of the reference materials. In some cases, the console can be configured to simultaneously present on the display a photograph from the plurality of reference materials and a video image corresponding to the image signals from the imaging assembly, wherein the photograph provides a representative anatomical marker or landmark. The method, in accordance with further aspects of the invention, can comprise at least one of storing additional reference materials into the memory, removing at least one reference material from the memory, and replacing the memory with an updated memory, the updated memory having stored therein at least one updated reference material. The method, in accordance with other further cases, can comprise receiving the console from a user; and after receiving the console, at least one of storing additional reference materials into the memory, removing at least one reference materials from the memory, and replacing the memory with an updated memory, the updated memory having stored therein at least one updated reference material.

Figure 46:
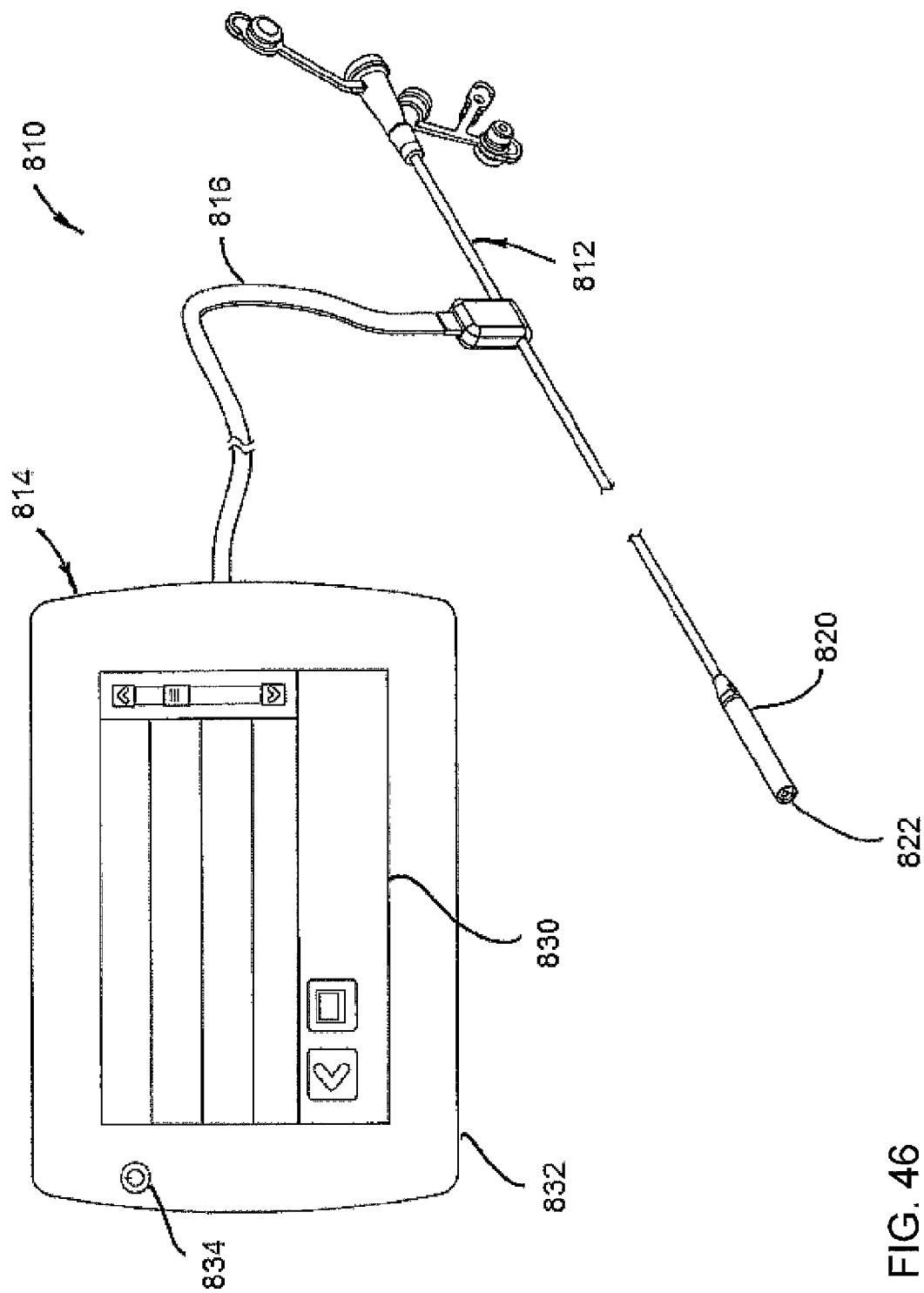
FIG. 46 is a schematic illustration showing a partial perspective view of an imaging catheter system in accordance with one or more aspects of the invention.

Referring to FIG. 46, an imaging catheter system (broadly, a medical system) is generally designated in its entirety by the reference number 810. The system 810 includes an imaging catheter, generally designated 812, and a console 814, operatively coupled to the imaging catheter by, for example, an interface cable 816. The imaging catheter 812 can include an imaging assembly 820 having an imaging device 822 for generating imaging signals corresponding to objects in the field of view thereof. The imaging device is typically an optical sensor and can be a camera or an optical fiber. The imaging assembly may also include elements such as LEDs for illuminating or providing lighting to the field of view. The imaging assembly can further comprise one or more components such as a processor, a memory device to facilitate capture, transformation of the image of the field of view into imaging signals, and transmission of the imaging signals. The imaging device generates and transmits the imaging signals to the console 14 through cable 816 or wirelessly through any suitable communications procedure or protocol. Other cables may be used without departing from the scope of the present invention.

Figure 47:
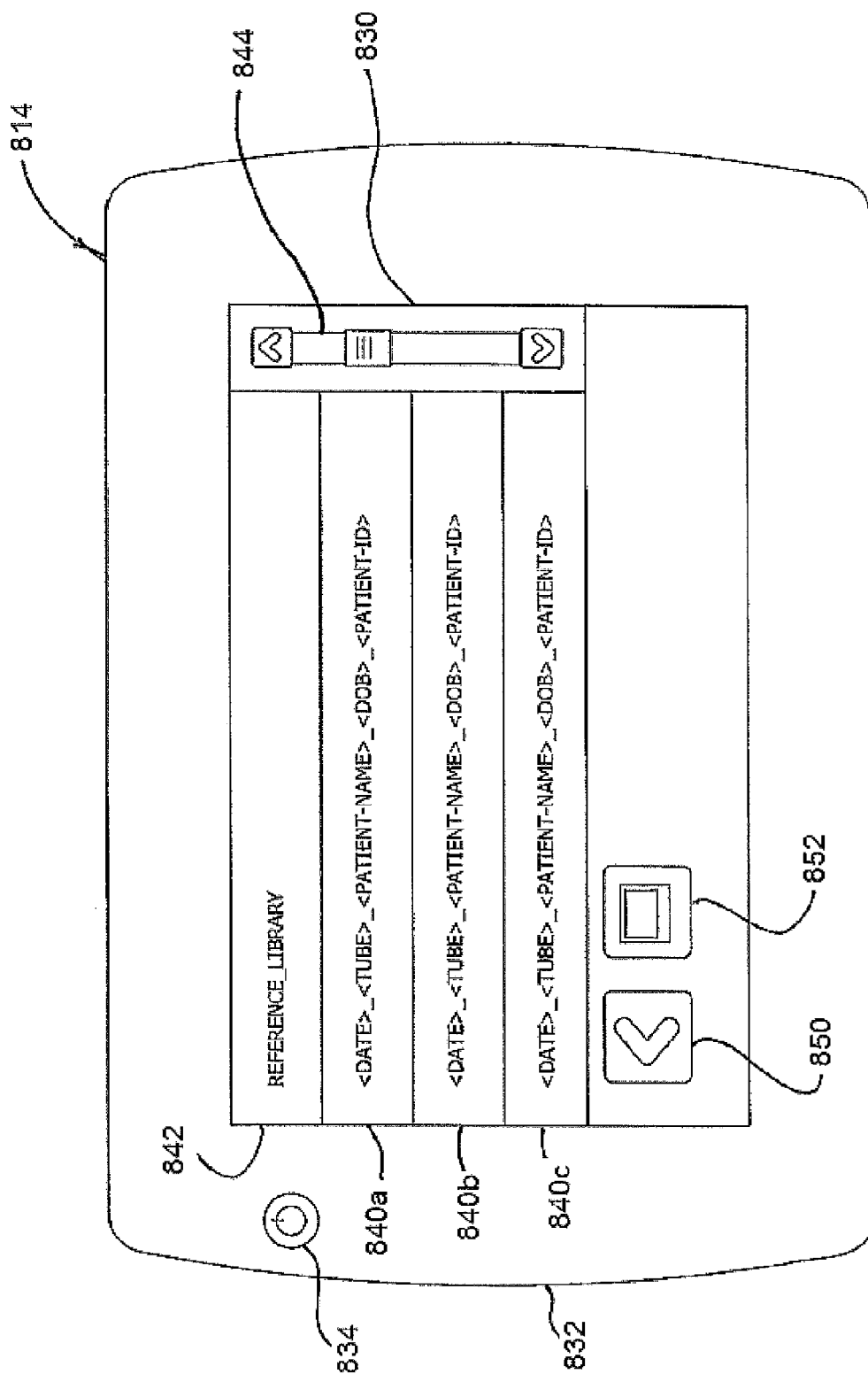
FIG. 47 is a schematic illustration showing a front elevation view of a console of the imaging catheter system in accordance with one or more aspects of the invention.

The console receives and converts the imaging signals from the imaging assembly and presents the images on a display 830 in a housing 832 of the console. As exemplarily shown in FIG. 47, the console can also include a power switch 834 for selectively energizing the console. Other consoles may be used without departing from the scope of the present invention. The display preferably responds to one or more user input or commands, e.g., double tapping the display, to activate and present one or more menus offering a plurality of selections for operating the console and imaging assembly. For example, one of the user inputs causes the display to present a reference menu as illustrated in FIG. 47.

Selections or entries 840a, 840, and 840c may be presented for selection and reviewing stored images of prior procedures performed using the system. As illustrated in FIG. 47, the console can be configured to include and provide a selection 42 titled, "REFERENCE_LIBRARY", which calls from memory a reference menu including menu items corresponding to a library or plurality of reference materials stored in the console memory. For example, the library of reference materials, which may include one or more group of reference materials, may include, for example, photographs, video recordings, audio recordings, diagrams, animations, and/or text. The reference materials provide any one or more of information about anatomy, preparing a patient, preparing the imaging catheter for use, placing the imaging catheter in a patient, console preparation, console operation, console features, overall system operation, overall system features, and/or contact information such as addresses and/or phone numbers that may be used to access further help. Other selections or information that may be provided in the menu may be viewed by manipulating a scroll bar 844 positioned proximate selections 840a-840c and 842 on the display. In some embodiments, command, instruction, and/or navigation icons such as a back icon 850 and a view icon 852, can be provided along the bottom of the display.

In some embodiments (not shown), it is envisioned that the display 30 simultaneously presents the reference menu 42 with images generated from the imaging signals provided by the imaging device. In other embodiments (not shown), it is envisioned that the display 30 presents the reference menu upon sensing a unique input, such as when a user touches the display twice within a preselected period of time. In yet other embodiments (not shown), it is envisioned that the display 30 presents an icon that presents the reference menu when selected by the user. Alternatively, the console 14 may include a button that may be pressed to cause the display 30 to present the reference menu.

Figure 31:
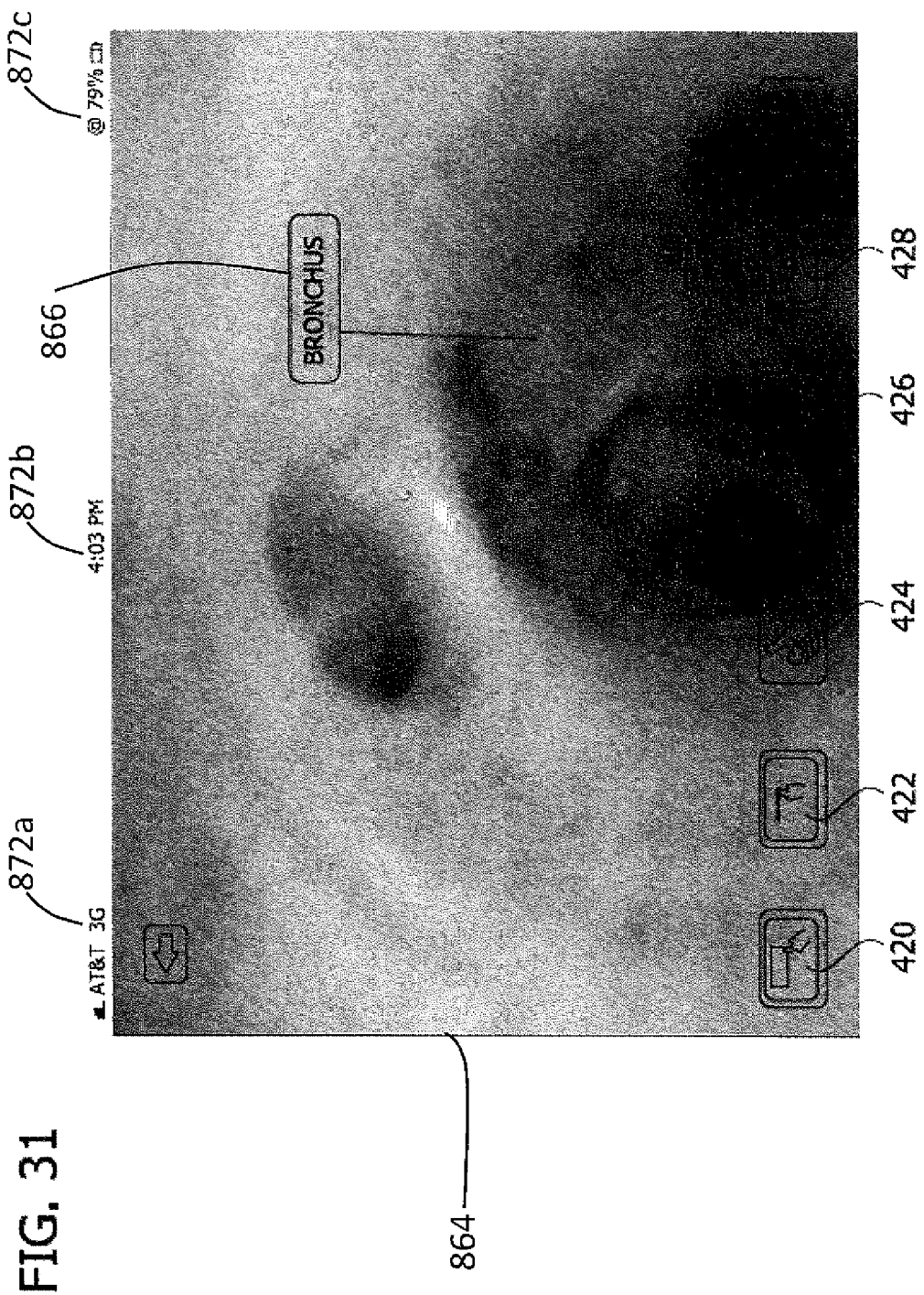
Figure 49A:
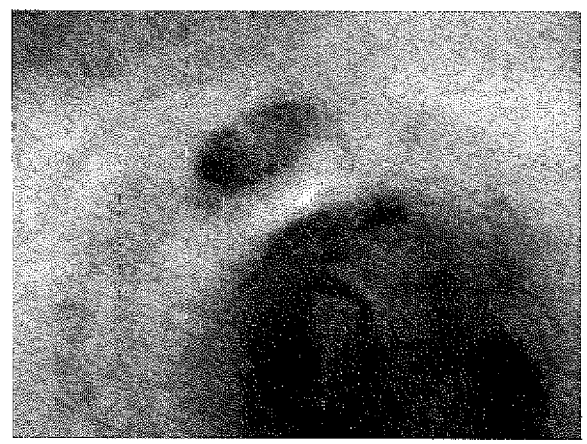
FIGS. 49A-49C are copies of photographs of exemplary markers with FIG. 49A showing a copy of a photograph of a bronchus, FIG. 49B showing a copy of a photograph of a portion of a stomach, and FIG. 49C showing a copy of a photograph of tracheal rings.
Figure 49B:
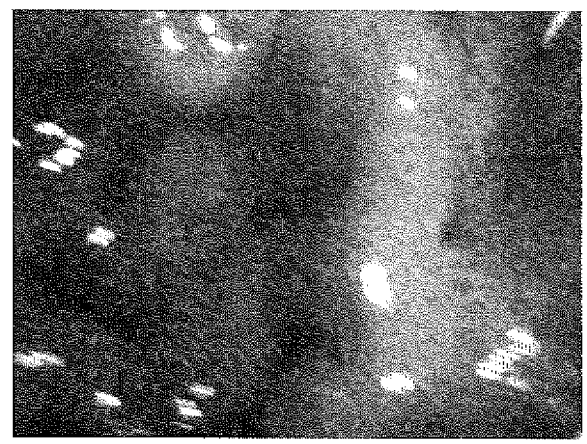
Figure 49C:
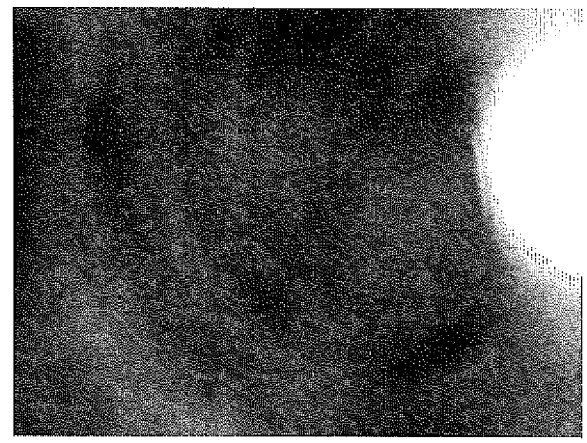

In some embodiments, the console may present reference materials, such as those identified above, simultaneously with the images generated from the imaging signal. For example, as exemplarily illustrated in FIG. 29, a photograph of a typical anatomical feature or marker may be displayed on a portion of the display and live video generated from imaging signals transmitted by the imaging assembly may be displayed on another portion of the display. Thus, a user can identify where the imaging assembly is positioned in the patient by comparing the live video generated from the imaging signals transmitted by the imaging assembly against a reference photograph including anatomical feature or anatomical landmark. Further, as exemplarily shown in FIG. 31, the reference materials, such as a photograph 864, may be presented on the display with one or textual references or indicia 866, providing identifying information or description, such as the names of the target anatomical feature or anatomical marker. The anatomical marker can be any one of a bronchus, a larynx, a tracheal ring, a cardia, a pyloric sphincter, and a pyloric orifice. As is further apparent by a comparison of FIG. 29 and FIG. 31, the visual reference materials may be presented on only a portion of the display or on the entire display. When only a portion of the display is used to present visual reference materials as shown in FIG. 3, other indicators, such as icons 420, 422, 424, 426, and 428) and one or more visual status identifiers 872a, 872b, and 872c may be shown on the display. Alternatively, as shown in FIG. 31, when the entire display is used to present visual reference materials, any one or more of icons 420, 422, 424, 426, and 428 and any one or more of visual status identifiers 772a-872c may be presented over the visual reference materials. In other cases, for example, the console can be operated by selecting a menu to display a copy of a photograph of a representative bronchus, as exemplarily presented in FIG. 49A; a copy of a photograph of a representative stomach with stomach folds, as exemplarily presented in FIG. 49B; and a copy of a photograph of a representative tracheal rings, as exemplarily presented in FIG. 49C, without any identifiers or indicia.

Figure 48:
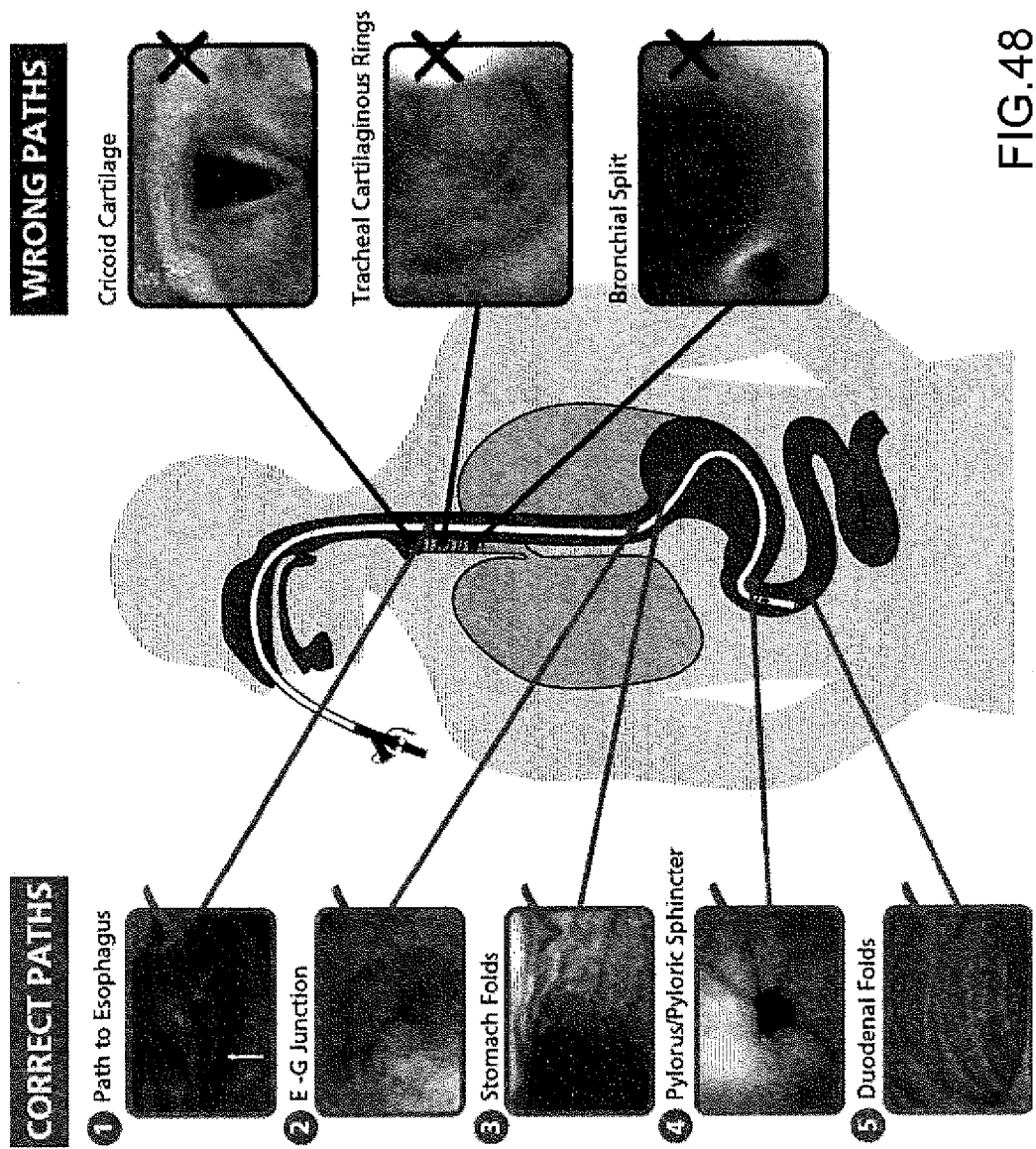
FIG. 48 is a schematic illustration including copies of photographs showing exemplary markers representative of incorrect and correct paths.

The reference materials may also present instructive guidance. For example, the console can be configured to be operated to display a schematic illustration including contrasting correct and incorrect paths, as shown in FIG. 48. Further embodiments contemplate the simultaneous presentation of the schematic illustration of FIG. 48 adjacent real-time or live video images from the imaging apparatus to provide further guidance during use.

In some embodiments of the invention, the materials may be located or stored in a directory having a name corresponding to the particular reference material. For example, portions of a system operation manual could be stored in a directory entitled, "SYSTEM_OPERATION_MANUAL". In some embodiments, the reference material may be saved as read-only files, ensuring the content remains unchanged. Alternatively, oral comments, marginalia, and other annotations may be entered into reference materials and stored as a new file, with or without particular association or links to any of one or more of each of the reference materials in the reference library.

It is further envisioned that reference material files could be modified when updating software. Thus, each software release could also be used to update and improve reference materials for the system. In other cases, the system that has been used in the field can be sent by a user to a servicing, manufacturing, or repair facility whereat the additional reference information may be included in the memory, with or without removing any stored or existing reference material, or portions thereof. In other cases, the received system at the servicing, manufacturing, or repair facility may be updated by having memory components therein replaced, thereby providing updated reference materials.

Depending upon the particular procedure for which the imaging catheter system is used, the system may also include, for example, a conventional feeding tube assembly having a feeding tube for delivering enteral feeding liquid to a patient. A generally conventional feeding tube includes a feeding passage extending between an inlet and an outlet. The imaging catheter may be positioned adjacent the outlet of the feeding tube for generating imaging signals corresponding to a particular portion of the patient's alimentary canal, e.g., a patient's stomach. In some cases, it would be desirable that the imaging assembly is sealed from the feeding passage of the feeding tube to inhibit enteral feeding liquid in the feeding passage from entering the imaging assembly, causing potential damage. In use, reference material, such as video, photographs, or diagrams, is periodically accessed on the display to verify proper placement of the medical instrument in the patient.

One or more further aspects of the invention can be directed to computer-readable media accessible by the console and having stored thereon a plurality of data structures corresponding to reference materials in a reference library, wherein each of the reference material can be audiovisual information including, for example, photographs, video files, audio files, and combinations thereof, as well as textual or graphical information including, for example, diagrams, sketches, and textual information. The reference materials of the reference library in the computer-readable media provides information regarding at least one of an anatomical reference or feature or anatomical landmark, operating instructions of at least one of the imaging catheter, the console, the feeding tube, and contact information regarding at least one of the system, the feeding tube, and the console. Still further aspects of the invention can be directed to providing the computer-readable media having stored thereon the plurality of data structures including the reference library of reference materials, as well as updating the reference library of reference materials by adding additional to or replacing the existing reference materials with updated or revised reference materials. Non-limiting examples of computer-readable media include memory devices and can be optical media and magnetic media, any of which can be in erasable, programmable, or permanent.

Any of the reference materials of the reference library can be stored in any container format or file type such as, but not limited to aiff, wav, xmf, fits, tiff, avi, asf, wma, wmv, 3gp, flv, f4v, iff, jpg, bmp, mpeg, mp4, rm, ogg, pdf, rtf, and txt, any of which can be in any of native and compressed forms. Any of such reference materials can be protected from modification or deletion in the field by a healthcare provider but can be modified, revised or deleted by qualified technician at, for example, a repair or manufacturing facility, or at a servicing facility.

As explained, the console may be configured to recognize a plurality of classes, i.e., statuses, of users, and to limit operations that may be performed by the console as a function of a class associated with each user. For example, the console may be configured to recognize four classes of users: operators, administrators, approval, and maintenance. Depending upon the user class, the reference menus may be changed to adapt to the skill and needs of the user. For example, the console can be configured to authorize administrator class users to create or establish user accounts or other operator accounts, along with respectively associated data storage substructures, and to view video data. The console may be configured to authorize approval class users to view video data and to annotate approval data onto the video data. The console can be configured to authorize maintenance class users to perform maintenance functions to the console such as software updates and time adjustments. The console could be programmed to only authorize maintenance class users to operate the console if no patient data is stored on the console.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense. For example, the simultaneous display of reference anatomical markers may involve progressively showing an expected next or sequential marker after an operator or user has indicated that a current reference anatomical marker has been identified by capturing and optionally annotating a photographic image from the imaging system. When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

What is claimed is:

1. An imaging catheter system, comprising:
a feeding tube having an inlet connectable to a source of feeding fluid, an outlet distal from and fluidly connected to the inlet through a feeding passage, and an imaging device disposed proximate the outlet, the imaging device configured to generate and transmit imaging signals corresponding to an image of an anatomy of a patient; and
a console comprising a display and memory having stored therein a plurality of reference materials selected from the group consisting of photographic data, video data, audio data, diagrams, animations, and combinations thereof, each of the plurality of reference materials providing information about at least one of anatomy, patient preparation, feeding tube preparation, feeding tube placement, feeding tube operation, feeding tube features, console preparation, console operation, console features, system operation, system features, and contact information, wherein the console is configured to receive the imaging signals, present at least a portion of at least one image corresponding to at least a portion of the imaging signals on the display, and present a reference menu on the display including menu items corresponding to at least one of the reference materials, wherein at least one of the reference materials includes feeding tube placement information comprising a previously captured image illustrating prior tube placement within a patient, and the console is configured so that the feeding tube placement information can be periodically accessed on the display to verify proper placement of the feeding tube in the patient, wherein at least one of the plurality of reference materials comprises a partially schematic illustration including contrasting correct and incorrect paths for inserting the feeding tube into the patient, each path including at least one separate representative anatomical image located along the respective path, and wherein the at least one anatomical image of the correct path comprises an image located along an alimentary canal and the at least one anatomical image of the incorrect path comprises an image located along a respiratory path.

2. The imaging catheter system of claim 1, wherein at least one of the plurality of reference materials includes a photograph showing an anatomical landmark.

3. The imaging catheter system of claim 2, wherein the anatomical landmark is one of a bronchus, larynx, tracheal rings, cardia, pyloric sphincter, cricoid cartilage, bronchial split, esophageal junction, stomach folds, duodenal folds, and pyloric orifice.

4. The imaging catheter system of claim 1, wherein the console is configured to present on the display the reference menu simultaneously with the image generated from the imaging signal.

5. The imaging catheter system of claim 1, wherein the console is configured to present on the display at least one of the reference materials simultaneously with the image generated from the imaging signal.

6. The imaging catheter system of claim 1, wherein the console is configured to simultaneously display the schematic illustration and the image generated from the imaging signal for training.

7. The imaging catheter system of claim 1, wherein the partially schematic illustration comprises a schematic illustration of a patient's alimentary canal and respiratory path, and wherein the partially schematic illustrations indicate where the at least one anatomical image located along the alimentary canal is located and where the at least one anatomical image located along the respiratory path is located.

8. The imaging catheter system of claim 1, wherein each path includes a plurality of representative anatomical images located along the respective paths.

9. A method of facilitating use of a feeding tube assembly, comprising:
providing a feeding tube having an inlet connectable to a source of feeding fluid, an outlet distal from and fluidly connected to the inlet through a feeding passage, and an imaging device disposed proximate the outlet, the imaging device configured to generate and transmit imaging signals corresponding to an image of an anatomy of a patient;
providing a console comprising a display and memory having stored therein a plurality of reference materials selected from the group consisting of photographs, video recordings, audio recordings, diagrams, animations, text, and combinations thereof, each of the plurality of the reference materials providing information about at least one of anatomy, patient preparation, imaging catheter preparation, imaging catheter placement, imaging catheter operation, imaging catheter features, console preparation, console operation, console features, system operation, system features, and contact information, wherein the console is configured to receive the imaging signals, present at least a portion of at least one image corresponding to the imaging signals on the display, and present a reference menu on the display including menu items corresponding to at least one of the reference materials, wherein at least one of the reference materials includes feeding tube placement information; and
providing periodic access to the feeding tube placement information comprising a previously captured image illustrating prior tube placement within a patient on the display to verify proper placement of the feeding tube in the patient, wherein at least one of the plurality of reference materials comprises a partially schematic illustration including contrasting correct and incorrect paths for inserting the feeding tube into the patient, each path including at least one separate representative anatomical image located along the respective path, and wherein the at least one anatomical image of the correct path comprises an image located along an alimentary canal and the at least one anatomical image of the incorrect path comprises an image located along a respiratory path.

10. The method of claim 9, wherein the console is configured to simultaneously present on the display a photograph from the plurality of reference materials and a video image corresponding to the image signals from the imaging assembly, wherein the photograph provides a representative anatomical marker.

11. The method of claim 9, further comprising at least one of storing additional reference materials into the memory, removing at least one reference materials from the memory, and replacing the memory with an updated memory, the updated memory having stored therein an updated reference material.

12. The method of claim 9, further comprising:
receiving the console from a user; and
after receiving the console, at least one of storing additional reference materials into the memory, removing at least one reference materials from the memory, and replacing the memory with an updated memory, the updated memory having stored therein at least one updated reference material.

13. An imaging catheter system comprising:
an imaging catheter including an imaging assembly having an imaging device for generating imaging signals corresponding to images of anatomy of a patient, said imaging assembly transmitting the imaging signals generated by the imaging device; and
a console adapted to receive the imaging signals transmitted by the imaging assembly and present images generated from the imaging signals on a display, the console being adapted to selectively present a reference menu on the display including menu items corresponding to reference materials selected from a group of reference materials comprising at least one of photographs, video recordings, audio recordings, diagrams, animations, and text, each of said materials providing information about at least one of anatomy, patient preparation, imaging catheter preparation, imaging catheter placement, imaging catheter operation, imaging catheter features, console preparation, console operation, console features, system operation, system features, and contact information, wherein at least one of the reference materials includes imaging catheter placement information and the console is configured so that the imaging catheter placement information comprising a previously captured image illustrating prior tube placement within a patient, can be periodically accessed on the display to verify proper placement of the imaging catheter in the patient, and wherein at least one of reference materials comprises a partially schematic illustration including contrasting correct and incorrect paths for inserting the feeding tube into the patient, each path including at least one separate representative anatomical image located along the respective path, and wherein the at least one anatomical image of the correct path comprises an image located along an alimentary canal and the at least one anatomical image of the incorrect path comprises an image located along a respiratory path.

14. The imaging catheter system as set forth in claim 13, further comprising a feeding tube assembly including a feeding tube for delivering enteral feeding liquid to the patient, the tube having an inlet and an outlet and a feeding passage extending between said inlet and said outlet, the imaging catheter being positioned adjacent the outlet for generating imaging signals corresponding to an alimentary canal of the patient, the imaging assembly being sealed from the feeding passage to inhibit enteral feeding liquid in the feeding passage from entering the imaging assembly.

* * * * *